(12) United States Patent
Baxter et al.

(10) Patent No.: US 6,946,478 B2
(45) Date of Patent: Sep. 20, 2005

(54) COMPOUNDS

(75) Inventors: Andrew Baxter, Leics. (GB); Stephen Brough, Notts (GB); Nicholas Kindon, Leicestershire (GB); Thomas McInally, Leics. (GB); Bryan Roberts, Leics. (GB); Stephen Thom, Leics. (GB)

(73) Assignee: AstraZeneca AB (SE)

( * ) Notice: Subject to any disclaimer, the term of this patent is extended or adjusted under 35 U.S.C. 154(b) by 139 days.

(21) Appl. No.: 10/339,261

(22) Filed: Jan. 9, 2003

(65) Prior Publication Data
US 2003/0134840 A1 Jul. 17, 2003

Related U.S. Application Data

(63) Continuation of application No. 09/555,565, filed as application No. PCT/SE00/00563 on Mar. 22, 2000, now Pat. No. 6,518,286.

(51) Int. Cl.$^7$ .................. C07D 401/12; C07D 401/06
(52) U.S. Cl. .................. 514/327; 546/217; 546/225; 514/330
(58) Field of Search .............. 514/327, 330, 514/255.05, 326, 252.03, 274, 318, 321, 275; 546/217, 225, 214, 209, 213, 196, 197, 189, 211, 194; 544/409, 324, 269, 322, 238, 312

(56) References Cited

U.S. PATENT DOCUMENTS

| | | | |
|---|---|---|---|
| 4,335,127 A | 6/1982 | Vandenberk et al. | 424/251 |
| 4,853,393 A | 8/1989 | Zimmermann | 514/318 |
| 5,143,923 A | 9/1992 | Hrib et al. | 514/321 |
| 5,210,086 A | 5/1993 | George et al. | 514/275 |
| 6,140,344 A * | 10/2000 | Gong et al. | 514/317 |

FOREIGN PATENT DOCUMENTS

| | | |
|---|---|---|
| EP | 0124476 A1 | 11/1984 |
| EP | 0184258 A2 | 5/1986 |
| EP | 0288563 A1 | 11/1988 |
| FR | 2724382 A1 | 3/1996 |
| JP | 03264579 | 11/1991 |
| JP | 09040646 | 2/1997 |
| JP | 09077742 | 3/1997 |
| WO | WO 9629330 A1 * | 9/1996 ......... C07D/417/04 |
| WO | WO 97/42956 | 11/1997 |
| WO | WO 00/29377 | 5/2000 |
| WO | WO 00/58305 | 10/2000 |

OTHER PUBLICATIONS

CAS printout for Kikuchi et al. Chem. Abs. 128:22926 (JP 09291090).*
CAS printout for Nakazato et al. Chem. Abs. 126:8111 (WO 9629330).*
CAS printout for Takahashi et al. Chem. Abs. 128:294706 (JP 10077271).*
CAS printout for Vandenberk et al.*
Herndon et al., "Ketanserin Analogues: Structure–Affinity Relationships for 5–HT$_2$ and 5–HT$_{1C}$ Serotonin Receptor Binding," *J. Med. Chem.*, vol. 35:4903–4910 (1992).
Hrib et al., "Benzisoxazole– and Benzisothiazole–3–carboxamides as Potential Atypical Antipsychotic Agents," *J. Med. Chem.*, vol. 37:2308–2314 (1994).
C. G. M. Janssen et al., "Synthesis of $^3$H and $^{14}$C Ketanserin," *Journal of Labelled Components and Radiopharmaceuticals*, vol. XXV, No. 7, p. 783–792 (1988).

\* cited by examiner

*Primary Examiner*—James O. Wilson
*Assistant Examiner*—Jason H. Johnsen
(74) *Attorney, Agent, or Firm*—Fish & Richardson P.C.

(57) ABSTRACT

The invention provides compounds of general formula

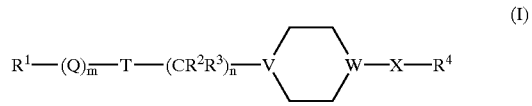

(I)

wherein $R^1$, m, Q, T, n, $R^2$, $R^3$, V, W, X and $R^4$ are as defined in the specification, processes for their preparation, pharmaceutical compositions containing them and their use in therapy.

15 Claims, No Drawings

COMPOUNDS

CROSS REFERENCE TO RELATED CASES

This application is a continuation application of, and claims priority from, U.S. patent application Ser. No., 09/555,565, filed Jun. 1, 2000 now U.S. Pat. No. 6,518,286, which claims priority from PCT Application No. PCT/SE00/00563, filed Mar. 22, 2000, which claims priority from both Swedish Application No. 99011173, filed Mar. 26, 1999 and Swedish Application No. 99021941, filed Jun. 10, 1999. Each of the above applications is hereby incorporated by reference in its entirety.

The present invention relates to novel compounds, processes for their preparation, pharmaceutical compositions containing them and their use in therapy.

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8–14 kDa proteins characterised by a conserved four cysteine motif. The chemokine superfamily can be divided into two main groups exhibiting characteristic structural motifs, the Cys-X-Cys (C-X-C) and Cys-Cys (C-C) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (NAP-2).

The C-C chemokines include potent chemoattractants of monocytes and lymphocytes but not neutrophils such as human monocyte chemotactic proteins 1–3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

Certain piperidinyl derivatives and piperazinyl derivatives are known from U.S. Pat. Nos. 3,787,419, 4,559,349 and 5,210,086 for use respectively as central nervous system depressants, antipsychotic agents and as $\alpha_1$-adrenoreceptor antagonists.

In accordance with the present invention, there is therefore provided a compound of general formula

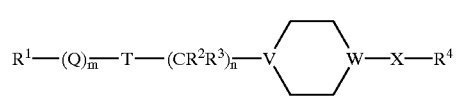

(I)

wherein:
$R^1$ represents a $C_1$–$C_{12}$ alkyl group optionally substituted by one or more substituents independently selected from cyano, hydroxyl, $C_1$–$C_6$ alkoxy, $C_1$–$C_6$ alkylthio and $C_1$–$C_6$ alkoxycarbonyl groups, or
$R^1$ represents a 3- to 10-membered saturated or unsaturated ring system which may comprise up to two ring carbon atoms that form carbonyl groups and which may comprise up to 4 ring heteroatoms independently selected from nitrogen, oxygen and sulfur, the ring system being optionally substituted by one or more substituents independently selected from halogen atoms, and cyano, nitro, hydroxyl, $C_1$–$C_6$ alkyl, $C_3$–$C_6$ cycloalkyl, $C_1$–$C_6$ alkoxy, $C_1$–$C_6$ alkoxycarbonyl, $C_1$–$C_6$ haloalkyl, $C_1$–$C_6$ haloalkoxy, —$NR^5R^6$, $C_3$–$C_6$ cycloalkylamino, $C_1$–$C_6$ alkylthio, $C_1$–$C_6$ alkylthio$C_1$–$C_6$ alkyl, $C_1$–$C_6$ alkylcarbonylamino, —$C(O)NR^7R^8$, sulphonamido (—$SO_2NH_2$), (di)$C_1$–$C_6$ alkylsulphonamido, phenyl, phenylamino, nitrophenyl, pyridyl, pyridylthio, benzodioxanyl, thienyl, furanyl, and $C(O)R^9$-substituted $C_1$–$C_6$ alkyl or $C_1$–$C_6$ alkoxy groups;
m is 0 or 1;
Q represents a group $OCH_2$, $C_1$–$C_4$ alkylene or $C_2$–$C_4$ alkenylene;
T represents a group C(O)NH, or when m is 0, T may additionally represent a bond or a group NH, or when m is 1 and Q represents $C_1$–$C_4$ alkylene, T may additionally represent a group NH;
n is 1, 2, 3 or 4;
each $R^2$ independently represents a hydrogen atom or a $C_1$–$C_4$ alkyl group;
each $R^3$ independently represents a hydrogen atom or a $C_1$–$C_4$ alkyl group;
V represents a nitrogen atom;
W represents a nitrogen atom or a group CH;
X represents an oxygen atom or a group C(O), CH(OH), NH or N($C_1$–$C_6$ alkyl), provided that when W represents a nitrogen atom, then X represents C(O);
$R^4$ represents a phenyl group optionally substituted by one or more substituents independently selected from halogen atoms, and amino, nitro, cyano, sulphonyl (—$SO_3H$), sulphonamido (—$SO_2NH_2$), $C_1$–$C_6$ alkyl, $C_1$–$C_6$ haloalkyl, $C_1$–$C_6$ haloalkoxy and $C_1$–$C_6$ alkylsulphonyl groups;
$R^5$ and $R^6$ each independently represent a hydrogen atom or a $C_1$–$C_6$ alkyl or hydroxy$C_1$–$C_6$ alkyl group, or $R^5$ and $R^6$ together with the nitrogen atom to which they are attached form a 4- to 7-membered saturated heterocyclic ring;
$R^7$ and $R^8$ each independently represent a hydrogen atom or a $C_1$–$C_6$ alkyl group; and
$R^9$ represents a hydroxyl or —$NR^7R^8$ group;
with the provisos that
(a) when m is 0, T is CONH, n is 2, 3 or 4 and each $R^2$ and $R^3$ represents hydrogen, W is CH, X is C(O) or CH(OH) and $R^1$ represents a substituted 3- to 10-membered unsaturated ring system, then the one or more substituents in the ring system do not include hydroxyl, halogen, $C_1$–$C_6$ alkoxy or $C_1$–$C_6$ haloalkoxy, and
(b) when W is N, X is C(O), $R^4$ represents 3-trifluoromethylphenyl, m is 0 and T is a bond, then $R^1$ and $(CR^2R^3)_n$ taken together do not represent a $C_1$–$C_6$ alkyl group, and
(c) when W is CH, X is O, n is 2 or 3 and each $R^2$ and $R^3$ represents hydrogen, m is 0 and T is NH, then $R^1$ does not represent a group

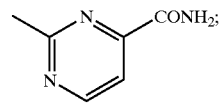

or a pharmaceutically acceptable salt or solvate thereof.

In the context of the present specification, an alkyl substituent group or an alkyl moiety in a substituent group may be linear or branched. Further, the alkyl moieties in a dialkylamino, di(hydroxyalkyl)amino or dialkylsulphonamido substituent group may be the same or different.

$R^1$ represents a $C_1$–$C_{12}$, preferably $C_1$–$C_{10}$, alkyl group optionally substituted by one or more (e.g. one, two, three or four) substituents independently selected from cyano, hydroxyl, $C_1$–$C_6$, preferably $C_1$–$C_4$, alkoxy (e.g. methoxy, ethoxy, propoxy, butoxy, pentoxy or hexoxy), $C_1$–$C_6$, preferably $C_1$–$C_4$, alkylthio (e.g. methyl-, ethyl-, propyl-, butyl-, pentyl- or hexylthio) and $C_1$–$C_6$, preferably $C_1$–$C_4$, alkoxycarbonyl (e.g. methoxy-, ethoxy-, propoxy-, butoxy-, pentoxy- or hexoxycarbonyl) groups, or $R^1$ represents a 3- to 10-membered saturated or unsaturated ring system comprising up to two ring carbon atoms that form carbonyl groups and comprising up to 4 ring heteroatoms independently selected from nitrogen, oxygen and sulfur, the ring system being optionally substituted by one or more (e.g. one, two, three or four) substituents independently selected from halogen atoms (fluorine, chlorine, bromine or iodine), and cyano, nitro, hydroxyl, $C_1$–$C_6$ alkyl (e.g. methyl, ethyl, propyl, isopropyl, butyl, isobutyl, tert-butyl, pentyl or hexyl), $C_3$–$C_6$ cycloalkyl (cyclopropyl, cyclobutyl, cyclopentyl or cyclohexyl), $C_1$–$C_6$ alkoxy (e.g. methoxy, ethoxy, propoxy, butoxy, pentoxy or hexoxy), $C_1$–$C_6$ alkoxycarbonyl (e.g. methoxy-, ethoxy-, propoxy-, butoxy-, pentoxy- or hexoxycarbonyl), $C_1$–$C_6$ haloalkyl (e.g. trifluoromethyl), $C_1$–$C_6$ haloalkoxy (e.g. trifluoromethoxy), —$NR^5R^6$, $C_3$–$C_6$ cycloalkylamino (cyclopropyl-, cyclobutyl-, cyclopentyl- or cyclohexylamino), $C_1$–$C_6$ alkylthio (e.g. methyl-, ethyl-, propyl-, butyl-, pentyl- or hexylthio), $C_1$–$C_6$ alkylthio$C_1$–$C_6$ alkyl (e.g. methylthiomethyl), $C_1$–$C_6$ alkylcarbonylamino (e.g. methyl-, ethyl-, propyl-, butyl-, pentyl- or hexylcarbonylamino), —$C(O)NR\ R^7R^8$, sulphonamido (—$SO_2NH_2$), (di)$C_1$–$C_6$ alkylsulphonamido (e.g. (di)methylsulphonamido or (di)ethylsulphonamido), phenyl, phenylamino, nitrophenyl, pyridyl, pyridylthio, benzodioxanyl, thienyl, furanyl, and $C(O)R^9$-substituted $C_1$–$C_6$ alkyl or $C_1$–$C_6$ alkoxy groups, the alkyl and alkoxy moieties being as defined above.

The 3- to 10-membered saturated or unsaturated ring system in the group $R^1$ may be monocyclic, or polycyclic comprising 2 or more fused rings, examples of which include cyclobutyl, cyclopentyl, cyclohexyl, norbornylenyl, adamantyl, piperidyl, phenyl, naphthyl, naphthyridinyl, 1,3-benzodioxolyl, pyrazolyl, furanyl, pyridyl, thienyl, benzoxazolyl, benzothiazolyl, chromonyl, imidazolyl, quinolinyl, isoquinolinyl, benzimidazolyl, pyrimidinyl, pyrazolopyrimidinyl, thienopyrimidinyl, thiazolopyrimidinyl, pyrimidinedione, pyrazinyl, pyridazinyl, purinyl, quinoxalinyl, thiazolyl, isothiazolyl and 2,4-dioxo-3,4-dihydro-quinazolinyl.

Preferably, $R^1$ represents a $C_1$–$C_{10}$ alkyl group optionally substituted by one or two substituents independently selected from cyano, hydroxyl, $C_1$–$C_4$ alkoxy, $C_1$–$C_4$ alkylthio and $C_1$–$C_4$ alkoxycarbonyl groups, or $R^1$ represents a 3- to 10-membered saturated or unsaturated ring system comprising up to two ring carbon atoms that form carbonyl groups and comprising up to 4 ring heteroatoms independently selected from nitrogen, oxygen and sulfur, the ring system being optionally substituted by one, two or three substituents independently selected from halogen atoms, and cyano, nitro, hydroxyl, $C_1$–$C_4$ alkyl, $C_3$–$C_6$ cycloalkyl, $C_1$–$C_4$ alkoxy, $C_1$–$C_4$ alkoxycarbonyl, $C_1$–$C_3$ haloalkyl, $C_1$–$C_3$ haloalkoxy, —$NR^5R^6$, $C_3$–$C_6$ cycloalkylamino, $C_1$–$C_4$ alkylthio, $C_1$–$C_4$ alkylthio$C_1$–$C_4$ alkyl, $C_1$–$C_4$ alkylcarbonylamino, —$C(O)NR^7R^8$, phenyl, phenylamino, nitrophenyl, pyridyl, pyridylthio, benzodioxanyl, thienyl, furanyl, and $C(O)R^9$-substituted $C_1$–$C_4$ alkyl or $C_1$–$C_4$ alkoxy groups.

Preferably Q represents a group $OCH_2$, $C_1$–$C_3$ alkylene or $C_2$–$C_3$ alkenylene.

Each $R^2$ independently represents a hydrogen atom or a $C_1$–$C_4$ alkyl (e.g. methyl, ethyl, propyl, isopropyl or butyl) group, and is especially a hydrogen atom.

Each $R^3$ independently represents a hydrogen atom or a $C_1$–$C_4$ alkyl (e.g. methyl, ethyl, propyl, isopropyl or butyl) group, and is especially a hydrogen atom.

Preferably n is 2 or 3.

X preferably represents an oxygen atom or a group $C(O)$ or NH.

$R^4$ represents a phenyl group optionally substituted by one or more (e.g. one, two, three or four) substituents independently selected from halogen atoms (fluorine, cholorine, bronine or iodine), and amino, nitro, cyano, sulphonyl (—$SO_3H$), sulphonamido (—$SO_2NH_2$), $C_1$–$C_6$, preferably $C_1$–$C_4$, alkyl (e.g. methyl, ethyl, propyl, butyl, pentyl or hexyl), $C_1$–$C_6$, preferably $C_1$–$C_4$, haloalkyl (e.g. trifluoromethyl), $C_1$–$C_6$, preferably $C_1$–$C_4$, haloalkoxy (e.g. trifluoromethoxy) and $C_1$–$C_6$, preferably $C_1$–$C_4$, alkylsulphonyl (e.g. methyl-, ethyl-, propyl-, butyl-, pentyl- or hexylsulphonyl) groups.

Preferably, $R^4$ represents a phenyl group optionally substituted by one or two halogen atoms, particularly chlorine atoms.

$R^5$ and $R^6$ each independently represent a hydrogen atom or a $C_1$–$C_6$, preferably $C_1$–$C_4$, alkyl or hydroxy$C_1$–$C_6$, preferably $C_1$–$C_4$, alkyl group, or $R^5$ and $R^6$ together with the nitrogen atom to which they are attached form a 4- to 7-membered saturated heterocyclic ring. The alkyl moiety in each case may, for example, be a methyl, ethyl, propyl, butyl, pentyl or hexyl group. In the hydroxyalkyl group, the hydroxyl group may be attached to any suitable carbon atom of the alkyl moiety.

$R^7$ and $R^8$ each independently represent a hydrogen atom or a $C_1$–$C_6$, preferably $C_1$–$C_4$, alkyl (e.g. methyl, ethyl, propyl, butyl, pentyl or hexyl) group. Preferably, $R^7$ and $R^8$ each independently represent a hydrogen atom or a methyl group.

$R^9$ represents a hydroxyl or, preferably, —$NR^5R^6$ group.

Examples of particularly preferred compounds of the invention include:

4-Chloro-N-{2-[4-(3,4-dichlorophenoxy)-1-piperidinyl] ethyl}-2-[2-(dimethylamino)-2-oxoethoxy]benzamide, N-{2-[4-(3,4-Dichlorophenoxy)-1-piperidinyl]ethyl}-3-ethoxybenzamide hydrochloride, N-{2-[4-(3,4-Dichlorophenoxy)-1-piperidinyl]ethyl}-4-isopropoxybenzamide, N-{2-[4-(3,4-Dichlorophenoxy)-1-piperidinyl]ethyl}-4-ethoxybenzamide, N-{2-[4-(3,4-Dichlorophenoxy)-1-piperidinyl]ethyl}-3-(trifluoromethoxy)benzamide hydrochloride, N-{2-[4-(3,4-Dichlorophenoxy)-1-piperidinyl]ethyl}-4-methoxybenzamide, N-{2-[4-(3,4-Dichlorophenoxy)-1-piperidinyl]ethyl}-4-(trifluoromethoxy)benzamide hydrochloride, N-{2-[4-(3,4-Dichlorophenoxy)-1-piperidinyl]ethyl}-2-furamide hydrochloride, N-{2-[4-(3,4-Dichlorophenoxy)-1-piperidinyl]ethyl}-2-phenylacetamnide hydrochloride, N-{2-[4-(3,4-Dichlorophenoxy)-1-piperidinyl]ethyl}-3-methoxybenzamide hydrochloride, 3-Chloro-N-{2-[4-(3,4-dichlorophenoxy)-1-piperidinyl] ethyl}benzamide hydrochloride, N-{2-[4-(3,4-Dichlorophenoxy)-1-piperidinyl]ethyl}-4-fluorobenzamide, N-{2-[4-(3,4-Dichlorophenoxy)-1-piperidinyl]ethyl}-3-fluorobenzamide hydrochloride, N-{2-[4-(3,4-Dichlorophenoxy)-1-piperidinyl]ethyl}-3-hydroxybenzamide hydrochloride,
N-{2-[4-(4-Chlorobenzoyl)-1-piperidinyl]ethyl}-3-[2-(methylamino)-2-oxoethoxy]benzamide hydrochloride,
2-[3-{2-[4-(4-Fluorobenzoyl)-1-piperidinyl]ethyl}-2,4-dioxo-3,4-dihydro-1(2H)-quinazolinyl]-N,N-dimethylacetamide hydrochloride,
N-{2-[4-(3,4-Dichlorobenzoyl)-1-piperazinyl]ethyl}-3-methoxybenzamide hydrochloride,
3,4-Dichloro-N-{2-[4-(3,4-dichlorobenzoyl)-1-piperazinyl]ethyl}benzamide,
4-Chloro-N-{2-[4-(3,4-dichlorobenzoyl)-1-piperazinyl]ethyl}-2-[2-(dimethylamino)-2-oxoethoxy]benzamide hydrochloride,
N~7~-{2-[4-(3,4-Dichlorophenoxy)-1-piperidinyl]ethyl}-5-methyl[1,3]thiazolo[4,5-d]pyrimidine-2,7-diamine,
N-{2-[4-(3,4-Dichlorophenoxy)-1-piperidinyl]ethyl}-9-methyl-9H-purin-6-amine,
N-{2-[4-(3,4-Dichlorophenoxy)-1-piperidinyl]ethyl}-1,3-benzothiazol-2-amine,
N-{2-[4-(3,4-Dichlorophenoxy)-1-piperidinyl]ethyl}-1,3-benzoxazol-2-amine,
6-Chloro-N-{2-[4-(3,4-dichlorophenoxy)-1-piperidinyl]ethyl}-2-pyrazinamine,
6-Chloro-N-{2-[4-(3,4-dichlorophenoxy)-1-piperidinyl]ethyl}-3-pyridazinamine,
6-({2-[4-(3,4-Dichlorophenoxy)-1-piperidinyl]ethyl}amino)-1,3-dimethyl-2,4(1H,3H)-pyrimidinedione,
N-{1-[4-(3,4-Dichlorophenoxy)-piperidin-1-ylmethyl]-2-methyl-propyl}-4-methyl-benzamide, hydrochloride salt,
N-{1-[4-(3,4-Dichloro-phenoxy)-piperidin-1-ylmethyl]-2-methyl-propyl}-3-methoxy-benzamide, hydrochloride salt,
N-{2-[4-(3,4-Dichloroanilino)-1-piperidinyl]ethyl}-3-methoxybenzamide dihydrochloride,
N-{2-[4-(3,4-Dichlorophenoxy)-1-piperidinyl]ethyl}-N-(3-methoxybenzyl)amine dihydrochloride,
3-{2-[4-(3,4-Dichlorophenoxy)-1-piperidinyl]ethyl}-6-methoxy-2,4(1H,3H)-quinazolinedione,
N-{2-[4-(3,4-Dichlorophenoxy)-1-piperidinyl]ethyl}-3-fluorobenzamide,
N-{2-[4-(3,4-Dichlorophenoxy)-1-piperidinyl]ethyl}benzamide,
4-Chloro-N-{2-[4-(3,4-dichlorophenoxy)-1-piperidinyl]ethyl}benzamide,
N-{2-[4-(3,4-Dichlorophenoxy)-1-piperidinyl]ethyl}-4-methoxybenzamide,
N-{2-[4-(3,4-Dichlorophenoxy)-1-piperidinyl]ethyl}-2-methoxybenzamide,
N-{2-[4-(3,4-Dichlorophenoxy)-1-piperidinyl]ethyl}-3-methoxybenzamide,
N-{2-[4-(3,4-Dichlorophenoxy)-1-piperidinyl]ethyl}-2-nitrobenzamide,
N-{2-[4-(3,4-Dichlorophenoxy)-1-piperidinyl]ethyl}-2-methylbenzamide,
N-{2-[4-(3,4-Dichlorophenoxy)-1-piperidinyl]ethyl}-3-(trifluoromethyl)benzamide,
N-{2-[4-(3,4-Dichlorophenoxy)-1-piperidinyl]ethyl}-3,5-dinitrobenzamide,
N-{2-[4-(3,4-Dichlorophenoxy)-1-piperidinyl]ethyl}-2-iodobenzamide,
4-Cyano-N-{2-[4-(3,4-dichlorophenoxy)-1-piperidinyl]ethyl}benzamide,
4-Bromo-N-{2-[4-(3,4-dichlorophenoxy)-1-piperidinyl]ethyl}benzamide,
N-{2-[4-(3,4-Dichlorophenoxy)-1-piperidinyl]ethyl}-4-methylbenzamide,
N-{2-[4-(3,4-Dichlorophenoxy)-1-piperidinyl]ethyl}-4-nitrobenzamide,
3-Bromo-N-{2-[4-(3,4-dichlorophenoxy)-1-piperidinyl]ethyl}benzamide,
3,4-Dichloro-N-{2-[4-(3,4-dichlorophenoxy)-1-piperidinyl]ethyl}benzamide,
N-{2-[4-(3,4-Dichlorophenoxy)-1-piperidinyl]ethyl}-4-fluorobenzamide,
2,4-Dichloro-N-{2-[4-(3,4-dichlorophenoxy)-1-piperidinyl]ethyl}benzamide,
N-{2-[4-(3,4-Dichlorophenoxy)-1-piperidinyl]ethyl}-3-methylbenzamide,
N-{2-[4-(3,4-Dichlorophenoxy)-1-piperidinyl]ethyl}-4-iodobenzamide,
4-Chloro-N-{2-[4-(3,4-dichlorophenoxy)-1-piperidinyl]ethyl}-3-nitrobenzamide,
N-{2-[4-(3,4-Dichlorophenoxy)-1-piperidinyl]ethyl}-4-methyl-3-nitrobenzamide,
N-{2-[4-(3,4-Dichlorophenoxy)-1-piperidinyl]ethyl}-2-fluoro-5-(trifluoromethyl)benzamide,
N-{2-[4-(3,4-Dichlorophenoxy)-1-piperidinyl]ethyl}-3-(trifluoromethoxy)benzamide,
3,5-Dichloro-N-{2-[4-(3,4-dichlorophenoxy)-1-piperidinyl]ethyl}benzamide,
N-{2-[4-(3,4-Dichlorophenoxy)-1-piperidinyl]ethyl}-4-(trifluoromethyl)benzamide,
3-Cyano-N-{2-[4-(3,4-dichlorophenoxy)-1-piperidinyl]ethyl}benzamide,
2-Bromo-N-{2-[4-(3,4-dichlorophenoxy)-1-piperidinyl]ethyl}-5-methoxybenzamide,
N-{2-[4-(3,4-Dichlorophenoxy)-1-piperidinyl]ethyl}-2-furamide,
3-Chloro-N-{2-[4-(3,4-dichlorophenoxy)-1-piperidinyl]ethyl}benzamide,
2-Chloro-N-{2-[4-(3,4-dichlorophenoxy)-1-piperidinyl]ethyl}benzamide,
N-{2-[4-(3,4-Dichlorophenoxy)-1-piperidinyl]ethyl}-3,5-difluorobenzamide,
2,3-Dichloro-N-{2-[4-(3,4-dichlorophenoxy)-1-piperidinyl]ethyl}benzamide,
N-{2-[4-(3,4-Dichlorophenoxy)-1-piperidinyl]ethyl}-2-naphthamide,
N-{2-[4-(3,4-Dichlorophenoxy)-1-piperidinyl]ethyl}-2-(methylsulfanyl)nicotinamide,
N-{2-[4-(3,4-Dichlorophenoxy)-1-piperidinyl]ethyl}-2-fluoro-6-(trifluoromethyl)benzamide,
N-{2-[4-(3,4-Dichlorophenoxy)-1-piperidinyl]ethyl}-2,4-difluorobenzamide,
N-{2-[4-(3,4-Dichlorophenoxy)-1-piperidinyl]ethyl}-2-thiophenecarboxamide,
N-{2-[4-(3,4-Dichlorophenoxy)-1-piperidinyl]ethyl}-2-quinoxalinecarboxamide,
Methyl 4-({2-[4-(3,4-dichlorophenoxy)-1-piperidinyl]ethyl}amino)-4-oxobutanoate,
N-{2-[4-(3,4-Dichlorophenoxy)-1-piperidinyl]ethyl}bicyclo[2.2.1]hept-5-ene-2-carboxamide,
N-{2-[4-(3,4-Dichlorophenoxy)-1-piperidinyl]ethyl}cyclobutanecarboxamide,
N-{2-[4-(3,4-Dichlorophenoxy)-1-piperidinyl]ethyl}-2-methoxyacetamide,
N-{2-[4-(3,4-Dichlorophenoxy)-1-piperidinyl]ethyl}cyclohexanecarboxamide,
(E)-N-{2-[4-(3,4-Dichlorophenoxy)-1-piperidinyl]ethyl}-3-phenyl-2-propenamide,
2-Chloro-N-{2-[4-(3,4-dichlorophenoxy)-1-piperidinyl]ethyl}nicotinamide,
N-{2-[4-(3,4-Dichlorophenoxy)-1-piperidinyl]ethyl}-2-phenylacetamide, N-{2-[4-(3,4-Dichlorophenoxy)-1-piperidinyl]ethyl}cyclopentanecarboxamide,
N-{2-[4-(3,4-Dichlorophenoxy)-1-piperidinyl]ethyl}-2-phenoxyacetamide,
N-{2-[4-(4-Chlorobenzoyl)-1-piperidinyl]ethyl}benzamide,
N-{2-[4-(4-Chlorobenzoyl)-1-piperidinyl]ethyl}-3-(trifluoromethyl)benzamide,
4-(tert-Butyl)-N-{2-[4-(4-chlorobenzoyl)-1-piperidinyl]ethyl}benzamide,
N-{2-[4-(4-Chlorobenzoyl)-1-piperidinyl]ethyl}-4-methylbenzamide,
N-{2-[4-(4-Chlorobenzoyl)-1-piperidinyl]ethyl}-4-nitrobenzamide,
N-{2-[4-(4-Chlorobenzoyl)-1-piperidinyl]ethyl}-3-methylbenzamide,
N-{2-[4-(4-Chlorobenzoyl)-1-piperidinyl]ethyl}-4-methyl-3-nitrobenzamide,
N-{2-[4-(4-Chlorobenzoyl)-1-piperidinyl]ethyl}-3-cyanobenzamide,
N-{2-[4-(4-Chlorobenzoyl)-1-piperidinyl]ethyl}-2-furamide,
N-{2-[4-(4-Chlorobenzoyl)-1-piperidinyl]ethyl}-3-nitrobenzamide,
N-{2-[4-(4-Chlorobenzoyl)-1-piperidinyl]ethyl}-2-naphthamide,
N-{2-[4-(4-Chlorobenzoyl)-1-piperidinyl]ethyl}-2-(methylsulfanyl)nicotinamide,
N-{2-[4-(4-Chlorobenzoyl)-1-piperidinyl]ethyl}-2-(2,3-dihydro-1,4-benzodioxin-2-yl)-1,3-thiazole-4-carboxamide,
N~2~-Cyclopropyl-N~4~-{2-[4-(3,4-dichlorophenoxy)-1-piperidinyl]ethyl}-2,4-pyrimidinediamine,
2-{[4-({2-[4-(3,4-Dichlorophenoxy)-1-piperidinyl]ethyl}amino)-2-pyrimidinyl]amino}-1-ethanol,
2-[[4-({2-[4-(3,4-Dichlorophenoxy)-1-piperidinyl]ethyl}amino)-2-pyrimidinyl](methyl)amino]-1-ethanol,
N~4~-{2-[4-(3,4-Dichlorophenoxy)-1-piperidinyl]ethyl}-N~2~-phenyl-2,4-pyrimidinediamine,
N-{2-[4-(3,4-Dichlorophenoxy)-1-piperidinyl]ethyl}-2-(methylsulfanyl)-4-pyrimidinamine
N~4~-{2-[4-(3,4-Dichlorophenoxy)-1-piperidinyl]ethyl}-6-methyl-2,4-pyrimidinamine,
N~4~-{2-[4-(3,4-Dichlorophenoxy)-1-piperidinyl]ethyl}-N~2~,6-dimethyl-2,4-pyrimidinediamine,
2-Chloro-N~4~-cyclopropyl-N~6~-{2-[4-(3,4-dichlorophenoxy)-1-piperidinyl]ethyl}-4,6-pyrimidinediamine,
N-{2-[4-(3,4-Dichlorophenoxy)-1-piperidinyl]ethyl}-4-phenyl-2-pyrimidinamine,
N~2~-{2-[4-(3,4-Dichlorophenoxy)-1-piperidinyl]ethyl}-N~4~,N~4~,6-trimethyl-2,4-pyrimidinediamine,
N-{2-[4-(3,4-Dichlorophenoxy)-1-piperidinyl]ethyl}-4-(trifluoromethyl)-2-pyrimidinamine,
N-{2-[4-(3,4-Dichlorophenoxy)-1-piperidinyl]ethyl}-4-(propylsulfanyl)-2-pyrimidinamine,
N~2~-{2-[4-(3,4-Dichlorophenoxy)-1-piperidinyl]ethyl}-N~4~-phenyl-2,4-pyrimidinediamine,
N~4~-Cyclopropyl-N~2~-{2-[4-(3,4-dichlorophenoxy)-1-piperidinyl]ethyl}-2,4-pyrimidinediamine,
N-{2-[4-(3,4-Dichlorophenoxy)-1-piperidinyl]ethyl}[1,8]naphthyridin-2-amine,
N-{2-[4-(3,4-Dichlorophenoxy)-1-piperidinyl]ethyl}-4-(3-pyridinyl)-2-pyrimidinamine,
N-{2-[4-(3,4-Dichlorophenoxy)-1-piperidinyl]ethyl}-2-pyrimidinamine,
N-{2-[4-(3,4-Dichlorophenoxy)-1-piperidinyl]ethyl}-4,6-dimethoxy-2-pyrimidinamine,
N-{2-[4-(3,4-Dichlorophenoxy)-1-piperidinyl]ethyl}-4-(3-furyl)-2-pyrimidinamine,
N-{2-[4-(3,4-Dichlorophenoxy)-1-piperidinyl]ethyl}-1-methyl-1H-pyrazolo[3,4-d]pyrimidin-4-amine,
N-{2-[4-(3,4-Dichlorophenoxy)-1-piperidinyl]ethyl}-1H-purin-6-amine,
N-{2-[4-(3,4-Dichlorophenoxy)-1-piperidinyl]ethyl}-5-methylthieno[2,3-d]pyrimidin-4-amine,
N-{2-[4-(3,4-Dichlorophenoxy)-1-piperidinyl]ethyl}-7-methylthieno[3,2-d]pyrimidin-4-amine,
N-{2-[4-(4-Chlorobenzoyl)-1-piperidinyl]ethyl}-2-thiophenecarboxamide,
N-{2-[4-(4-Chlorobenzoyl)-1-piperidinyl]ethyl}-2-quinoxalinecarboxamide,
N-{2-[4-(4-Chlorobenzoyl)-1-piperidinyl]ethyl}bicyclo[2.2.1]hept-5-ene-2-carboxamide,
N-{2-[4-(4-Chlorobenzoyl)-1-piperidinyl]ethyl}cyclohexanecarboxamide,
(E)-N-{2-[4-(4-Chlorobenzoyl)-1-piperidinyl]ethyl}-3-phenyl-2-propenamide,
N-{2-[4-(4-Chlorobenzoyl)-1-piperidinyl]ethyl}-2-phenoxyacetamide,
(E)-N-{2-[4-(4-Chlorobenzoyl)-1-piperidinyl]ethyl}-3-(4-nitrophenyl)-2-propenamide,
2-(1-Adamantyl)-N-{2-[4-(4-chlorobenzoyl)-1-piperidinyl]ethyl}acetamide,
(4-Chlorophenyl)(1-{2-[(2-fluoro-4,5-dimethoxybenzyl)amino]ethyl}-4-piperidinyl)methanone,
(4-Chlorophenyl)(1-{2-[(3,4,5-trimethoxybenzyl)amino]ethyl}-4-piperidinyl)methanone,
(4-Chlorophenyl)(1-{2-[(3-nitrobenzyl)amino]ethyl}-4-piperidinyl)methanone,
(4-Chlorophenyl){1-[2-(isobutylamino)ethyl]-4-piperidinyl}methanone,
4-[({2-[4-(4-Chlorobenzoyl)-1-piperidinyl]ethyl}amino)methyl]-4-ethylhexanenitrile,
(4-Chlorophenyl)(1-{2-[(7-hydroxy-3,7-dimethyloctyl)amino]ethyl}-4-piperidinyl)methanone,
(4-Chlorophenyl)[1-(2-{[(6-nitro-1,3-benzodioxol-5-yl)methyl]amino}ethyl)-4-piperidinyl]methanone,
[1-(2-{[(5-Chloro-1,3-dimethyl-1H-pyrazol-4-yl)methyl]amino}ethyl)-4-piperidinyl](4-chlorophenyl)methanone,
(4-Chlorophenyl)(1-{2-[[3-nitro-4-(2-pyridinylsulfanyl)benzyl]amino}ethyl)-4-piperidinyl]methanone,
(4-Chlorophenyl)[1-(2-{[(E)-3-(4-nitrophenyl)-2-propenyl]amino}ethyl)-4-piperidinyl]methanone,
(4-Chlorophenyl){1-[2-({[5-(3-nitrophenyl)-2-furyl]methyl}amino)ethyl]-4-piperidinyl}methanone,
(4-Chlorophenyl)[1-(2-{[5-nitro-2-(2-pyridinylsulfanyl)benzyl]amino}ethyl)-4-piperidinyl]methanone,
6-[({2-[4-(4-Chlorobenzoyl)-1-piperidinyl]ethyl}amino)methyl]-2-(methylsulfanyl)nicotinonitrile,
{1-[2-({[5-Chloro-1-methyl-3-(trifluoromethyl)-1H-pyrazol-4-yl]methyl}amino)ethyl]-4-piperidinyl}(4-chlorophenyl)methanone,
(4-Chlorophenyl)[1-(2-{[3-(methylsulfanyl)butyl]amino}ethyl)-4-piperidinyl]methanone,
(4-Chlorophenyl)[1-(2-{[(4-phenyl-4-piperidinyl)methyl]amino}ethyl)-4-piperidinyl]methanone,
(4-Chlorophenyl)[1-(2-{[(1-phenyl-1H-pyrazol-5-yl)methyl]amino}ethyl)-4-piperidinyl]methanone,
Ethyl 3-[({2-[4-(4-chlorobenzoyl)-1-piperidinyl]ethyl}amino)methyl]cyclohexanecarboxylate,
N-{4-[({2-[4-(4-Chlorobenzoyl)-1-piperidinyl]ethyl}amino)methyl]phenyl}acetamide,
(4-Chlorophenyl)(1-{2-[(2,5-dichlorobenzyl)amino]ethyl}-4-piperidinyl)methanone, (4-Chlorophenyl)(1-{2-[(4-nitrobenzyl)amino]ethyl}-4-piperidinyl)methanone,
(4-Chlorophenyl)(1-{2-[(2,6-dichlorobenzyl)amino]ethyl}-4-piperidinyl)methanone,
(4-Chlorophenyl)(1-{2-[(2-pyridinylmethyl)amino]ethyl}-4-piperidinyl)methanone,
(4-Chlorophenyl)[1-(2-{[(3-methyl-2-thienyl)methyl]amino}ethyl)-4-piperidinyl]methanone,
(4-Chlorophenyl)(1-{2-[(3-hydroxy-4-methoxybenzyl)amino]ethyl}-4-piperidinyl)methanone,
3-[({2-[4-(4-Chlorobenzoyl)-1-piperidinyl]ethyl}amino)methyl]-4H-chromen-4-one,
[1-(2-{[(5-Chloro-1,3-dimethyl-1H-pyrazol-4-yl)methyl]amino}ethyl)-4-piperidinyl](4-chlorophenyl)methanone,
(4-Chlorophenyl)[1-(2-{[(2,6-dichloro-4-pyridinyl)methyl]amino}ethyl)-4-piperidinyl]methanone,
(4-Chlorophenyl)[1-(2-{[(2-phenyl-1H-imidazol-4-yl)methyl]amino}ethyl)-4-piperidinyl]methanone,
(4-Chlorophenyl)[1-(2-{[(5-ethyl-2-thienyl)methyl]amino}ethyl)-4-piperidinyl]methanone,
(4-Chlorophenyl)[1-(2-{[(2-chloro-3-quinolinyl)methyl]amino}ethyl)-4-piperidinyl]methanone,
(4-Chlorophenyl)[1-(2-{[(6-methyl-2-pyridinyl)methyl]amino}ethyl)-4-piperidinyl]methanone,
(4-Chlorophenyl)(1-{2-[(3-quinolinylmethyl)amino]ethyl}-4-piperidinyl)methanone,
4-[({2-[4-(4-Chlorobenzoyl)-1-piperidinyl]ethyl}amino)methyl]-1,5-dimethyl-2-phenyl-1,2-dihydro-3H-pyrazol-3-one,
(4-Chlorophenyl)(1-{2-[(4-pyridinylmethyl)amino]ethyl}-4-piperidinyl)methanone,
(4-Chlorophenyl)(1-{2-[(3-hydroxy-4-nitrobenzyl)amino]ethyl}-4-piperidinyl)methanone,
(4-Chlorophenyl)(1-{2-[(3,5-difluorobenzyl)amino]ethyl}-4-piperidinyl)methanone,
(1-{2-[(2-Chloro-6-fluorobenzyl)amino]ethyl}-4-piperidinyl)(4-chlorophenyl)methanone,
[1-(2-{[(4-Bromo-1H-pyrazol-3-yl)methyl]amino}ethyl)-4-piperidinyl](4-chlorophenyl)methanone,
3-[({2-[4-(4-Chlorobenzoyl)-1-piperidinyl]ethyl}amino)methyl]-6,7-dimethyl-4H-chromen-4-one,
2-{2-[({2-[4-(4-Chlorobenzoyl)-1-piperidinyl]ethyl}amino)methyl]-4-nitrophenoxy}acetic acid,
(4-Chlorophenyl)[1-(2-{[(1-methyl-1H-benzimidazol-2-yl)methyl]amino}ethyl)-4-piperidinyl]methanone,
(4-Chlorophenyl)[1-(2-{[(2,4-dimethoxy-5-pyrimidinyl)methyl]amino}ethyl)-4-piperidinyl]methanone,
N-{2-[4-(3,4-Dichlorophenoxy)-1-piperidinyl]ethyl}-4-(methylamino)benzamide,
4-Chloro-N-{2-[4-(3,4-dichlorophenoxy)-1-piperidinyl]ethyl}-3-methoxybenzamide,
N-{2-[4-(3,4-Dichlorophenoxy)-1-piperidinyl]ethyl}-3-methoxy-4-methylbenzamide,
3-Amino-N-{2-[4-(3,4-dichlorophenoxy)-1-piperidinyl]ethyl}-4-methoxybenzamide,
N-{2-[4-(3,4-Dichlorophenoxy)-1-piperidinyl]ethyl}-1,3-benzodioxole-5-carboxamide,
4-Amino-N-{2-[4-(3,4-dichlorophenoxy)-1-piperidinyl]ethyl}-3-methoxybenzamide,
N-{2-[4-(3,4-Dichlorophenoxy)-1-piperidinyl]ethyl}-3-fluoro-4-methoxybenzamide,
5-Bromo-N-{2-[4-(3,4-dichlorophenoxy)-1-piperidinyl]ethyl}-2-furamide,
N-{2-[4-(3,4-Dichlorophenoxy)-1-piperidinyl]ethyl}-3-methyl-2-furamide,
N-{2-[4-(3,4-Dichlorophenoxy)-1-piperidinyl]ethyl}-4,5-dimethyl-2-furamide,
N-{2-[4-(3,4-Dichlorophenoxy)-1-piperidinyl]ethyl}-7-ethoxy-1-benzofuran-2-carboxamide,
N-{2-[4-(3,4-Dichlorophenoxy)-1-piperidinyl]ethyl}-5-methoxy-1-benzofuran-2-carboxamide,
N-{2-[4-(3,4-Dichlorophenoxy)-1-piperidinyl]ethyl}-7-methoxy-1-benzofuran-2-carboxamide,
N-{2-[4-(3,4-Dichlorophenoxy)-1-piperidinyl]ethyl}-2-(4-fluorophenyl)acetamide,
N-{2-[4-(3,4-Dichlorophenoxy)-1-piperidinyl]ethyl}-2-(2-methoxyphenyl)acetamide,
N-{2-[4-(3,4-Dichlorophenoxy)-1-piperidinyl]ethyl}-2-(3-methylphenyl)acetamide,
N-{2-[4-(3,4-Dichlorophenoxy)-1-piperidinyl]ethyl}-2-(2-methylphenyl)acetamide,
2-(3-Bromophenyl)-N-{2-[4-(3,4-dichlorophenoxy)-1-piperidinyl]ethyl}acetamide,
2-(2-Chlorophenyl)-N-{2-[4-(3,4-dichlorophenoxy)-1-piperidinyl]ethyl}acetamide,
2-(4-Chlorophenyl)-N-{2-[4-(3,4-dichlorophenoxy)-1-piperidinyl]ethyl}acetamide,
N-{2-[4-(3,4-Dichlorophenoxy)-1-piperidinyl]ethyl}-2-[2-(trifluoromethyl)phenyl]acetamide,
2-(3-Chlorophenyl)-N-{2-[4-(3,4-dichlorophenoxy)-1-piperidinyl]ethyl}acetamide,
N-{2-[4-(3,4-Dichlorophenoxy)-1-piperidinyl]ethyl}-2-(3,4-dimethoxyphenyl)acetamide,
N-{2-[4-(3,4-Dichlorophenoxy)-1-piperidinyl]ethyl}-2-(4-methoxyphenyl)acetamide,
N-{2-[4-(3,4-Dichlorophenoxy)-1-piperidinyl]ethyl}-2-(3,4-dichlorophenyl)acetamide,
N-{2-[4-(3,4-Dichlorophenoxy)-1-piperidinyl]ethyl}-2-(3-fluoro-4-methoxyphenyl)acetamide,
N-{2-[4-(3,4-Dichlorophenoxy)-1-piperidinyl]ethyl}-2-(4-ethoxyphenyl)acetamide,
2-(1,3-Benzodioxol-5-yl)-N-{2-[4-(3,4-dichlorophenoxy)-1-piperidinyl]ethyl}acetamide,
N-{2-[4-(3,4-Dichlorophenoxy)-1-piperidinyl]ethyl}-2-[4-(dimethylamino)phenyl]acetamide,
N-{2-[4-(3,4-Dichlorophenoxy)-1-piperidinyl]ethyl}-2-(4-methylphenyl)acetamide,
N-{2-[4-(3,4-Dichlorophenoxy)-1-piperidinyl]ethyl}-2-(3,4-difluorophenyl)acetamide,
N-{2-[4-(3,4-Dichlorophenoxy)-1-piperidinyl]ethyl}-2-(3-methoxyphenyl)acetamide,
N-{2-[4-(3,4-Dichlorophenoxy)-1-piperidinyl]ethyl}-4-phenylbutanamide,
N-{2-[4-(3,4-Dichlorophenoxy)-1-piperidinyl]ethyl}-3-phenylpropanamide,
N-{2-[4-(3,4-Dichlorophenoxy)-1-piperidinyl]ethyl}-3-(3-methoxyphenyl)propanamide,
2-Amino-N-{2-[4-(3,4-dichlorophenoxy)-1-piperidinyl]ethyl}-1,3-thiazole-4-carboxamide,
2-(Acetylamino)-N-{2-[4-(3,4-dichlorophenoxy)-1-piperidinyl]ethyl}-1,3-thiazole-4-carboxamide,
N-{2-[4-(3,4-Dichlorophenoxy)-1-piperidinyl]ethyl}-2-(4-pyridinyl)-1,3thiazole-4-carboxamide,
N-{2-[4-(3,4-Dichlorophenoxy)-1-piperidinyl]ethyl}-2,4-dimethyl-1,3-thiazole-5-carboxamide,
N-{2-[4-(3,4-Dichlorophenoxy)-1-piperidinyl]ethyl}-2,5-dimethyl-1,3-oxazole-4-carboxamide,
N-{2-[4-(3,4-Dichlorophenoxy)-1-piperidinyl]ethyl}-1H-imidazole-4-carboxamide,
N-{2-[4-(3,4-Chlorophenoxy)-1-piperidinyl]ethyl}-3-methoxybenzamide, hydrochloride salt,
N-{3-[4-(3,4-Dichlorophenoxy)-1-piperidinyl]propyl}-1-methyl-1H-pyrazolo[3,4-d]pyrimidin-4-amine,
N-{3-[4-(3,4-Dichlorophenoxy)-1-piperidinyl]propyl}-2,6-dimethoxy-4-pyrimidinamine, N~4~-{3-[4-(3,4-Dichlorophenoxy)-1-piperidinyl]propyl}-N~2~,N~2~-dimethyl-2,4-pyrimidinediamine,
N-{3-[4-(3,4-Dichlorophenoxy)-1-piperidinyl]propyl}-2-[(methylsulfanyl)methyl]-4-pyrimidinamine,
N-{3-[4-(3,4-Dichlorophenoxy)-1-piperidinyl]propyl}-2-(methylsulfanyl)-6-(trifluoromethyl)-4-pyrimidinamine,
N-{3-[4-(3,4-Dichlorophenoxy)-1-piperidinyl]propyl}-5-methoxy-2-(methylsulfanyl)-4-pyrimidinamine,
N-{3-[4-(3,4-Dichlorophenoxy)-1-piperidinyl]propyl}-6-methyl-2-(methylsulfanyl)-4-pyrimidinamine,
N-{3-[4-(3,4-Dichlorophenoxy)-1-piperidinyl]propyl}-5-methoxy-2-methyl-4-pyrimidinamine,
N-{3-[4-(3,4-Dichlorophenoxy)-1-piperidinyl]propyl}-2-(ethylsulfanyl)-6-methyl-4-pyrimidinamine,
N~2~-Cyclopropyl-N~4~-{3-[4-(3,4-dichlorophenoxy)-1-piperidinyl]propyl}-2,4-pyrimidinediamine,
2-{[4-({3-[4-(3,4-Dichlorophenoxy)-1-piperidinyl]propyl}amino)-2-pyrimidinyl]amino}-1-ethanol,
2-[[4-({3-[4-(3,4-Dichlorophenoxy)-1-piperidinyl]propyl}amino)-2-pyrimidinyl](methyl)amino]-1-ethanol,
N-{3-[4-(3,4-Dichlorophenoxy)-1-piperidinyl]propyl}-2-(methylsulfanyl)-4-pyrimidinamine,
N~4~-{3-[4-(3,4-Dichlorophenoxy)-1-piperidinyl]propyl}-6-methyl-2,4-pyrimidinediamine,
N~4~-{3-[4-(3,4-Dichlorophenoxy)-1-piperidinyl]propyl}-N~2~,6-dimethyl-2,4-pyrimidinediamine,
N-{3-[4-(3,4-Dichlorophenoxy)-1-piperidinyl]propyl}-4-phenyl-2-pyrimidinamine,
N~2~-{3-[4-(3,4-Dichlorophenoxy)-1-piperidinyl]propyl}-5-fluoro-2,4-pyrimidinediamine,
N~2~-{3-[4-(3,4-Dichlorophenoxy)-1-piperidinyl]propyl}-N~4~,N~4~,6-trimethyl-2,4-pyrimidinediamine,
N-{3-[4-(3,4-Dichlorophenoxy)-1-piperidinyl]propyl}-4-(trifluoromethyl)-2-pyrimidinamine,
N-{3-[4-(3,4-Dichlorophenoxy)-1-piperidinyl]propyl}-4-(propylsulfanyl)-2-pyrimidinamine,
N~2~-{3-[4-(3,4-Dichlorophenoxy)-1-piperidinyl]propyl}-N~4~-phenyl-2,4-pyrimidinediamine,
N~2~-{3-[4-(3,4-Dichlorophenoxy)-1-piperidinyl]propyl}-N~4~,6-dimethyl-2,4-pyrimidinediamine,
N-{3-[4-(3,4-Dichlorophenoxy)-1-piperidinyl]propyl}[1,8]naphthyridin-2-amine,
2-{[2-({3-[4-(3,4-Dichlorophenoxy)-1-piperidinyl]propyl}amino)-4-pyrimidinyl]amino}-1-ethanol,
2-[[2-({3-[4-(3,4-Dichlorophenoxy)-1-piperidinyl]propyl}amino)-4-pyrimidinyl](methyl)amino]-1-ethanol,
N-{3-[4-(3,4-Dichlorophenoxy)-1-piperidinyl]propyl}-4-(3-pyridinyl)-2-pyrimidinamine,
N-{3-[4-(3,4-Dichlorophenoxy)-1-piperidinyl]propyl}-4-(3-thienyl)-2-pyrimidinamine,
N-{3-[4-(3,4-Dichlorophenoxy)-1-piperidinyl]propyl}-2-pyrimidinamine,
N-{3-[4-(3,4-Dichlorophenoxy)-1-piperidinyl]propyl}-4,6-dimethoxy-2-pyrimidinamine,
N-{3-[4-(3,4-Dichlorophenoxy)-1-piperidinyl]propyl}-4-(3-furyl)-2-pyrimidinamine,
N-{3-[4-(3,4-Dichlorophenoxy)-1-piperidinyl]propyl}-4-(2-thienyl)-2-pyrimidinamine,
N-{3-[4-(3,4-Dichlorophenoxy)-1-piperidinyl]propyl}-1H-purin-6-amine,
N-{3-[4-(3,4-Dichlorophenoxy)-1-piperidinyl]propyl}-5-methylthieno[2,3-d]pyrimidin-4-amine,
N-{3-[4-(3,4-Dichlorophenoxy)-1-piperidinyl]propyl}-7-methylthieno[3,2-d]pyrimidin-4-amine,
N~7~-{3-[4-(3,4-Dichlorophenoxy)-1-piperidinyl]propyl}-5-methyl[1,3]thiazolo[4,5-d]pyrimidine-2,7-diamine,
N-{3-[4-(3,4-Dichlorophenoxy)-1-piperidinyl]propyl}-9-methyl-9H-purin-6-amine,
N-{3-[4-(3,4-Dichlorophenoxy)-1-piperidinyl]propyl}-2-pyridinamine,
5-Chloro-N-{3-[4-(3,4-dichlorophenoxy)-1-piperidinyl]propyl}-2-pyridinamine,
6-Chloro-N-{3-[4-(3,4-dichlorophenoxy)-1-piperidinyl]propyl}-2-pyridinamine,
N-{3-[4-(3,4-Dichlorophenoxy)-1-piperidinyl]propyl}-6-methyl-2-pyridinamine,
N-{3-[4-(3,4-Dichlorophenoxy)-1-piperidinyl]propyl}-1,3-benzothiazol-2-amine,
N-{3-[4-(3,4-Dichlorophenoxy)-1-piperidinyl]propyl}-1,3-benzoxazol-2-amine,
6-Chloro-N-{3-[4-(3,4-dichlorophenoxy)-1-piperidinyl]propyl}-2-pyrazinamine,
6-Chloro-N-{3-[4-(3,4-dichlorophenoxy)-1-piperidinyl]propyl}-3-pyridazinamine,
6-({3-[4-(3,4-Dichlorophenoxy)-1-piperidinyl]propyl}amino)-1,3-dimethyl-2,4(1H,3H)-pyrimidinedione,
N-{2-[4-(3,4-Dichlorophenoxy)-1-piperidinyl]ethyl}-2,6-dimethoxy-4-pyrimidinamine,
N~4~-{2-[4-(3,4-Dichlorophenoxy)-1-piperidinyl]ethyl}-N~2~,N~2~-dimethyl-2,4-pyrimidinediamine,
N-{2-[4-(3,4-Dichlorophenoxy)-1-piperidinyl]ethyl}-2-[(methylsulfanyl)methyl]-4-pyrimidinamine,
N-{2-[4-(3,4-Dichlorophenoxy)-1-piperidinyl]ethyl}-5-methoxy-2-(methylsulfanyl)-4-pyrimidinamine,
N-{2-[4-(3,4-Dichlorophenoxy)-1-piperidinyl]ethyl}-6-methyl-2-(methylsulfanyl)-4-pyrimidinamine,
N-{2-[4-(3,4-Dichlorophenoxy)-1-piperidinyl]ethyl}-5-methoxy-2-methyl-4-pyrimidinamine, and
N~4~-{2-[4-(3,4-Dichlorophenoxy)-1-piperidinyl]ethyl}-6-methyl-N~2~-phenyl-2,4-pyrimidinediamine.

The present invention further provides a process for the preparation of a compound of formula (I) which comprises
(i) when T represents a group C(O)NH, reacting a compound of general formula $$R^1\text{-}(Q)_m\text{-}COL^1 \quad (II)$$

wherein $L^1$ represents a leaving group (e.g. a hydroxyl or halide, such as chloride, group) and $R^1$, m and Q are as defined in formula (I), with a compound of general formula

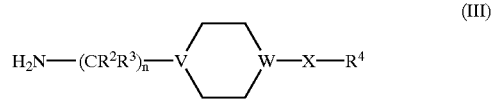

or an acid addition salt thereof (e.g. trifluoroacetate) wherein n, $R^2$, $R^3$, V, W, X and $R^4$ are as defined in formula (I); or
(ii) when T represents a group C(O)NH and W represents a nitrogen atom, reacting a compound of general formula

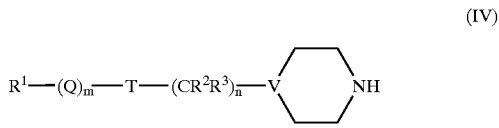

wherein $R^1$, m, Q, T, n, $R^2$, $R^3$ and V are as defined in formula (I), with a compound of general formula $$L^2\text{-}X\text{—}R^4 \quad (V)$$

wherein $L^2$ represents a leaving group (e.g. a halogen atom) and X and $R^4$ are as defined in formula (I); or
(iii) when T represents a group NH and m is 0, reacting a compound of general formula $$R^1\text{-}L^3 \tag{VI}$$

wherein $L^3$ represents a leaving group (e.g. a halogen atom) and $R^1$ is as defined in formula (I), with a compound of formula (III) as defined in (i) above; or (iv) when T represents a group NH, m is 1 and Q represents $C_1$–$C_4$ alkylene, reacting a compound of general formula $$R^1\text{—}(CH_2)_p\text{—}CHO \tag{VII}$$

wherein p is 0, 1, 2 or 3 and $R^1$ is as defined in formula (I), with a compound of formula (III) as defined in (i) above; or (v) when T represents a bond and m is 0, reacting a compound of general formula $$R^1\text{—}(CR^2R^3)_n\text{-}L^4 \tag{VIII}$$

wherein $L^4$ represents a leaving group such as a halogen atom (e.g. chlorine) and n, $R^1$, $R^2$ and $R^3$ are as defined in formula (I), with a compound of general formula

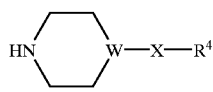

(IX)

wherein W, X and $R^4$ are as defined in formula (I);
and optionally after (i), (ii), (iii), (iv) or (v) converting the compound of formula (I) to a further compound of formula (I) and/or forming a pharmaceutically acceptable salt or solvate of the compound of formula (I).

The processes of the invention may conveniently be carried out in a solvent, e.g. an organic solvent such as dimethylformamide or dichloromethane at a temperature of, for example, 15° C. or above such as a temperature in the range from 20 to 100° C.

Compounds of formula (III) in which W represents a nitrogen atom may be prepared by reacting a compound of general formula

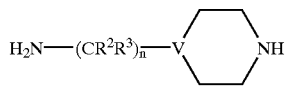

(X)

in which n, $R^2$, $R^3$ and V are as defined in formula (I) with a compound of formula (V) as defined above.

Compounds of formula (X) can be prepared by reacting piperazine with a compound of general formula $$H_2N\text{—}(CR^2R^3)_n\text{-}L^5 \tag{XI}$$

wherein $L^5$ represents a halogen atom such as a bromine atom and n, $R^2$ and $R^3$ are as defined in formula (I).

Compounds of formula (III) in which W represents a group CH and X represents an oxygen atom may be prepared by reacting a compound of general formula

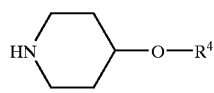

(XII)

in which $R^4$ is as defined in formula (I), with a compound of formula (XI).

Compounds of formula (XII) may be prepared by reacting 4-piperidinol with a compound of general formula (XIII), $R^4$—OH, wherein $R^4$ is as defined in formula (I), in the presence of a coupling agent such as diethyl azodicarboxylate and triphenylphosphine and in a solvent such as benzene or tetrahydrofuran at a temperature typically in the range from 20 to 30° C.

Compounds of formula (III) in which W represents a group CH and X represents a group C(O) may be prepared by reacting a compound of general formula

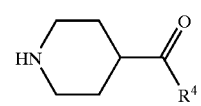

(XIV)

wherein $R^4$ is as defined in formula (I), with a compound of formula (XI).

Compounds of formula (III) in which W represents a group CH and X represents a group CH(OH) may be prepared by reducing/hydrogenating a corresponding compound of formula (III) in which X represents C(O) using techniques known in the art.

Compounds of formula (III) in which W represents a group CH and X represents a group NH may be prepared by reacting a compound of general formula

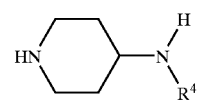

(XV)

in which $R^4$ is as defined in formula (I), with a compound of formula (XI).

Compounds of formula (XV) may be prepared by reacting 4-piperidone with a compound of general formula (XVI), $R^4$—$NH_2$, wherein $R^4$ is as defined in formula (I), in the presence of a reducing agent such as sodium cyanoborohydride or sodium borohydride and in a solvent such as methanol or benzene at a temperature typically in the range from 20 to 90° C.

Compounds of formula (III) in which W represents a group CH and X represents a group N($C_1$–$C_6$ alkyl) may be prepared by alkylating a corresponding compound of formula (III) in which X represents a group NH, using techniques conventional in the art.

Compounds of formula (IV) may be prepared by reacting a compound of formula (II) with a compound of formula (X).

Compounds of formulae II, V, VI, VII, VIII, IX, XI, XIII, XIV and XVI are either commercially available, are well known in the literature or may be prepared easily using known techniques.

Compounds of formula (I) can be converted into further compounds of formula (I) using standard procedures. For example, compounds of formula (I) in which $R^1$ represents an alkoxy-substituted phenyl group can be converted to compounds of formula (I) in which $R^1$ represents a hydroxy-substituted phenyl group by reaction with boron tribromide in a solvent such as dichloromethane. Further, compounds of formula (I) in which X represents C(O) can be converted to compounds of formula (I) in which X represents CH(OH) by reaction with triethylsilane and trifluoroacetic acid in a solvent such as dichloromethane.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate.

Certain compounds of formula (I) are capable of existing in stereoisomeric forms. It will be understood that the invention encompasses the use of all geometric and optical isomers of the compounds of formula (I) and mixtures thereof including racemates. The use of tautomers and mixtures thereof also form an aspect of the present invention.

The compounds of formula (I) have activity as pharmaceuticals, in particular as modulators of chemokine receptor (especially CCR1 and/or CCR3) activity, and may be used in the treatment of autoimmune, inflammatory, proliferative and hyperproliferative diseases and immunologically-mediated diseases including rejection of transplanted organs or tissues and Acquired Immunodeficiency Syndrome (AIDS).

Examples of these conditions are:

(1) (the respiratory tract) obstructive airways diseases including chronic obstructive pulmonary disease (COPD) such as irreversible COPD; asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;

(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura; and (6) (allograft rejection) acute and chronic following, for example, transplantation of kidney, heart, liver, lung, bone marrow, skin and cornea; and chronic graft versus host disease.

Thus, the present invention provides a compound of formula (I), or a pharmaceutically-acceptable salt or solvate thereof, as hereinbefore defined for use in therapy.

In a further aspect, the present invention provides the use of a compound of formula (I), or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention also provides a method of treating an inflammatory disease in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The invention will now be further explained by reference to the following illustrative examples.

EXAMPLE 1

4-Chloro-N-{2-[4-(3,4-dichlorophenoxy)-1-piperidinyl]ethyl}-2-[2-(dimethylamino)-2-oxoethoxy]benzamide

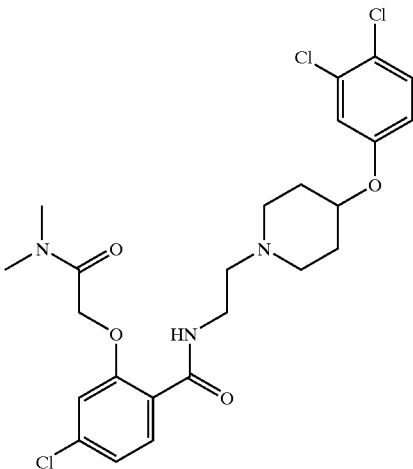

(i) tert-Butyl 4-(3,4-dichlorophenoxy)-1-piperidinecarboxylate

Diethyl azodicarboxylate (12.6 ml) was added to a solution of triphenylphosphine (20.8 g) in tetrahydrofuran (300 ml) at 0° C. After 15 minutes 3,4-dichlorophenol (12.9 g) was added, after a further 10 minutes tert-butyl 4-hydroxy-1-piperidinecarboxylate (14.5 g) in tetrahydrofuran (100 ml) was added dropwise over 0.5 hour. The solution was stirred at room temperature for 5 hours and concentrated to a small volume. The residue was partitioned between ether and brine. The organic phase was separated, dried and evaporated to a gum. Purification by chromatography (ethyl acetate:isohexane 95:5) gave the sub-titled product as an oil (20 g).

MS: APCI(+ve): 246 (M-BOC+2H)

(ii) 4-(3,4-Dichlorophenoxy)piperidine

The product from step (i) was dissolved in dichloromethane (200 ml) and trifluoroacetic acid (100 ml) was added. After 18 hours at room temperature the solution was evaporated and the resultant gum triturated under ether to give the sub-titled product as a solid (16.2 g).

(iii) tert-Butyl 2-[4-(3,4-dichlorophenoxy)-1-piperidinyl]ethylcarbamate

The product from step (ii) (6.55 g) was dissolved in DMF (50 ml) and triethylamine (7.9 ml) was added. tert-Butyl 2-bromoethylcarbamate (4.3 g) in DMF (5 ml) was added and the solution stirred at room temperature for 3 days. Ethyl acetate and water were added, the organic phase separated, dried and evaporated to a gum. Purification by chromatography (dichloromethane:methanol 95:5) gave the sub-titled product as a gum (5.7 g).

MS: APCI(+ve): 389 (M+H).

(iv) 2-[4-(3,4-Dichlorophenoxy)-1-piperidinyl]ethylamine trifluoroacetate

The product from step (iii) was dissolved in dichloromethane (200 ml) and trifluoroacetic acid (100 ml) added. After 18 hrs at room temperature the solvent was evaporated and the resultant gum triturated under ether to give the sub-titled product as a solid (5.7 g).

MS: APCI(+ve): 290 (M+H).

(v) 2-(Dimethylamino)-2-oxoethyl 4-chloro-2-[2-(dimethylamino)-2-oxoethoxy]benzoate A mixture of 4-chloro-2-hydroxybenzoic acid (5 g), $Cs_2CO_3$ (17.5 g) and 2-chloro-N,N-dimethylacetamide (6.6 g) was stirred and heated at 70° C. for 3 hours. Water and ethyl acetate were added, the organic phase separated, dried and concentrated to a gum which was purified by chromatography (ethyl acetate:methanol, 9:1) to give the sub-titled product as a solid (8.0 g).

MS: APCI(+ve) 343 (M+H).

Melting point: 140–141° C.

(vi) 4-Chloro-2-[2-(dimethylamino)-2-oxoethoxy]benzoic acid

The product from step (v) (1.0 g) was dissolved in a 2:1 water:methanol mixture (15 ml) and LiOH.H_2O added. After 2 hours 2M aqueous HCl solution and ethyl acetate were added, the organic phase separated, dried and concentrated to give the sub-titled product as a solid (1.2 g).

MS: APCI(+ve) 258 (M+H).

Melting point: 141–142° C.

(vii) 4-Chloro-N-{2-[4-(3,4-dichlorophenoxy)-1-piperidinyl]ethyl}-2-[2-(dimethylamino)-2-oxoethoxy]benzamide The product from step (vi) (0.3 g) and N,N-carbonyldiimidazole (0.19 g) were dissolved in DMF (20 ml) and the solution stirred at room temperature for 1 hour. The product from step (iv) (0.42 g) and triethylamine (0.32 ml) were added. After 20 hours water and ether were added, the organic phase separated, dried and concentrated to a gum which was purified by chromatography (dichloromethane:methanol, 93:7) to give the titled product as a solid (0.38 g).

MS: ESI 528.12 (M+H).

$^1$H NMR: δ(DMSO) 9.17 (t, 1H), 7.88 (d, 1H), 7.48 (d, 1H), 7.38 (d, 1H), 7.24 (d, 1H), 7.13 (dd, 1H), 6.99 (dd, 1H), 5.11 (s, 2H), 4.32 (m, 1H), 3.42 (m, 2H), 2.99 (s, 3H), 2.88 (s, 3H), 2.73 (m, 2H), 2.50 (m, 2H), 2.30 (m, 2H), 1.90 (m, 2H), 1.59 (m, 2H).

Melting point: 139–40° C.

EXAMPLE 2

N-{2-[4-(3,4-Dichlorophenoxy)-1-piperidinyl]ethyl}-3-ethoxybenzamide hydrochloride

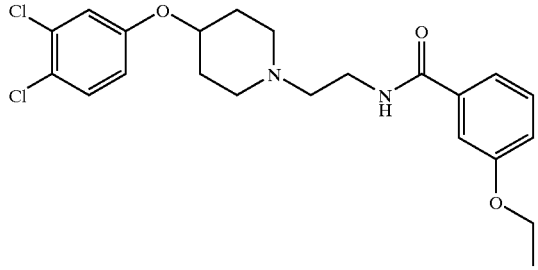

The product of Example 1 step (iv) (0.4 g) was dissolved in DMF (10 ml), PyBrop (0.541 g), 3-ethoxybenzoic acid (0.167 g ) and N,N-di-isopropylethylamine (0.5 g) were added. After 18 hours at room temperature chloroform and aqueous $NaHCO_3$ solution were added. The organic phase was separated, dried and concentrated to leave a gum which was purified by chromatography (ethyl acetate:methanol 97:3) to give an oil. Addition of 1.0M ethereal hydrogen chloride solution gave the titled product as a solid (0.14 g).

MS: ESI 437.14 (M+H).

¹H NMR: δ(DMSO) 8.87 (bs, 1H), 7.50 (m, 3H), 7.40 (m, 2H), 7.06 (m, 2H), 4.83/4.62 (m, 1H), 4.08 (q, 2H), 3.67 (m, 3H), 3.47 (m, 1H), 3.17 (m, 3H), 2.20 (m, 2H), 2.03 (m, 2H), 1.34 (t, 3H).

Melting point: 191–193° C.

EXAMPLE 3

N-{2-[4-(3,4-Dichlorophenoxy)-1-piperidinyl]ethyl}-4-isopropoxybenzamide

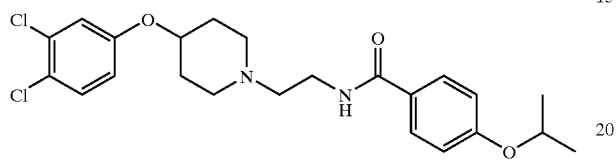

Prepared by the same method as Example 2 using 4-isopropoxybenzoic acid without the addition of 1.0 M ethereal hydrogen chloride solution to give the titled product as a solid (0.12 g).

MS: ESI 451.14 (M+H).

¹H NMR: δ(DMSO) 8.22 (t, 1H), 7.8 (m, 2H), 7.49 (d, 1H), 7.25 (d, 1H), 7.00 (m, 3H), 4.7 (m, 1H), 4.45 (m, 1H), 3.36 (m, 2H), 2.73 (m, 2H), 2.48 (m, 2H), 2.29 (m, 2H), 1.91 (m, 2H), 1.60 (m, 2H), 1.28 (s, 3H), 1.27 (s, 3H).

Melting point: 113–15° C.

EXAMPLE 4

N-{2-[4-(3,4-Dichlorophenoxy)-1-piperidinyl]ethyl}-4-ethoxybenzamide

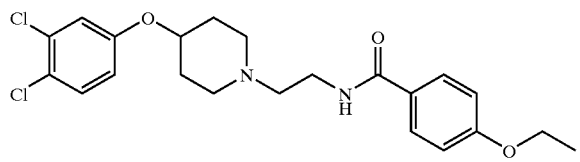

Prepared by the same method as Example 2 using 4-etboxybenzoic acid without the addition of 1.0 M ethereal hydrogen chloride solution to give the titled product as a solid (0.1 g).

MS: ESI 437.14 (M+H).

¹H NMR: δ(DMSO) 8.22 (t, 1H), 7.79 (d, 2H), 7.49 (d, 1H), 7.25 (d, 1H), 7.00 (m, 3H), 4.5 (m, 1H), 4.07 (q, 2H), 3.37 (q, 2H), 2.73 (m, 2H), 2.47 (m, 2H), 2.30 (m, 2H), 1.91 (m, 2H), 1.60 (m, 2H), 1.34 (t, 3H).

Melting point: 118–20° C.

EXAMPLE 5

N-{2-[4-(3,4-Dichlorophenoxy)-1-piperidinyl]ethyl}-3-(trifluoromethoxy)benzamide hydrochloride

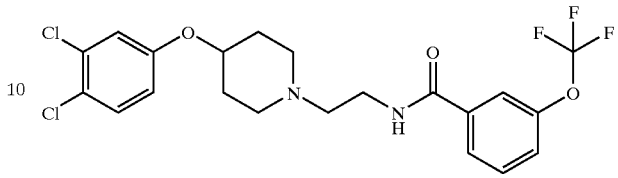

Prepared by the same method as Example 2 using 3-trifluoromethoxybenzoic acid to give the titled product as a solid (0.12 g).

MS: ESI 477.09 (M+H).

¹H NMR: δ(DMSO) 10.42 (bs, 1H), 9.11 (bm, 1H), 8.0 (d, 1H), 7.88 (s, 1H), 7.6 (m, 3H), 7.37 (m, 1H), 7.06 (m, 1H), 4.70 (m, 1H), 3.71 (m, 3H), 3.48 (d, 1H), 3.20 (m, 4H), 2.2 (m, 4H).

Melting point: 180–82° C.

EXAMPLE 6

N-{2-[4-(3,4-Dichlorophenoxy)-1-piperidinyl]ethyl}-4-methoxybenzamide

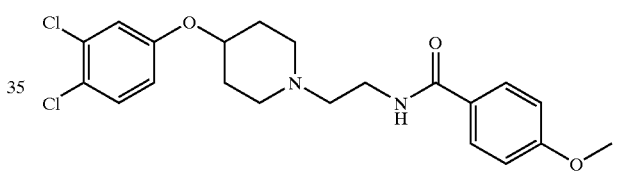

Prepared by the same method as Example 2 using 4-methoxybenzoic without the addition of 1.0 M ethereal hydrogen chloride solution to give the titled product as a solid (0.11 g).

MS: ESI 423.12 (M+H).

¹H NMR: δ(DMSO) 8.42 (t, 1H), 7.81 (m, 2H), 7.49 (d, 1H), 7.25 (d, 1H), 6.98 (s, 3H), 4.4 (m, 1H), 3.8 (s, 3H), 3.35 (q, 2H), 2.73 (m, 2H), 2.47 (m, 2H), 2.30 (m, 2H), 1.91 (m, 2H), 1.60 (m, 2H).

Melting point: 110–12° C.

EXAMPLE 7

N-{2-[4-(3,4-Dichlorophenoxy)-1-piperidinyl]ethyl}-4-(trifluoromethoxy)benzamide hydrochloride

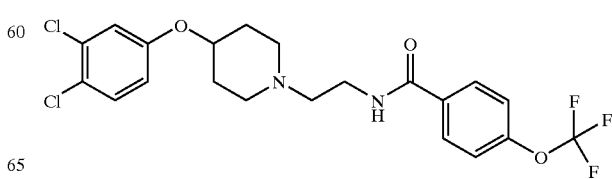

Prepared by the same method as Example 2 using 4-trifluoromethoxybenzoic acid to give the titled product as a solid (0.19 g).

MS: ESI 477 (M+H).

¹H NMR: δ(DMSO) 10.5 (bs, 1H), 9.06 (m, 1H), 8.07 (dd, 2H), 7.55 (t, 1H), 7.49 (d, 2H), 7.36 (dd, 1H), 7.10–7.02 (m, 1H), 4.72 (m, 1H), 3.70 (m, 3H), 3.47 (d, 1H), 3.14 (m, 2H), 2.25 (m, 2H), 2.02 (m, 2H).

Melting point: 184–187° C.

EXAMPLE 8

N-{2-[4-(3,4-Dichlorophenoxy)-1-piperidinyl]ethyl}-2-furamide hydrochloride

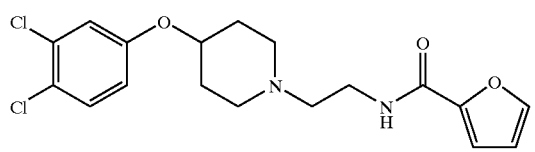

Prepared by the same method as Example 2 using furan-2-carboxylic acid to give the titled product as a solid (0.14 g).

MS: ESI 383.09 (M+H).

¹H NMR: δ(DMSO) 10.43 (bm, 1H), 8.76 (t, 1H), 7.87 (s, 1H), 7.55 (t, 1H), 7.36 (dd, 1H), 7.21 (d, 1H), 7.06 (m, 1H), 6.64 (dd, 1H), 4.83–4.61 (m, 1H), 3.65 (m, 3H), 3.45 (d, 1H), 3.08 (m, 4H), 2.1 (m, 4H).

Melting point: 225–28° C.

EXAMPLE 9

N-{2-[4-(3,4-Dichlorophenoxy)-1-piperidinyl]ethyl}-2-phenylacetamide hydrochloride

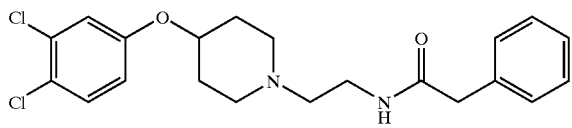

Prepared by the same method as Example 2 using phenylacetic acid to give the titled product as a solid (0.12 g).

MS: ESI 407 (M+H).

¹H NMR: δ(DMSO) 10.28 (bm, 1H), 8.46 (bm, 1H), 7.56 (t, 1H), 7.3 (m, 6H), 7.10 (m, 1H), 4.81/4.58 (m, 1H), 3.58 (d, 1H), 3.46 (m, 4H), 3.10 (m, 4H), 2.15 (m, 5H).

Melting point: 135–38° C.

EXAMPLE 10

N-{2-[4(3,4-Dichlorophenoxy)-1-piperidinyl]ethyl}-3-methoxybenzamide hydrochloride

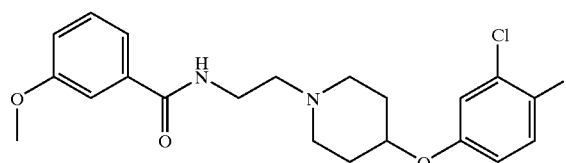

The product of Example 1 step (iv) (2.0 g) was dissolved in dichloromethane (490 ml), triethylamine (1.85 ml) and 3-methoxybenzoyl chloride (0.66 g) were added. After 72 hours at room temperature, water was added, the organic phase separated, dried and concentrated to a gum. The product was dissolved in dichloromethane and treated with 1.0M ethereal hydrogen chloride solution to give the titled product as a solid (0.88 g).

MS: ESI 423.12 (M+H).

¹H NMR: δ(DMSO) 10.6–10.5 (m, 1H), 9.92 (s, 1H), 7.54 (m, 3H), 7.38 (m, 2H), 7.08 (m, 2H), 4.84/4.62 (m 1H), 3.82 (s, 3H), 3.45 (m, 8H), 2.27 (m, 4H).

Melting point: 72–73° C.

EXAMPLE 11

3-Chloro-N-{2-[4-(3,4-dichlorophenoxy)-1-piperidinyl]ethyl}benzamide hydrochloride

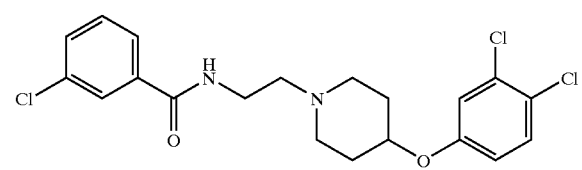

The product of Example 1 step (iv) (0.15 g) was dissolved in DMF (3 ml), N,N-di-isopropylethylamine (0.3 ml) and 3-chlorobenzoyl chloride (0.054 ml) were added. After 2 hours at room temperature, water and ethyl acetate were added, the organic phase separated dried and concentrated. The residue was purified by chromatography (dichloromethane:methanol, 95:5) to give an oil which was dissolved in ether and 1.0M ethereal hydrogen chloride solution added to give the titled product as a solid (0.12 g).

MS: ESI 427.07 (M+H).

¹H NMR: δ(DMSO) 8.42 (t, 1H), 7.94–7.84 (m, 2H), 7.49 (d, 1H), 7.29 (m, 3H), 6.98 (dd, 1H), 4.44 (m, 1H), 3.36 (m, 2H), 2.74 (m, 2H), 2.48 (m, 2H), 2.29 (bt, 2H), 1.92 (m, 2H), 1.60 (m, 2H).

Melting point: 118° C.

EXAMPLE 12

N-{2-[4-(3,4-Dichlorophenoxy)-1-piperidinyl]ethyl}-4-fluorobenzamide

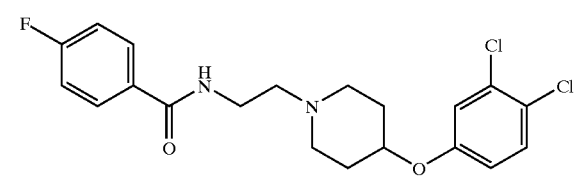

Prepared by the same method as Example 11 using 4-fluorobenzoyl chloride without the addition of 1.0 M ethereal hydrogen chloride solution to give the titled product as a solid (0.1 g).

MS: ESI 411.10 (M+H).

¹H NMR: δ(DMSO) 10.46 (bs, 1H), 9.04 (s, 1H), 7.98 (s, 1H), 7.90 (d, 1H), 7.58 (m, 3H), 7.36 (dd, 1H), 7.05 (m, 1H), 4.84/4.60 (m, 1H), 3.69 (m, 3H), 3.48 (bd, 1H), 3.20 (m, 4H), 2.15 (m, 4H).

Melting point: 192° C.

EXAMPLE 13

N-{2-[4-(3,4-Dichlorophenoxy)-1-piperidinyl]ethyl}-3-fluorobenzamide hydrochloride

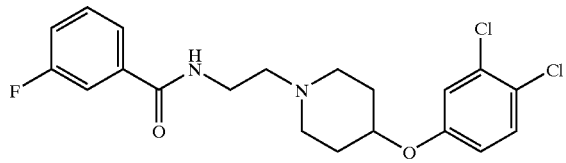

Prepared by the same method as Example 11 using 3-fluorobenzoyl chloride to give the titled product as a solid (0.09 g).

MS: ESI 411.10 (M+H).

$^1$H NMR: δ(DMSO) 10.67 (bs, 1H), 9.06 (s, 1H), 7.80 (m, 2H), 7.55 (m, 2H), 7.40 (m, 2H), 7.05 (m, 1H), 4.84/4.63 (m, 1H), 3.70 (m, 3H), 3.28 (m, 3H), 2.20 (m, 4H).

Melting point: 225° C.

EXAMPLE 14

N-{2-[4-(3,4-Dichlorophenoxy)-1-piperidinyl]ethyl}-3-hydroxybenzamide hydrochloride

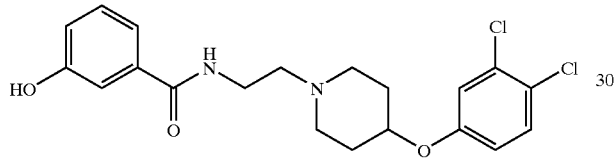

The product of Example 10 (0.15 g) was dissolved in dichloromethane (10 ml) and a solution of 1.0M BBr$_3$ in dichloromethane (4 ml) added. After 16 hours at room temperature the solvent was removed by evaporation, methanol was added and the solution concentrated. The residue was dissolved in 2M aqueous HCl solution, concentrated to dryness and the residue triturated under ether to give the titled product as a solid (0.1 g).

MS: ESI 409.10 (M+H).

$^1$H NMR: δ(DMSO) 9.98–9.4 (bs, 2H), 8.71 (t, 1H), 7.6 (dd, 1H), 7.4–7.2 (m, 4H), 7.05 (m, 1H), 6.95 (dd, 1H), 4.65 (m, 1H), 3.40 (m, 8H), 2.0 (m, 4H).

Melting point: 83–4° C.

EXAMPLE 15

N-{2-[4-(4-Chlorobenzoyl)-1-piperidinyl]ethyl}-3-[2-(methylamino)-2-oxoethoxy]benzamide hydrochloride

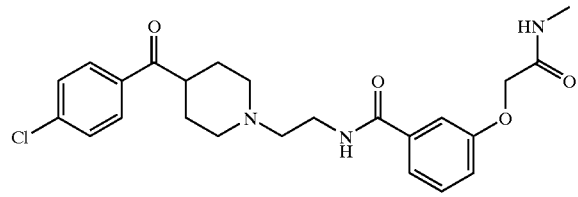

(i) [1-(2-Aminoethyl)-4-piperidinyl](4-chlorophenyl)methanone trifluoroacetate

To a solution of (4-chlorophenyl)(4-piperidinyl)methanone hydrochloride (2.5 g) and tert-butyl 2-bromoethylcarbamate (2.1 g) in DMF was added triethylamine (2.9 g), after 72 hours at room temperature water and ether were added. The organic phase was separated, dried and concentrated. The residue was dissolved in dichloromethane (40 ml), trifluoroacetic acid (10 ml) added and the solution left for 20 hours. Evaporation of the solvent gave a sticky solid which was triturated under ether to give the sub-titled product as a solid (2.5 g).

(ii) N-{2-[4-(4-Chlorobenzoyl)-1-piperidinyl]ethyl}-3-methoxybenzamide hydrochloride The product of step (i) (2.5 g) was dissolved in dichloromethane (20 ml), triethylamine (0.75 ml) and 3-methoxybenzoyl chloride (0.276 g) were added. After 16 hours, water was added, the organic phase separated, dried and concentrated to a gum. Purification by chromatography (ethyl acetate) gave a gum, which was treated with 1.0M ethereal hydrogen chloride solution to give the sub-titled product as a solid (0.3 g).

MS: ESI 401.16 (M+H).

$^1$H NMR: δ(DMSO) 10.3 (bm, 1H), 8.95 (t, 1H), 8.0 (m, 2H), 7.6 (m, 2H), 7.5 (m, 2H), 7.4 (t, 1H), 7.05 (m, 1H), 3.8 (s, 3H), 3.68 (m, 4H), 3.28 (m, 5H), 2.0 (m, 4H).

Melting point: 196–7° C.

(iii) N-{2-[4-(4-Chlorobenzoyl)-1-piperidinyl]ethyl}-3-hydroxybenzamide hydrochloride Prepared by the method of Example 14 using the product of step (ii) above (0.24 g) to give the sub-titled product as a solid (0.20 g).

MS: ESI 387.14 (M+H).

$^1$H NMR: δ(DMSO) 8.62 (t, 1H), 8.05 (dd, 2H), 7.6 (dd, 2H), 7.25 (m, 3H), 6.95 (m, 1H), 4.26 (m, 9H), 2.0 (m, 4H).

Melting point: 90–91° C.

(iv) N-{2-[4-(4-Chlorobenzoyl)-1-piperidinyl]ethyl}-3-[2-(methylamino)-2-oxoethoxy]benzamide hydrochloride The product of step (iii) above (0.10 g) was dissolved in DMF (3 ml), Cs$_2$CO$_2$ (0.23 g) and 2-chloro-N-methylacetamide (0.26 g) were added and the mixture heated at 80° C. for 16 hours. The mixture was cooled to room temperature, water and ethyl acetate were added and the organic phase separated. Evaporation of the solvent gave a gum which was treated with 1.0M ethereal hydrogen chloride solution to give the titled product as a solid (0.05 g).

MS: ESI 458.18 (M+H).

$^1$H NMR: δ(DMSO) 10.6–10.2 (bm, 1H), 8.95 (bm, 1H), 8.1 (m, 2H), 7.55 (m, 8H), 7.14 (bd, 1H), 4.54 (s, 2H), 4.0 (m, 1H), 3.4 (m, 8H), 2.65 (d, 3H), 2.0 (m, 4H).

Melting point: 69–70° C.

EXAMPLE 16

2-[3-{2-[4-(4-Fluorobenzoyl)-1-piperidinyl]ethyl}-2,4-dioxo-3,4-dihydro-1(2H)-quinazolinyl]-N,N-dimethylacetamide hydrochloride

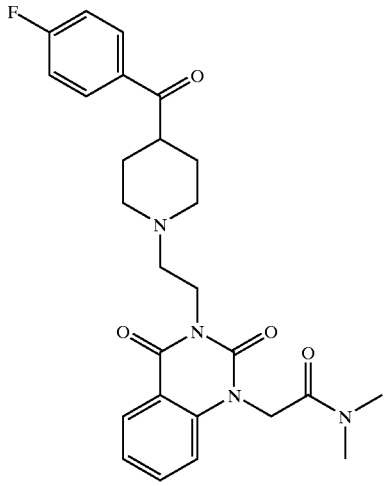

3-{2-[4-(4-Fluorobenzoyl)-1-piperidinyl]ethyl}-2,4(1H,3H)-quinazolinedio dissolved in DMF (5 ml) and NaH (60% dispersion in mineral oil) added. After 0.5 hours, 2-chloro-N,N-dimethylacetamide was added and the solution stirred at room temperature for 16 hours. Water and ethyl actetate were added, the organic phase separated, dried and concentrated to an oil. Purification by chromatography (dichloromethane:methanol 95:5) gave an oil which was treated with 1.0 M ethereal hydrogen chloride-solution to-give the titled product as a solid (0.15 g).

MS: ESI 481.22 (M+H).

$^1$H NMR: δ(DMSO) 8.08 (m, 3H), 7.76 (t, 1H), 7.40 (t, 2H), 7.32 (m, 2H), 5.05 (s, 2H), 4.36 (m, 1H), 3.76 (m, 3H), 3.39 (m, 2H), 3.15 (s, 3H), 2.87 (s, 3H), 2.02 (m, 2H), 1.81 (m, 2H), 1.28 (m, 2H).

Melting point: 245–246° C.

EXAMPLE 17

N-{2-[4-(3,4-Dichlorobenzoyl)-1-piperazinyl]ethyl}-3-methoxybenzamide hydrochloride

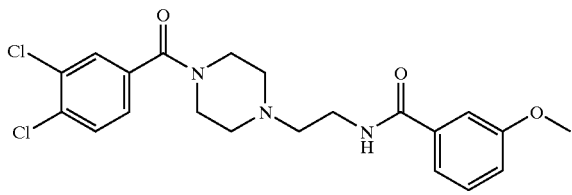

(i) tert-Butyl 2-(1-piperazinyl)ethylcarbamate

A mixture of benzaldehyde (21 g) and 1-(2-aminoethyl)piperazine (25.8 g) was stirred and heated under a Dean and Stark water separator for 20 hours. The cooled solution was treated portionwise with di-tert-butyldicarbonate (48 g), stirred for 72 hours and concentrated. The residue was treated with 1M aqueous KHSO$_4$ solution (220 ml), stirred for 24 hours, ether was added and the organic phase separated. The aqueous phase was treated with 2M NaOH solution, dichloromethane was added and the organic phase separated. The combined organic phase was washed with brine, dried and concentrated to give the sub-titled product as an oil (30 g).

MS: APCI(+ve) 230 (M+H).

$^1$H NMR δ(CDCl$_3$) 3.43 (t, 4H), 2.8 (t, 2H), 2.45 (m, 6H), 1.5 (s, 9H).

(ii) tert-Butyl 2-[4-(3,4-dichlorobenzoyl)-1-piperazinyl]ethylcarbamate

The product from step (i) above (3 g) was dissolved in pyridine (12 ml), 3,4-dichlorobenzoyl chloride (2.05 g) was added and the mixture stirred at room temperature for 18 hours. A solid was collected by filtration and purified by chromatography (dichloromethane:methanol: 0.880 NH$_4$OH, 90:9:1) to give the sub-titled product as an oil (3.59 g).

MS: APCI(+ve) 364 (M+H).

$^1$H NMR δ(CDCl$_3$) 7.33 (m, 3H), 7.04 (m, 1H), 6.76 (bs, 1H), 3.86 (s, 3H), 3.55 (q, 2H), 3.45 (t, 4H), 2.61 (t, 3H), 2.46 (t, 4H), 1.46 (s, 9H).

(iii) [4-(2-Aminoethyl)-1-piperazinyl](3,4-dichlorophenyl)methanone trifluoroacetate The product from step (ii) above (3.3 g) was dissolved in dichloromethane (50 ml) and trifluoroacetic acid (10 ml) added. After 16 hours at room temperature the solvent was removed to give the sub-titled product as an oil (5.9 g).

MS: APCI(+ve) 264 (M+H).

(iv) N-{2-[4-(3,4-Dichlorobenzoyl)-1-piperazinyl]ethyl}-3-methoxybenzamide hydrochloride The product from step (iii) above (0.15 g) was dissolved in pyridine (2 ml) and 3-methoxybenzoyl chloride (0.064 g) added. After 16 hours at room temperature, water and ethyl acetate were added, the organic phase separated, dried and concentrated to an oil. Purification by chromatography (dichloromethane:methanol, 95:5) gave an oil which was treated with 1.0M ethereal hydrogen chloride solution to give the titled product as a solid (0.043 g).

MS: ESI 436.12 (M+H).

$^1$H NMR: δ(DMSO) 8.8 (bt, 1H), 7.34 (m, 2H), 7.43 (m, 4H), 7.14 (m, 1H), 3.82 (s, 3H), 3.48 (m, 12H).

Melting point: 230° C.

EXAMPLE 18

3,4-Dichloro-N-{2-[4-(3,4-dichlorobenzoyl)-1-piperazinyl]ethyl}benzamide

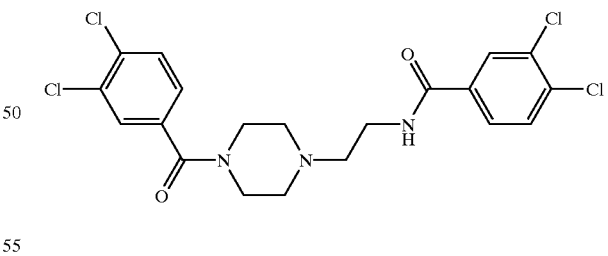

A solution of benzaldehyde (5.3 g) and 1-(2-aminopiperazine) (6.45 g) in toluene (100 ml) was heated under a Dean and Stark water separator for 4 hours. The solution was cooled to room temperature and triethylamine (5.05 g) added. A solution of 3,4-dichlorobenzoyl chloride (10.48 g) in toluene (50 ml) was added dropwise, the solution stirred at room temperature for 18 hours and water added. The organic phase was separated, dried and concentrated to a residue which was treated with 1N aqueous KHSO$_4$ solution (65 ml). The mixture was stirred vigorously for 4 hours, ether was added, the aqueous phase separated and NaOH added. CHCl$_3$ was added, the organic phase separated, dried and concentrated to a gum. Purification by chromatography (dichloromethane:triethylamine, 95:5) gave the titled product as a foam (0.25 g).

MS: ESI 474.03 (M+H).

$^1$H NMR: δ(DMSO) 8.8 (bt, 1H), 7.34 (m, 2H), 7.43 (m, 4H), 7.14 (m, 1H), 3.82 (s, 3H), 3.48 (m, 12H).

EXAMPLE 19

4-Chloro-N-{2-[4-(3,4-dichlorobenzoyl)-1-piperazinyl]ethyl}-2-[2-(dimethylamino)-2-oxoethoxy]benzamide hydrochloride

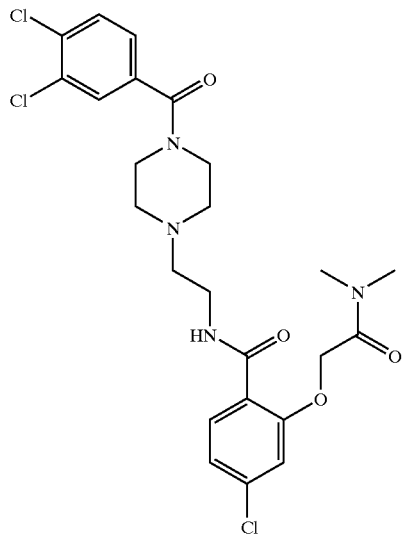

The product of Example 26 step (ii) (0.3 g), 3,4-dichlorobenzoyl chloride (0.1 g) and triethylamine (0.15 g) were dissolved in dichloromethane (15 ml). After 20 hours at room temperature water was added, the organic phase separated, dried and evaporated to give a gum. Purification by chromatography (dichloromethane:methanol, 20:1) gave a solid which was treated with 1.0M ethereal hydrogen chloride solution to give the titled product as a solid (0.1 g).

MS: ESI 541.11 (M+H).

$^1$H NMR δ(DMSO-D6) 9.54 (t, 1H), 7.91 (d, 1H), 7.74 (m, 2H), 7.43 (m, 2H), 7.18 (d, 1H), 5.12 (s, 2H), 3.2–3.8 (m, 12H), 2.99 (s, 3H), 2.88 (s, 3H).

Melting point: 226–7° C.

EXAMPLE 20

N~7~-{2-[4-(3,4-Dichlorophenoxy)-1-piperidinyl]ethyl}-5-methyl[1,3]thiazolo[4,5-d]pyrimidine-2,7-diamine

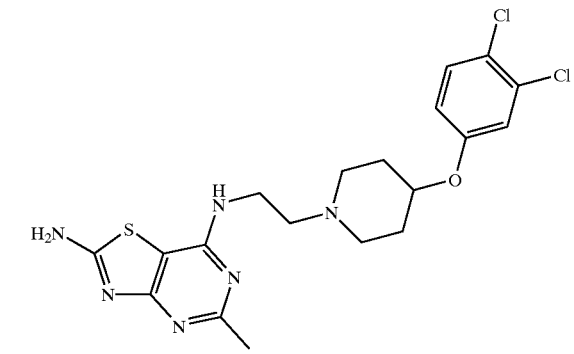

MS: APCI(+ve) 453 (M+1).

EXAMPLE 21

N-{2-[4-(3,4-Dichlorophenoxy)-1-piperidinyl]ethyl}-9-methyl-9H-purin-6-amine

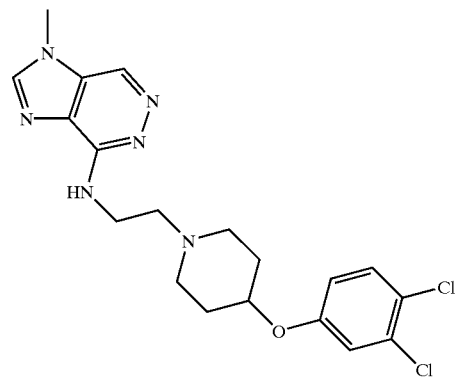

MS: APCI(+ve) 421 (M+1).

EXAMPLE 22

N-{2-[4-(3,4-Dichlorophenoxy)-1-piperidinyl]ethyl}-1,3-benzothiazol-2-amine

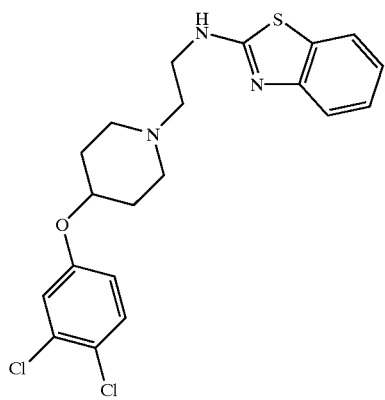

MS: APCI(+ve) 422 (M+1).

EXAMPLE 23

N-{2-[4-(3,4-Dichlorophenoxy)-1-piperidinyl]ethyl}-1,3-benzoxazol-2-amine

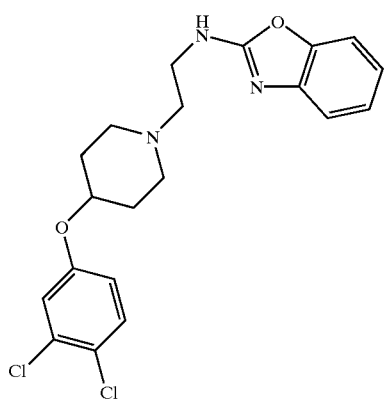

MS: APCI(+ve) 406 (M+1).

EXAMPLE 24

6-Chloro-N-{2-[4-(3,4-dichlorophenoxy)-1-piperidinyl]ethyl}-2-pyrazinamine

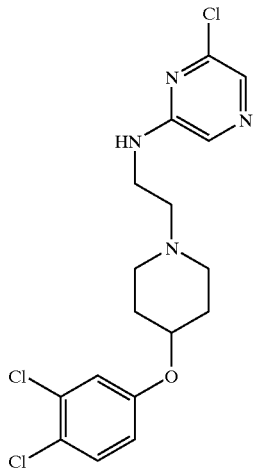

MS: APCI(+ve) 403 (M+1).

EXAMPLE 25

6-Chloro-N-{2-[4-(3,4-dichlorophenoxy)-1-piperidinyl]ethyl}-3-pyridazinamine

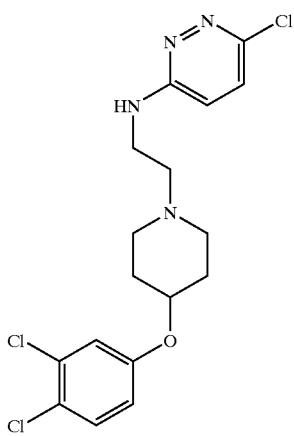

MS: APCI(+ve) 403 (M+1).

EXAMPLE 26

6-({2-[4-(3,4-Dichlorophenoxy)-1-piperidinyl]ethyl}amino)-1,3-dimethyl-2,4(1H,3H)-pyrimidinedione

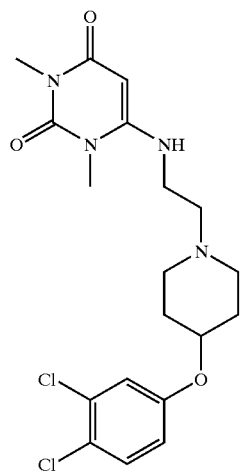

MS: APCI(+ve) 427 (M+1).

EXAMPLE 27

N-{1-[4-(3,4-Dichlorophenoxy)-piperidin-1-ylmethyl]-2-methyl-propyl}-4-methyl-benzamide, hydrochloride

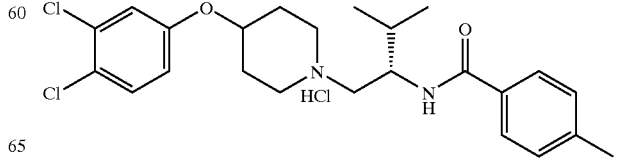

(i) N-{1-{4-(3,4-Dichlorophenoxy)-piperidine-1-carbonyl]-2-methyl-propyl}-acetamide N-Boc Valine (1.13 g) was dissolved in dichloromethane (5 ml) and EDC (0.99 g) added, after 5 min the product according to Example 1 step (ii) (1.44 g) in dichloromethane (5 ml) was added in one portion. After 3 hours at room temperature, aqueous sodium bicarbonate solution and ethyl acetate were added. The organic phase was separated and the solvent removed to give the sub-titled compound as an oil (1.57 g) which was used in the next step without further purification.

(ii) 2-amino-1-[4-(3,4-dichlorophenoxy)-piperidin-1-yl]-3-methyl-butan-1-one

The product of step (i) (1.57 g) was dissolved in dichloromethane (14 ml) and trifluoroacetic acid (4 ml) added. After 2 hours at room temperature the solvent was removed, ethyl acetate and 2N aqueous NaOH solution were added to give pH 8.0. The organic phase was separated and concentrated to give the sub-titled product as an oil (1.24 g) which was used in the next step without further purification.

(iii) 1-[4-(3,4-Dichlorophenoxy)-piperidin-1-ylmethyl]-2-methyl-propylamine

The product of step (ii) (1.12 g) was dissolved in THF (10 ml) and Borane/THF complex (22.7 ml) added. The mixture was heated under reflux for 2 hours and cooled. The solvent was evaporated, the product dissolved in methanol (5 ml) and 50% aqueous HCl solution added. The mixture was heated to 70° C. for 1 hour and cooled to room temperature. The solvent was removed, ethyl acetate and 2N aqueous NaOH solution were added to give pH 9.0. The organic phase was separated and the solvent evaporated to give the sub-titled compound as an oil (0.98 g) which used without further purification.

(iv) N-{1-[4-(3,4-Dichlorophenoxy)-piperidin-1-ylmethyl]-2-methyl-propyl}-4-methyl-benzamide, hydrochloride The product of step (iii) (0.2 g) was dissolved in dichloromethane (5 ml), triethylamine (0.126 ml) and 4-methylbenzoyl chloride (0.097 ml) were added. After 2 hours at room temperature, ethyl acetate and aqueous NaHCO₃ solution were added, the organic phase separated and the solvent removed to leave an oil. Purification by reverse phase HPLC (with a gradient eluent system (25% MeCN/NH₄OAc$_{aq}$ (0.1%) to 95% MeCN//NH₄OAc$_{aq}$ (0.1%)) gave a gum. Addition of 1.0M ethereal hydrogen chloride solution gave the titled product as a solid (0.104 g).

Melting point: 131–132° C.
MS: ESI 450 (M+H).
¹H NMR: δ(DMSO) 8.45 (t, 1H), 7.00–7.90 (m, 7H), 4.79 (br s, 1H), 4.24–4.30 (m, 1H), 3.10–3.42 (m, 5H), 2.36 (s, 3H), 1.88–2.40 (m, 5H), 0.92 (t, 6H).

EXAMPLE 28

N-{1-[4-(3,4-Dichloro-phenoxy)-piperidin-1-ylmethyl]-2-methyl-propyl}-3-methoxy-benzamide, hydrochloride

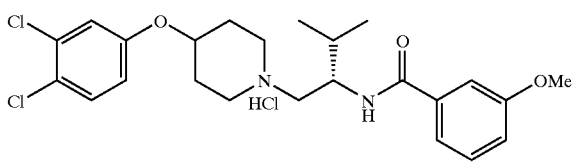

The product according to Example 27 step (iii) dissolved in dichloromethane (4 ml), triethylamine (0.090 ml) and 3-methoxybenzoyl chloride (0.077 ml) were added. After 2 hours at room temperature, NaHCO₃ was added, the product extracted with ethyl acetate, the combined organic extracts dried with Na₂SO₄ and concentrated. Purification with reverse phase HPLC (with a gradient eluent system (25% MeCN/NH₄OAc$_{aq}$ (0.1%) to 95% MeCN//NH₄OAc$_{aq}$ (0.1%)) gave a gum. The product was dissolved in methanol and treated with 1.0M ethereal Hydrogen chloride solution to give the product as a solid (0.045 g).

MS: ESI 465 (M+H).
¹H NMR: δ(DMSO) 8.58–8.63 (m, 1H), 7.01–7.58 (m, 6H), 4.80 (br s, 1H), 4.23–4.59 (m, 1H), 3.83 (s, 3H), 3.04–3.60 (m, 4H), 1.89–2.14 (m, 5H), 0.85 (m, 6H).

EXAMPLE 29

N-{2-[4-(3,4-Dichloroanilino)-1-piperidinyl]ethyl}-3-methoxybenzamide dihydrochloride

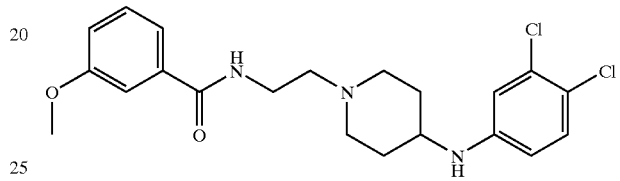

(i) tert-Butyl 4-(3,4-dichloroanilino)-1-piperidinecarboxylate

A solution of 3,4-dichloroaniline (5 g), N-tert-butoxycarbonyl-4-piperidone (11.7 g), sodium triacetoxyborohydride (19.7 g) and acetic acid (7 ml) in dichloroethane (150 ml) was stirred for 16 hours. 2M NaOH solution and ether were added, the organic phase separated, dried and concentrated. The residue was triturated under an isohexane:ethyl acetate, 4:1 mixture and the sub-titled product collected as a solid (7.25 g).

MS: APCI(+ve) 345 (M+H).
¹H NMR: δ(DMSO) 7.23 (d, 1H), 6.77 (d, 1H), 6.57 (dd, 1H), 5.99 (d, 1H), 3.85 (bd, 2H), 3.40 (m, 1H), 2.90 (bm, 2H), 1.85 (m, 2H), 1.39 (s, 9H), 1.19 (m, 2H).

(ii) N-(3,4-Dichlorophenyl)-4-piperidinamine trifluoroacetate

The product of step (i) above (6.5 g) was dissolved in dichloromethane (75 ml) and trifluoroacetic acid (25 ml) added. After 72 hours at room temperature the solution was evaporated and the residue triturated under ether to give the sub-titled product as a solid (6.3 g).

MS: APCI(+ve) 245/7 (M+H).
¹H NMR: δ(DMSO) 8.65 (bs, 1H), 8.50 (bs, 1H), 7.26 (d, 1H), 6.81 (d, 1H), 6.60 (dd, 1H), 6.19 (bs, 1H), 3.53 (bs, 1H), 3.30 (m, 2H), 3.0 (m, 2H), 202 (m, 2H), 1.50 (m, 2H).

(iii) tert-Butyl 2-[4-(3,4-dichloroanilino)-1-piperidinyl]ethylcarbamate

The product from step (ii) above (2.0 g), N-tert-butoxycarbonyl-2-bromoethanamine (1.0 g) and N,N-diisopropylethylamine (3.7 ml) were dissolved in DMF (25 ml) and stirred for 16 hours. Water and ethyl acetate were added, the organic phase separated, dried and evaporated to give a gum. Purification by chromatography (dichloromethane:methanol, 95:5) gave the sub-titled product as a solid (1.25 g).

MS: APCI(+ve) 388/90 (M+H).
¹H NMR: δ(DMSO) 7.22 (d, 1H), 6.73 (d, 1H), 6.62 (t, 1H), 6.54 (dd, 1H) 5.94 (d, 1H), 3.17 (m, 1H), 3.02 (m, 2H), 2.77 (bd, 2H), 2.31 (t, 3H), 2.06 (t, 2H), 1.84 (bd, 2H), 1.35 (m, 11H).

(iv) 1-(2-Aminoethyl)-N-(3,4-dichlorophenyl)-4-piperidinamine triluoroacetate

The product from step (iii) above (1.2 g) was dissolved in dichloromethane (30 ml) and trifluoroacetic acid (10 ml) added. After 72 hours at room temperature the reaction mixture was evaporated and residue triturated under ether to give the sub-titled product as a solid (1.6 g).

MS: APCI(+ve) 288/90 (M+H).

(v) N-{2-[4-(3,4-Dichloroanilino)-1-piperidinyl]ethyl}-3-methoxybenzamide dihydrochloride The product of step (iv) above (0.5 g) and triethylamine (1.1 ml) were dissolved in DMF (10 ml), 3-methoxybenzoylchloride (0.11 ml) was added dropwise. After 2 hours, water and ethyl acetate were added, the organic phase separated, dried and evaporated. Purification of the residue by chromatography (dichloromethane:methanol, 95:5) gave an oil which was treated with 1.0M ethereal hydrogen chloride solution to give the titled product as a solid (0.15 g).

MS: ESI 422.14 (M+H).

$^1$H NMR: δ(DMSO) 10.44 (bs, 1H), 8.93 (t, 1H) 7.51 (m, 2H), 7.40 (t, 1H), 7.26 (d, 1H), 7.11 (dd, 1H), 6.81 (d, 1H), 6.60 (dd, 1H), 3.82 (s, 3H), 2.68 (m, 4H), 3.25 (m, 5H), 2.09 (bd, 2H), 1.76 (m, 2H).

Melting point: 170° C.

EXAMPLE 30

N-{2-[4-(3,4-Dichlorophenoxy)-1-piperidinyl]ethyl}-N-(3-methoxybenzyl)amine dihydrochloride

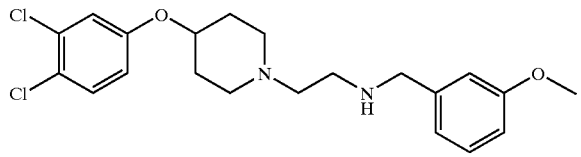

A suspension of the product of Example 1 step (iv) (0.11 g) in a mixture of DMF (1.5 ml) and 1,2-dichloroethane (3 ml) was stirred under an atmosphere of nitrogen. Sodium triacetoxyborohydride (0.097 g), 3-methoxybenzaldehyde (0.041 g) and triethylamine (0.046 g) were added and the mixture stirred for 18 hours at room temperature. Chloroform and aqueous NaHCO$_3$ solution were added, the organic phase separated, dried and concentrated to a gum. Purification by chromatography (chloroform:triethylamine:methanol, 89:10:1) gave an oil which was treated with 1.0M ethereal hydrogen chloride solution to give the titled product as a solid (0.067 g).

MS: ESI 409.14 (M+H).

$^1$H NMR: δ(DMSO) 7.50 (d, 1H), 7.30 (m, 3H), 7.12 (d, 1H), 7.03 (dd, 1H), 6.97 (dd, 1H), 4.71 (bm, 1H), 4.18 (s, 2H), 3.80 (s, 3H), 3.45 (bm, 4H), 2.23 (m, 6H), 2.04 (m, 2H),

Melting point: 247–51° C.

EXAMPLE 31

3-{2-[4-(3,4-Dichlorophenoxy)-1-piperidinyl]ethyl}-6-methoxy-2,4(1H,3H)-quinazolinedione

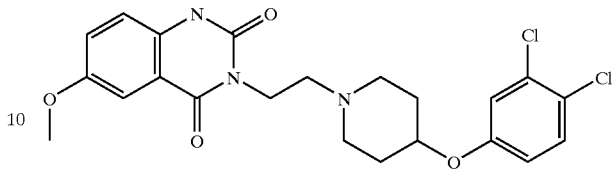

(i) 2-Amino-N-{2-[4-(3,4-dichlorophenoxy)-1-piperidinyl]ethyl}-5-methoxybenzamide Prepared by the method of Example 2 using the product from Example 1 step (iv) (1.0 g) and 2-amino-5-methoxybenzoic acid (0.418 g) without the addition of 1.0M ethereal hydrogen chloride solution to give an oil which was purified by chromatography (dichloromethane:methanol, 95:5) to give the sub-titled product as an oil (0.82 g).

MS: APCI(+ve) 438 (M+H).

(ii) 3-{2-[4-(3,4-Dichlorophenoxy)-1-piperidinyl]ethyl}-6-methoxy-2,4(1H,3H)-quinazolinedione The product of step (i) above was dissolved in toluene (10 ml). A solution of phosgene 2.0 M in toluene (10 ml) was added, the solution heated under reflux for 1 hour and cooled. Ethyl acetate and aqueous NaHCO$_3$ solution were added, the organic phase separated, dried and concentrated to leave a residue which was purified by chromatography (dichloromethane:methanol, 95:5). The titled product was obtained as a solid (0.11 g).

MS: ESI 464.11 (M+H).

$^1$H NMR: δ(DMSO) 7.49 (dd, 1H), 7.36 (d, 1H), 7.30 (dd, 1H), 7.24 (d, 1H), 6.98 (dd, 1H), 4.44 (m, 1H), 4.03 (t, 3H), 3.80 (s, 3H), 2.76 (m, 2H), 2.32 (m, 2H), 1.89 (m, 2H), 1.57 (m, 2H).

Melting point: 190° C.

The compounds of following Examples 32 to 125 were prepared by methods analogous to the method of Example 10.

EXAMPLE 32

N-{2-[4-(3,4-Dichlorophenoxy)-1-piperidinyl]ethyl}-3-fluorobenzamide

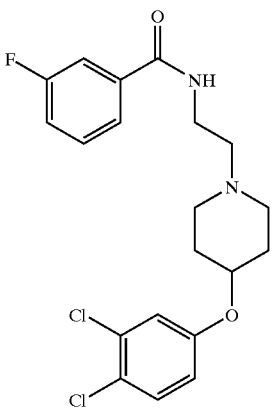

MS: APCl (+ve) BP 411.

EXAMPLE 33
N-{2-[4-(3,4-Dichlorophenoxy)-1-piperidinyl]ethyl}benzamide
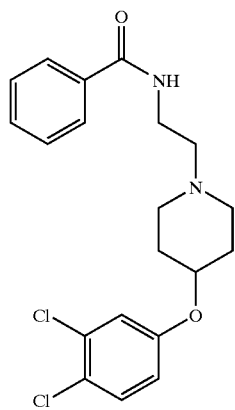
MS: APC1 (+ve) BP 393.
EXAMPLE 34
4-Chloro-N-{2-[4-(3,4-dichlorophenoxy)-1-piperidinyl]ethyl}benzamide
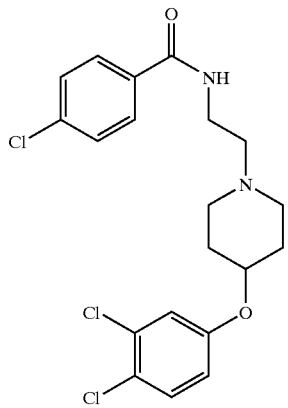
MS: APC1 (+ve) BP 429.
EXAMPLE 35
N-{2-[4-(3,4-Dichlorophenoxy)-1-piperidinyl]ethyl}-4-methoxybenzamide
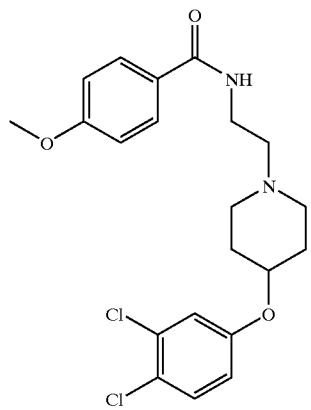
MS: APC1 (+ve) BP 423.
EXAMPLE 36
N-{2-[4-(3,4-Dichlorophenoxy)-1-piperidinyl]ethyl}-2-methoxybenzamide
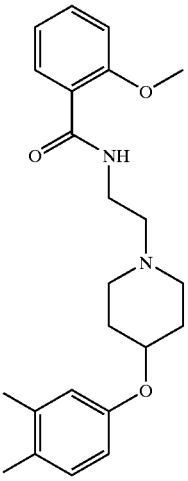
MS: APC1 (+ve) BP 423.

EXAMPLE 37

N-{2-[4-(3,4-Dichlorophenoxy)-1-piperidinyl]ethyl}-3-methoxybenzamide

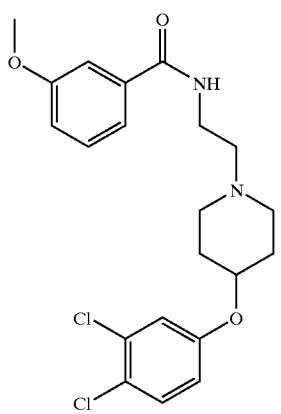

MS: APCl (+ve) BP 423.

EXAMPLE 38

N-{2-[4-(3,4-Dichlorophenoxy)-1-piperidinyl]ethyl}-2-nitrobenzamide

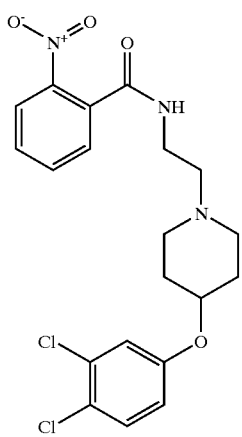

MS: APCl (+ve) BP 438.

EXAMPLE 39

N-{2-[4-(3,4-Dichlorophenoxy)-1-piperidinyl]ethyl}-2-methylbenzamide

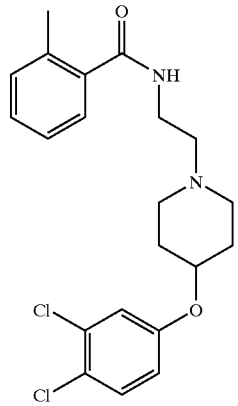

MS: APCl (+ve) BP 407.

EXAMPLE 40

N-{2-[4-(3,4-Dichlorophenoxy)-1-piperidinyl]ethyl}-3-(trifluoromethyl)benzamide

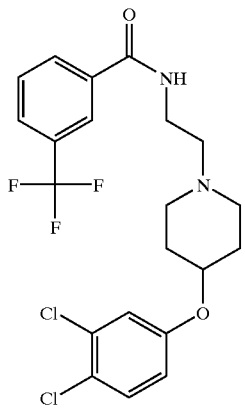

MS: APCl (+ve) BP 461.

EXAMPLE 41

N-{2-[4-(3,4-Dichlorophenoxy)-1-piperidinyl]ethyl}-3,5-dinitrobenzamide

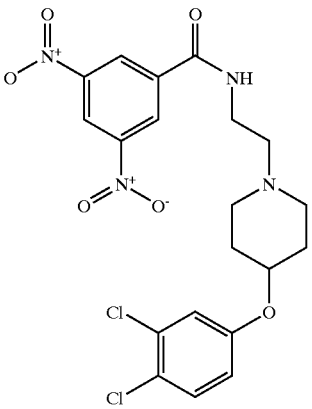

MS: APCl (+ve) BP 483.

EXAMPLE 42

N-{2-[4-(3,4-Dichlorophenoxy)-1-piperidinyl]ethyl}-2-iodobenzamide

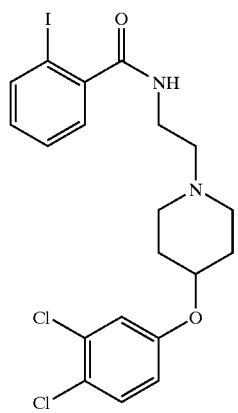

MS: APC1 (+ve) BP 519.

EXAMPLE 43

4-Cyano-N-{2-[4-(3,4-dichlorophenoxy)-1-piperidinyl]ethyl}benzamide

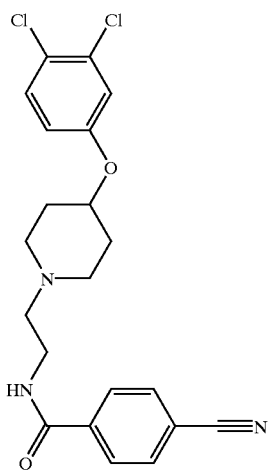

MS: APC1 (+ve) BP 418.

EXAMPLE 44

4-Bromo-N-{2-[4-(3,4-dichlorophenoxy)-1-piperidinyl]ethyl}benzamide

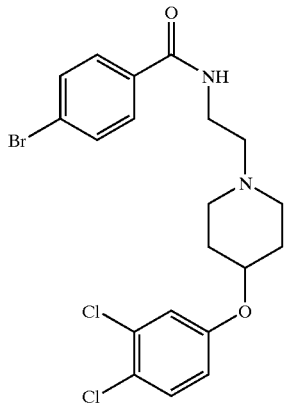

MS: APC1 (+ve) BP 473.

EXAMPLE 45

N-{2-[4-(3,4-Dichlorophenoxy)-1-piperidinyl]ethyl}-4-methylbenzamide

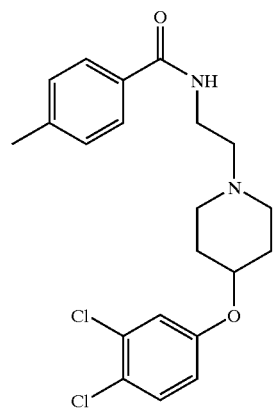

MS: APC1 (+ve) BP 407.

EXAMPLE 46

N-{2-[4-(3,4-Dichlorophenoxy)-1-piperidinyl]ethyl}-4-nitrobenzamide

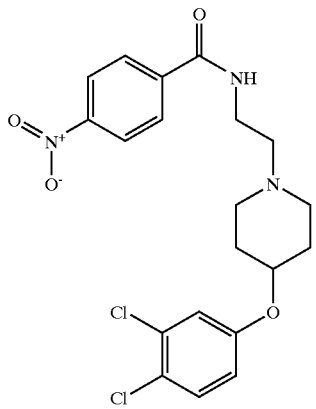

MS: APC1 (+ve) BP 438.

EXAMPLE 47
3-Bromo-N-{2-[4-(3,4-dichlorophenoxy)-1-piperidinyl]ethyl}benzamide
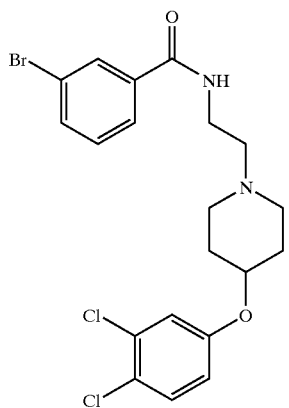
MS: APC1 (+ve) BP 473.
EXAMPLE 48
3,4-Dichloro-N-{2-[4-(3,4-dichlorophenoxy)-1-piperidinyl]ethyl}benzamide
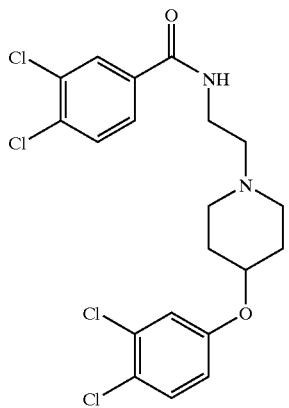
MS: APC1 (+ve) BP 463.
EXAMPLE 49
N-{2-[4-(3,4-Dichlorophenoxy)-1-piperidinyl]ethyl}-4-fluorobenzamide
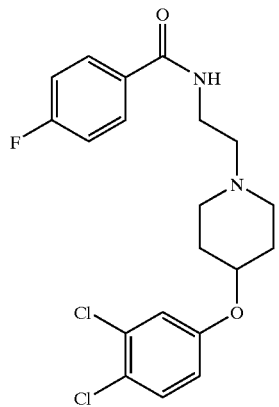
MS: APC1 (+ve) BP 411.
EXAMPLE 50
2,4-Dichloro-N-{2-[4-(3,4-dichlorophenoxy)-1-piperidinyl]ethyl}benzamide
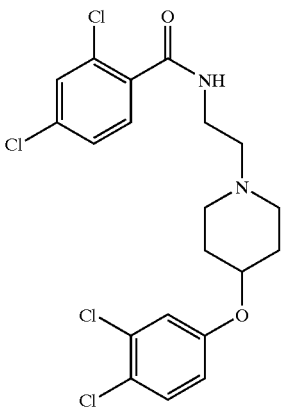
MS: APC1 (+ve) BP 463.

EXAMPLE 51
N-{2-[4-(3,4-Dichlorophenoxy)-1-piperidinyl]ethyl}-3-methylbenzamide
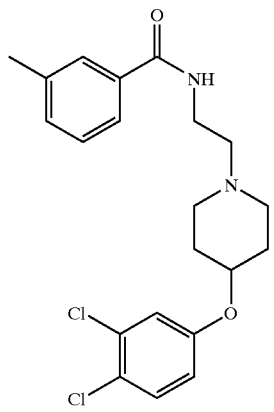
MS: APC1 (+ve) BP 407.
EXAMPLE 52
N-{2-[4-(3,4-Dichlorophenoxy)-1-piperidinyl]ethyl}-4-iodobenzamide
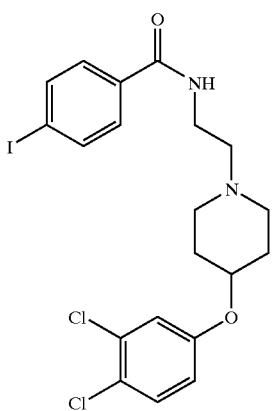
MS: APC1 (+ve) BP 519.
EXAMPLE 53
4-Chloro-N-{2-[4-(3,4-dichlorophenoxy)-1-piperidinyl]ethyl}-3-nitrobenzamide
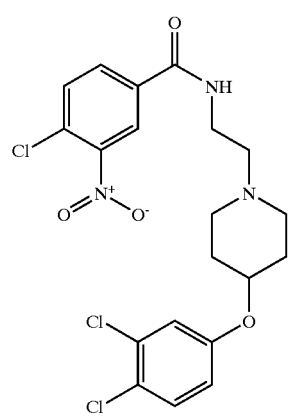
MS: APC1 (+ve) BP 472.
EXAMPLE 54
N-{2-[4-(3,4-Dichlorophenoxy)-1-piperidinyl]ethyl}-4-methyl-3-nitrobenzamide
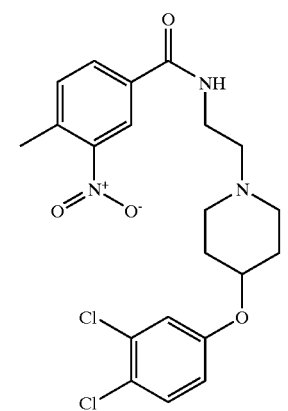
MS: APC1 (+ve) BP 452.

EXAMPLE 55

N-{2-[4-(3,4-Dichlorophenoxy)-1-piperidinyl]ethyl}-2-fluoro-5-(trifluoromethyl)benzamide

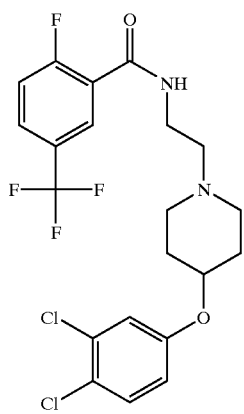

MS: APC1 (+ve) BP 479.

EXAMPLE 56

N-{2-[4-(3,4-Dichlorophenoxy)-1-piperidinyl]ethyl}-3-(trifluoromethoxy)benzamide

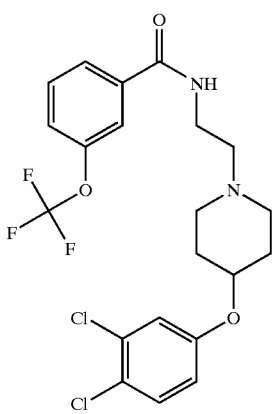

MS: APC1 (+ve) BP 477.

EXAMPLE 57
3,5-Dichloro-N-{2-[4-(3,4-dichlorophenoxy)-1-piperidinyl]ethyl}benzamide

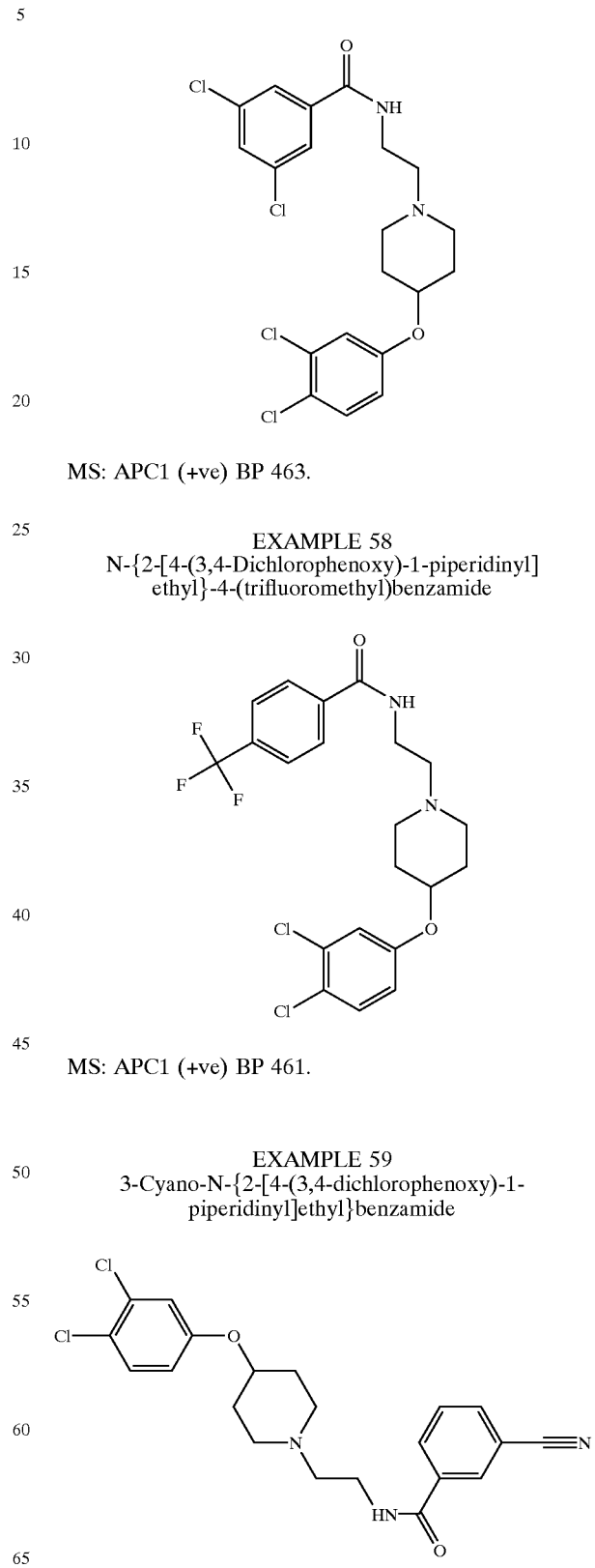

MS: APC1 (+ve) BP 463.

EXAMPLE 58
N-{2-[4-(3,4-Dichlorophenoxy)-1-piperidinyl]ethyl}-4-(trifluoromethyl)benzamide MS: APC1 (+ve) BP 461.

EXAMPLE 59
3-Cyano-N-{2-[4-(3,4-dichlorophenoxy)-1-piperidinyl]ethyl}benzamide MS: APC1 (+ve) BP 418.

EXAMPLE 60

2-Bromo-N-{2-[4-(3,4-dichlorophenoxy)-1-piperidinyl]ethyl}-5-methoxybenzamide

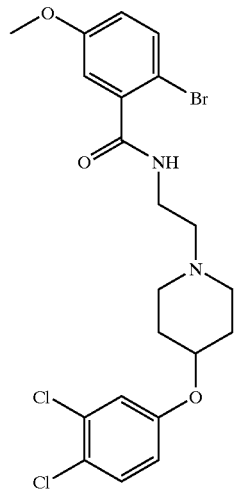

MS: APC1 (+ve) BP 503.

EXAMPLE 61

N-{2-[4-(3,4-Dichlorophenoxy)-1-piperidinyl]ethyl}-2-furamide

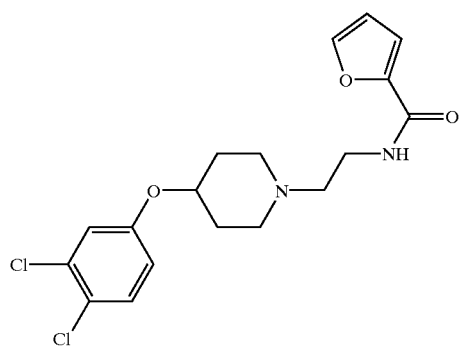

MS: APC1 (+ve) BP 383.

EXAMPLE 62

3-Chloro-N-{2-[4-(3,4-dichlorophenoxy)-1-piperidinyl]ethyl}benzamide

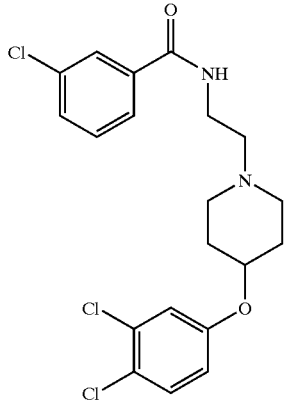

MS: APC1 (+ve) BP 427.

EXAMPLE 63

2-Chloro-N-{2-[4-(3,4-dichlorophenoxy)-1-piperidinyl]ethyl}benzamide

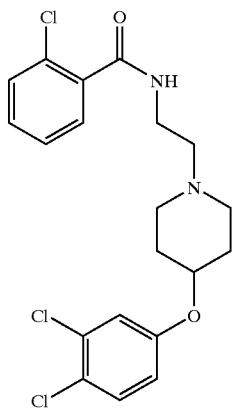

MS: APC1 (+ve) BP 429.

EXAMPLE 64

N-{2-[4-(3,4-Dichlorophenoxy)-1-piperidinyl]ethyl}-3,5-difluorobenzamide

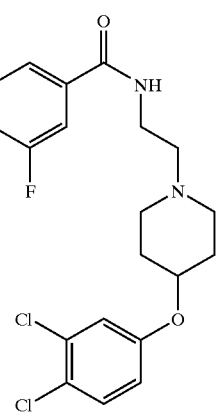

MS: APC1 (+ve) BP 429.

EXAMPLE 65
2,3-Dichloro-N-{2-[4-(3,4-dichlorophenoxy)-1-piperidinyl]ethyl}benzamide
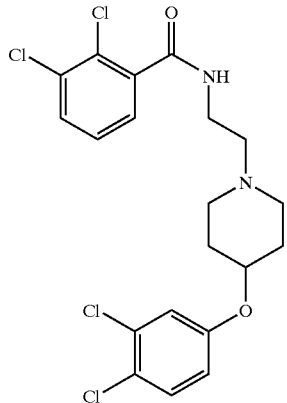
MS: APC1 (+ve) BP 463.
EXAMPLE 66
N-{2-[4-(3,4-Dichlorophenoxy)-1-piperidinyl]ethyl}-2-naphthamide
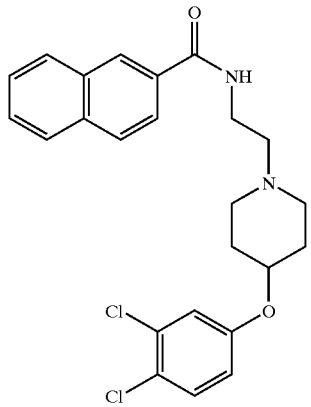
MS: APC1 (+ve) BP 442.
EXAMPLE 67
N-{2-[4-(3,4-Dichlorophenoxy)-1-piperidinyl]ethyl}-2-(methylsulfanyl)nicotinamide
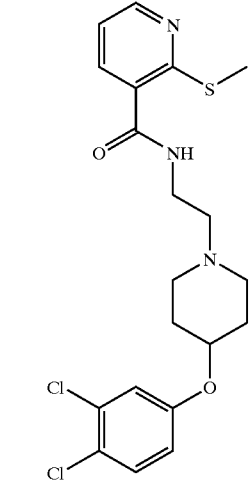
MS: APC1 (+ve) BP 440.
EXAMPLE 68
N-{2-[4-(3,4-Dichlorophenoxy)-1-piperidinyl]ethyl}-2-fluoro-6-(trifluoromethyl)benzamide
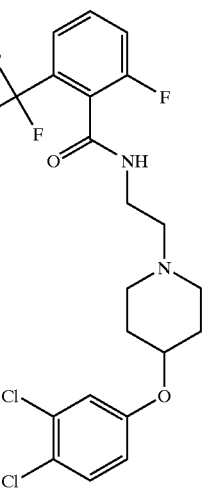
MS: APC1 (+ve) BP 479.

EXAMPLE 69
N-{2-[4-(3,4-Dichlorophenoxy)-1-piperidinyl]ethyl}-2,4-difluorobenzamide
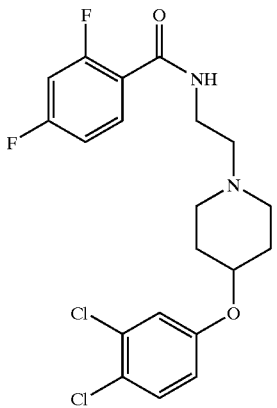
MS: APC1 (+ve) BP 429.
EXAMPLE 70
N-{2-[4-(3,4-Dichlorophenoxy)-1-piperidinyl]ethyl}-2-thiophenecarboxamide
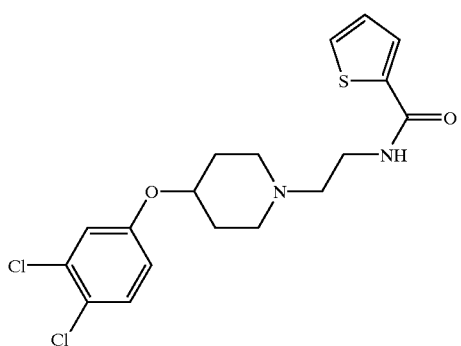
MS: APC1 (+ve) BP 399.
EXAMPLE 71
N-{2-[4-(3,4-Dichlorophenoxy)-1-piperidinyl]ethyl}-2-quinoxalinecarboxamide
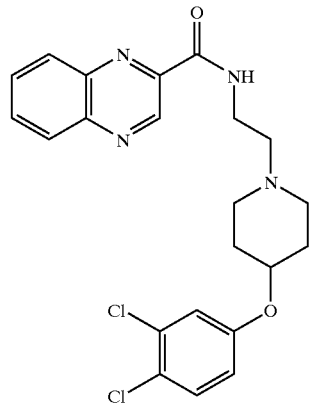
MS: APC1 (+ve) BP 445.
EXAMPLE 72
Methyl 4-({2-[4-(3,4-dichlorophenoxy)-1-piperidinyl]ethyl}amino)-4-oxobutanoate
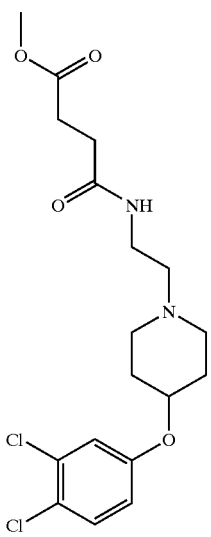
MS: APC1 (+ve) BP 403.

EXAMPLE 73
N-{2-[4-(3,4-Dichlorophenoxy)-1-piperidinyl]ethyl}bicyclo[2.2.1]hept-5-ene-2-carboxamide
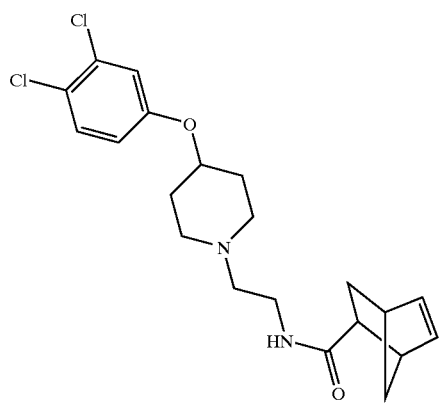
MS: APC1 (+ve) BP 409.
EXAMPLE 74
N-{2-[4-(3,4-Dichlorophenoxy)-1-piperidinyl]ethyl}cyclobutanecarboxamide
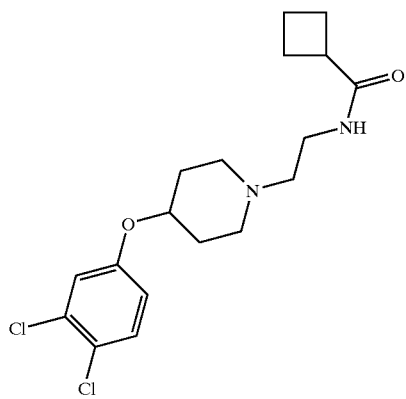
MS: APC1 (+ve) BP 371.
EXAMPLE 75
N-{2-[4-(3,4-Dichlorophenoxy)-1-piperidinyl]ethyl}-2-methoxyacetamide
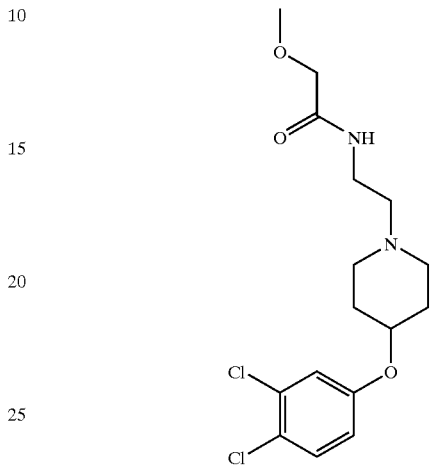
MS: APC1 (+ve) BP 361.
EXAMPLE 76
N-{2-[4-(3,4-Dichlorophenoxy)-1-piperidinyl]ethyl}cyclohexanecarboxamide
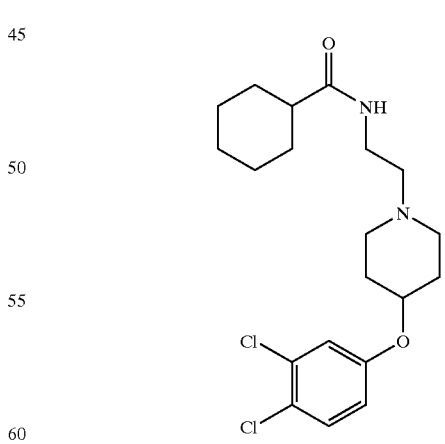
MS: APC1 (+ve) BP 399.

EXAMPLE 77
(E)-N-{2-[4-(3,4-Dichlorophenoxy)-1-piperidinyl]ethyl}-3-phenyl-2-propenamide
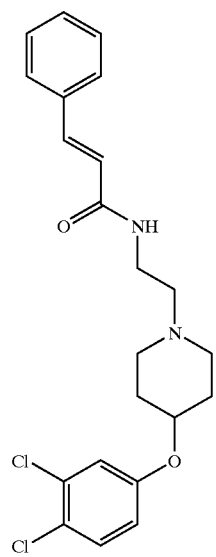
MS: APC1 (+ve) BP 419.
EXAMPLE 78
2-Chloro-N-{2-[4-(3,4-Dichlorophenoxy)-1-piperidinyl]ethyl}nicotinamide
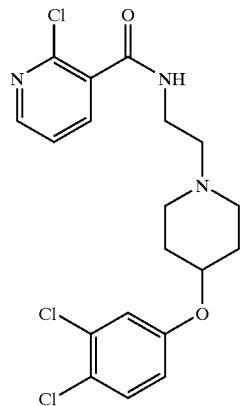
MS: APC1 (+ve) BP 430.
EXAMPLE 79
N-{2-[4-(3,4-Dichlorophenoxy)-1-piperidinyl]ethyl}-2-phenylacetamide
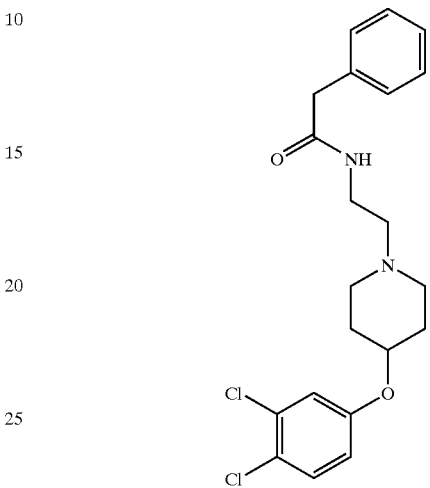
MS: APC1 (+ve) BP 407.
EXAMPLE 80
N-{2-[4-(3,4-Dichlorophenoxy)-1-piperidinyl]ethyl}cyclopentanecarboxamide
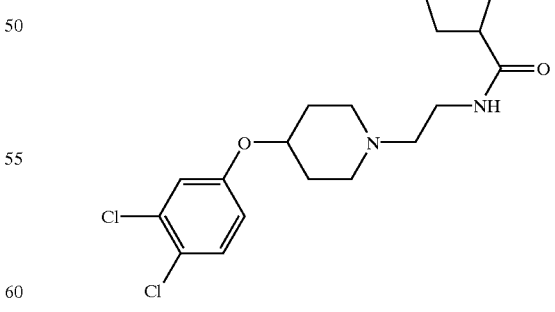
MS: APC1 (+ve) BP 385.

EXAMPLE 81
N-{2-[4-(3,4-Dichlorophenoxy)-1-piperidinyl]ethyl}-2-phenoxyacetamide
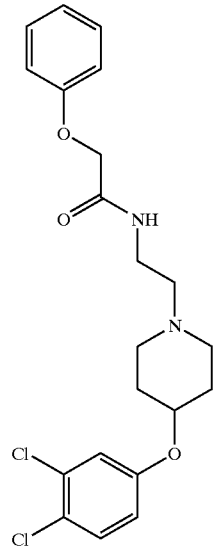
MS: APC1 (+ve) BP 423.
EXAMPLE 82
N-{2-[4-(4-Chlorobenzoyl)-1-piperidinyl]ethyl}benzamide
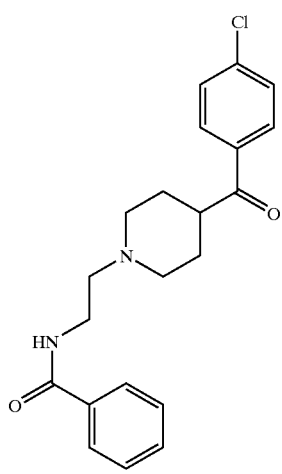
MS: APC1 (+ve) BP 371.
EXAMPLE 83
N-{2-[4-(4-Chlorobenzoyl)-1-piperidinyl]ethyl}-3-(trifluoromethyl)benzamide
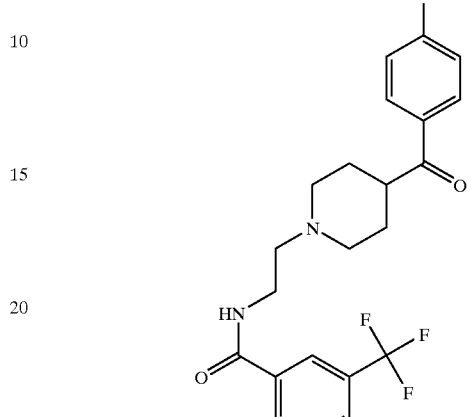
MS: APC1 (+ve) BP 439.
EXAMPLE 84
4-(tert-Butyl)-N-{2-[4-(4-chlorobenzoyl)-1-piperidinyl]ethyl}benzamide
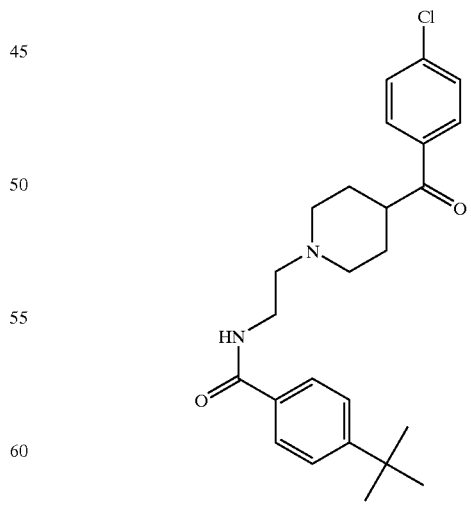
MS: APC1 (+ve) BP 427.

EXAMPLE 85
N-{2-[4-(4-Chlorobenzoyl)-1-piperidinyl]ethyl}-4-methylbenzamide
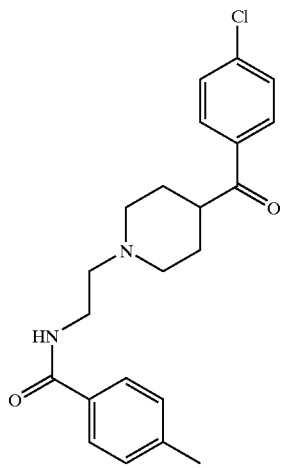
MS: APC1 (+ve) BP 385.
EXAMPLE 86
N-{2-[4-(4-Chlorobenzoyl)-1-piperidinyl]ethyl}-4-nitrobenzamide
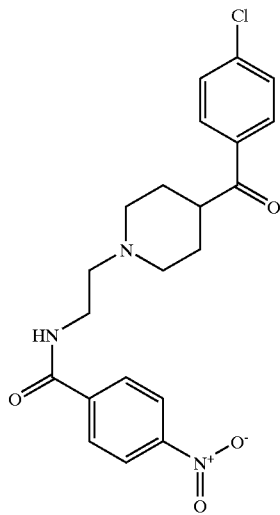
MS: APC1 (+ve) BP 416.
EXAMPLE 87
N-{2-[4-(4-Chlorobenzoyl)-1-piperidinyl]ethyl}-3-methylbenzamide
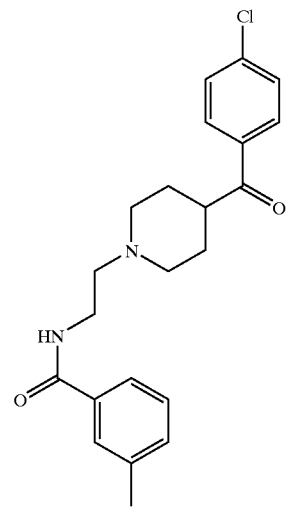
MS: APC1 (+ve) BP 385.
EXAMPLE 88
N-{2-[4-(4-Chlorobenzoyl)-1-piperidinyl]ethyl}-4-methyl-3-nitrobenzamide
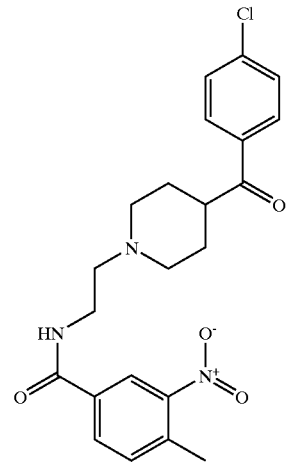
MS: APC1 (+ve) BP 430.

EXAMPLE 89
N-{2-[4-(4-Chlorobenzoyl)-1-piperidinyl]ethyl}-3-cyanobenzamide
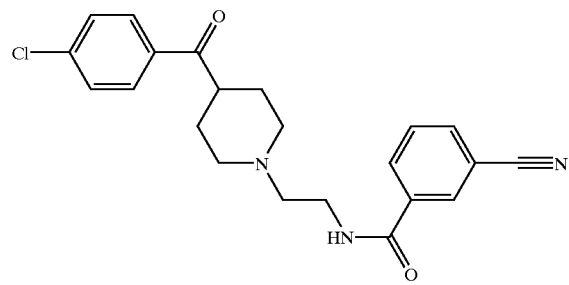
MS: APC1 (+ve) BP 396.
EXAMPLE 90
N-{2-[4-(4-Chlorobenzoyl)-1-piperidinyl]ethyl}-2-furamide
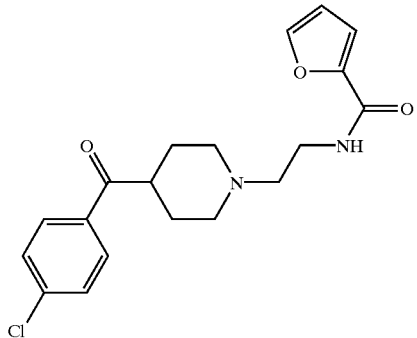
MS: APC1 (+ve) BP 361.
EXAMPLE 91
N-{2-[4-(4-Chlorobenzoyl)-1-piperidinyl]ethyl}-3-nitrobenzamide
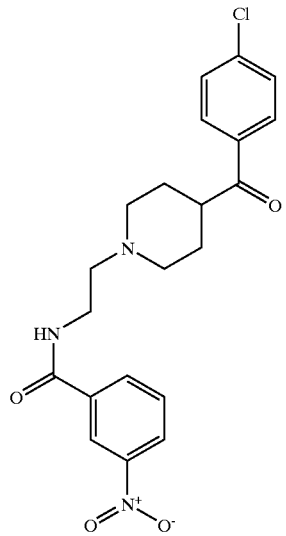
MS: APC1 (+ve) BP 416.
EXAMPLE 92
N-{2-[4-(4-Chlorobenzoyl)-1-piperidinyl]ethyl}-2-naphthamide
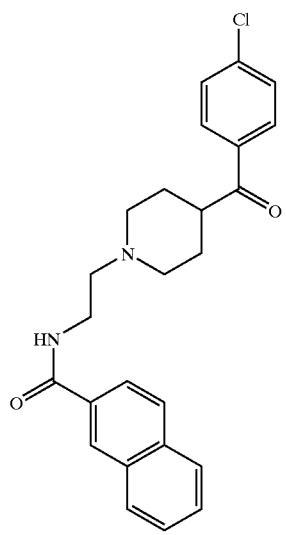
MS: APC1 (+ve) BP 421.

EXAMPLE 93

N-{2-[4-(4-Chlorobenzoyl)-1-piperidinyl]ethyl}-2-(methylsulfanyl)nicotinamide

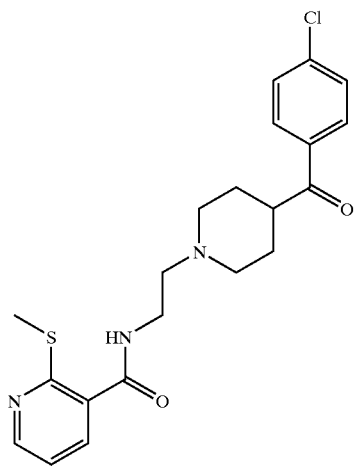

MS: APC1 (+ve) BP 418.

EXAMPLE 94

N-{2-[4-(4-Chlorobenzoyl)-1-piperidinyl]ethyl}-2-(2,3-dihydro-1,4-benzodioxin-2-2yl)-1,3-thiazole-4-carboxamide

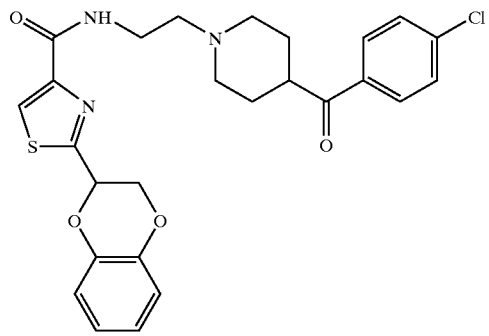

MS: APC1 (+ve) BP 512.

EXAMPLE 95

N~2~-Cyclopropyl-N~4~-{2-[4-(3,4-dichlorophenoxy)-1-piperidinyl]ethyl}-2,4-pyrimidinediamine

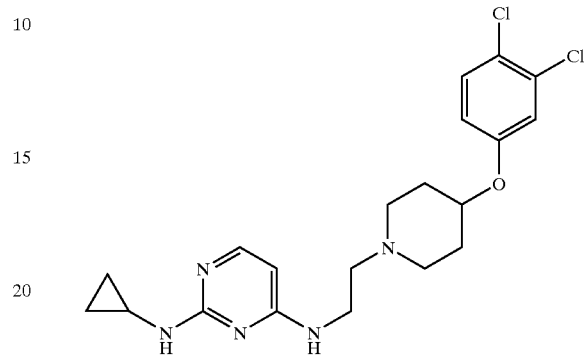

MS: APCI(+ve) 422 (M+1).

EXAMPLE 96

2-{[4-({2-[4-(3,4-Dichlorophenoxy)-1-piperidinyl]ethyl}amino)-2-pyrimidinyl]amino}-1-ethanol

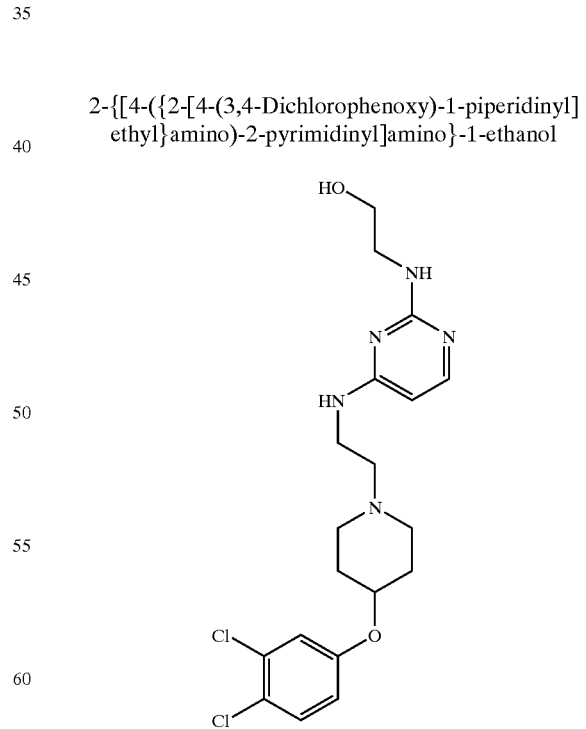

MS: APCI(+ve) 426 (M+1).

EXAMPLE 97

2-[[4-({2-[4-(3,4-Dichlorophenoxy)-1-piperidinyl]ethyl}amino)-2-pyrimidinyl](methyl)amino]-1-ethanol

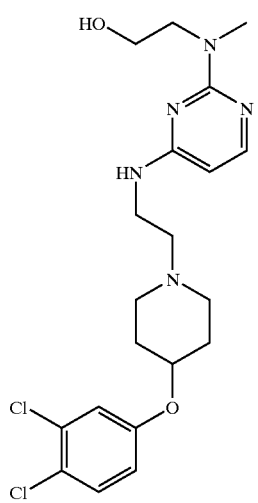

MS: APCI(+ve) 440 (M+1).

EXAMPLE 98

N~4~-{2-[4-(3,4-Dichlorophenoxy)-1-piperidinyl]ethyl}-N~2~-phenyl-2,4-pyrimidinediamine

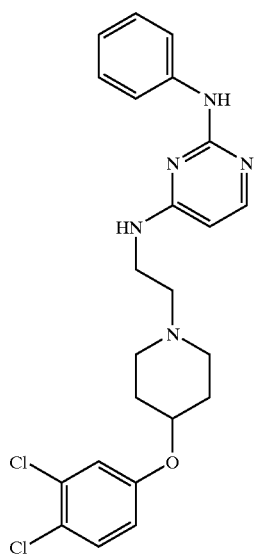

MS: APCI(+ve) 458 (M+1).

EXAMPLE 99

N-{2-[4-(3,4-Dichlorophenoxy)-1-piperidinyl]ethyl}-2-(methylsulfanyl)-4-pyrimidinamine

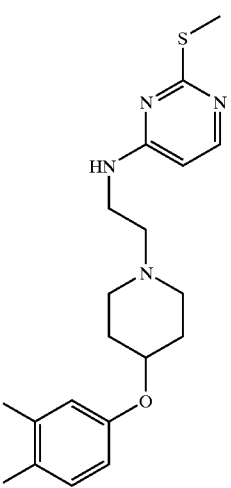

MS: APCI(+ve) 413 (M+1).

EXAMPLE 100

N~4~-{2-[4-(3,4-Dichlorophenoxy)-1-piperidinyl]ethyl}-6-methyl-2,4-pyrimidinediamine

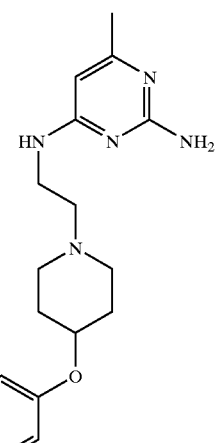

MS: APCI(+ve) 396 (M+1).

EXAMPLE 101

N~4~-{2-[4-(3,4-Dichlorophenoxy)-1-piperidinyl]ethyl}-N~2~,6-dimethyl-2,4-pyrimidinediamine

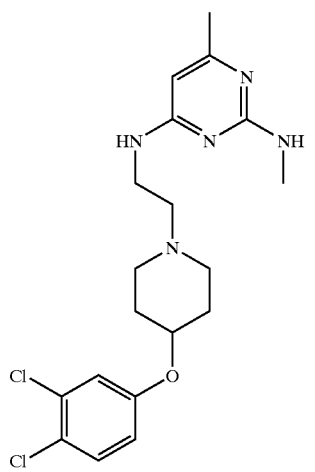

MS: APCI(+ve) 410 (M+1).

EXAMPLE 102

2-Chloro-N~4~-cyclopropyl-N~6~-{2-[4-(3,4-dichlorophenoxy)-1-piperidinyl]ethyl}-4,6-pyrimidinediamine

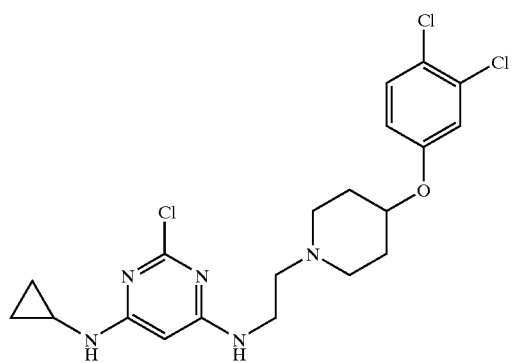

MS: APCI(+ve) 456 (M+1).

EXAMPLE 103

N-{2-[4-(3,4-Dichlorophenoxy)-1-piperidinyl]ethyl}-4-phenyl-2-pyrimidinamine

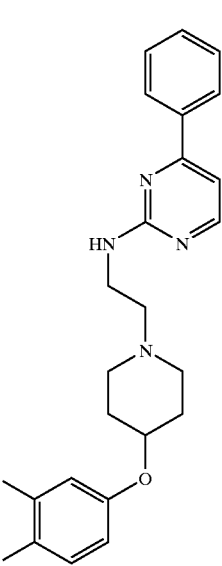

MS: APCI(+ve) 443 (M+1).

EXAMPLE 104

N~2~-{2-[4-(3,4-Dichlorophenoxy)-1-piperidinyl]ethyl}-N~4~,N~4~, 6-trimethyl-2,4-pyrimidinediamine

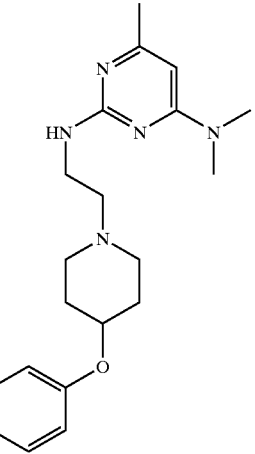

MS: APCI(+ve) 424 (M+1).

EXAMPLE 105

N-{2-[4-(3,4-Dichlorophenoxy)-1-piperidinyl]ethyl}-4-(trifluoromethyl)-2-pyrimidinamine

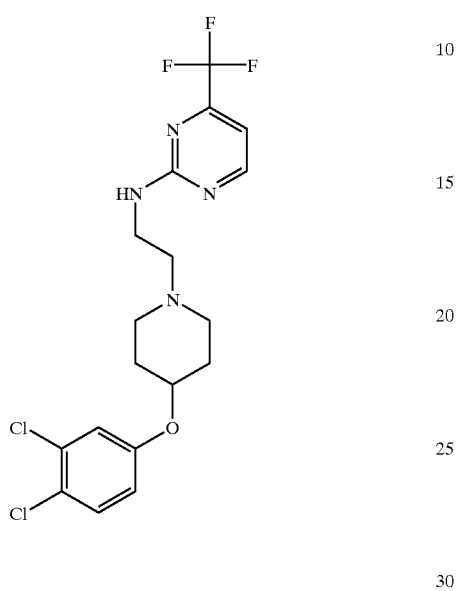

MS: APCI(+ve) 435 (M+1).

EXAMPLE 106

N-{2-[4-(3,4-Dichlorophenoxy)-1-piperidinyl]ethyl}-4-(propylsulfanyl)-2-pyrimidinamnine

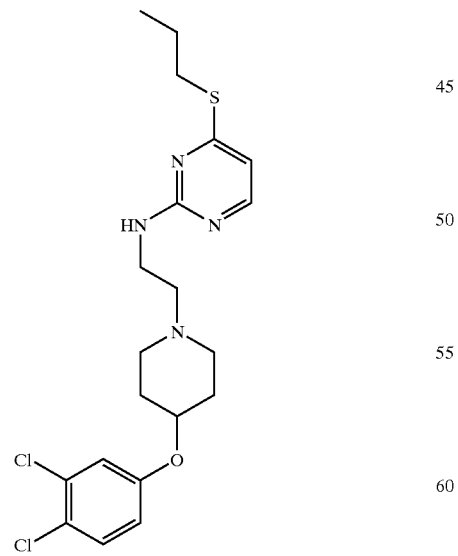

MS: APCI(+ve) 441 (M+1).

EXAMPLE 107

N~2~-{2-[4-(3,4-Dichlorophenoxy)-1-piperidinyl]ethyl}-N~4~-phenyl-2,4-pyrimidinediamine

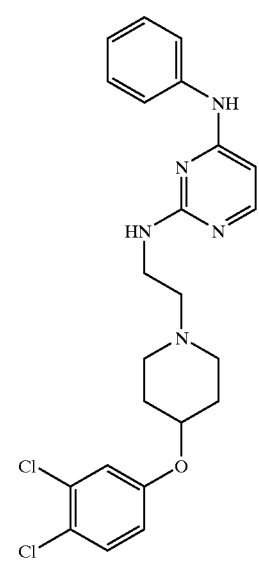

MS: APCI(+ve) 458 (M+1).

EXAMPLE 108

N~4~-Cyclopropyl-N~2~-{2-[4-(3,4-dichlorophenoxy)-1-piperidinyl]ethyl}-2,4-pyrimidinediamine

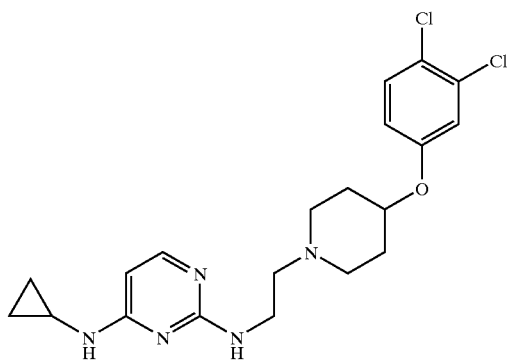

MS: APCI(+ve) 422 (M+1).

EXAMPLE 109
N-{2-[4-(3,4-Dichlorophenoxy)-1-piperidinyl]ethyl}[1,8]naphthyridin-2-amine
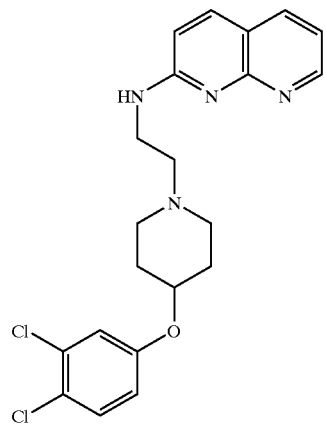
MS: APCI(+ve) 417 (M+1).
EXAMPLE 110
N-{2-[4-(3,4-Dichlorophenoxy)-1-piperidinyl]ethyl}-4-(3-pyridinyl)-2-pyrimidinamine
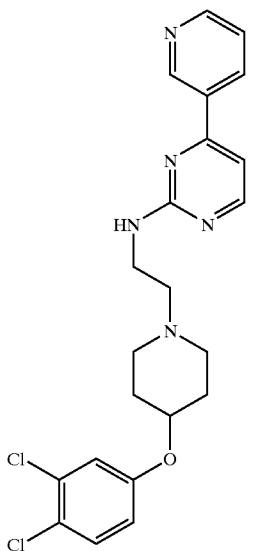
MS: APCI(+ve) 444 (M+1).
EXAMPLE 111
N-{2-[4-(3,4-Dichlorophenoxy)-1-piperidinyl]ethyl}-2-pyrimidinamine
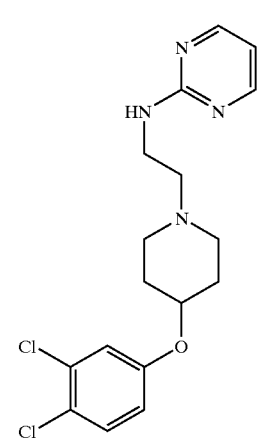
MS: APCI(+ve) 367 (M+1).
EXAMPLE 112
N-{2-[4-(3,4-Dichlorophenoxy)-1-piperidinyl]ethyl}-4,6-dimethoxy-2-pyrimidinamine
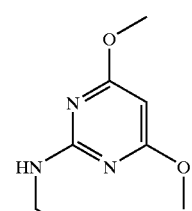
MS: APCI(+ve) 427 (M+1).

EXAMPLE 113

N-{2-[4-(3,4-Dichlorophenoxy)-1-piperidinyl]ethyl}-4-(3-furyl)-2-pyrimidinamine

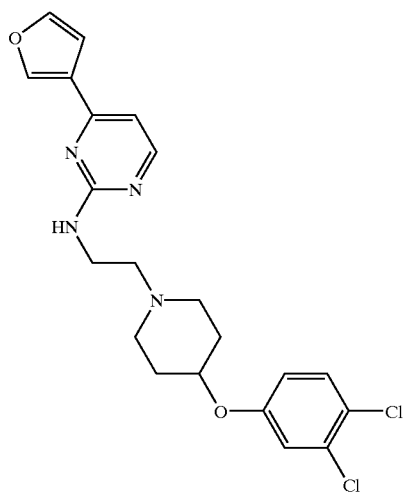

MS: APCI(+ve) 433 (M+1).

EXAMPLE 114

N-{2-[4-(3,4-Dichlorophenoxy)-1-piperidinyl]ethyl}-1-methyl-1H-pyrazolo[3,4-d]pyrimidin-4-amine

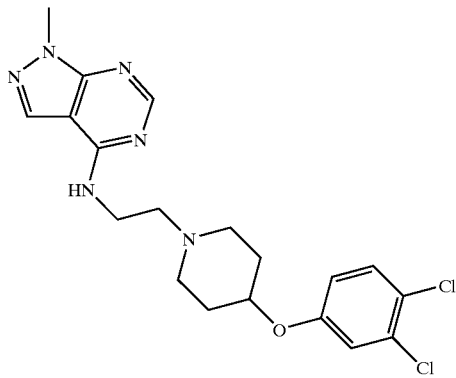

MS: APCI(+ve) 421 (M+1).

EXAMPLE 115

N-{2-[4-(3,4-Dichlorophenoxy)-1-piperidinyl]ethyl}-1H-purin-6-amine

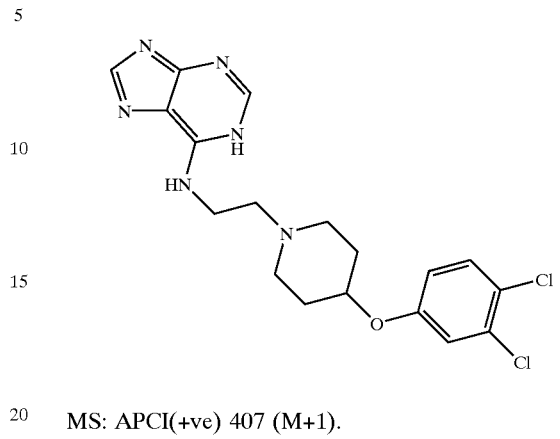

MS: APCI(+ve) 407 (M+1).

EXAMPLE 116

N-{2-[4-(3,4-Dichlorophenoxy)-1-piperidinyl]ethyl}-5-methylthieno[2,3-d]pyrimidin-4-amine

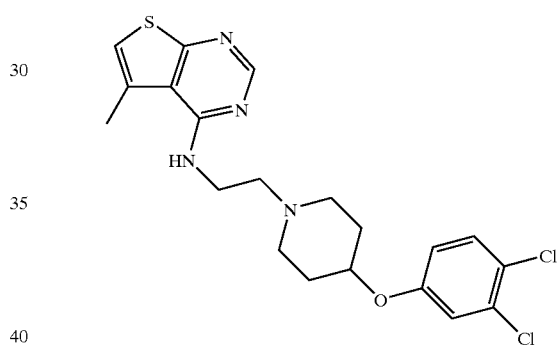

MS: APCI(+ve) 437 (M+1).

EXAMPLE 117

N-{2-[4-(3,4-Dichlorophenoxy)-1-piperidinyl]ethyl}-7-methylthieno[3,2-d]pyrimidin-4-amine

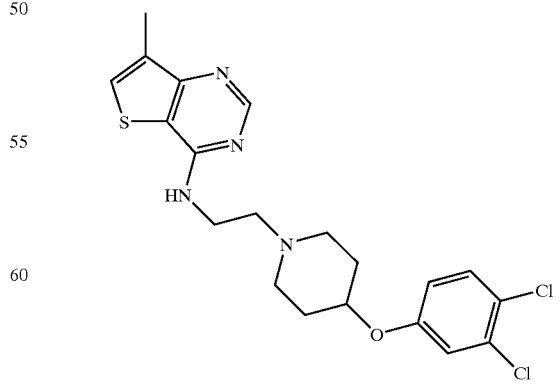

MS: APCI(+ve) 437 (M+1).

EXAMPLE 118
N-{2-[4-(4-Chlorobenzoyl)-1-piperidinyl]ethyl}-2-thiophenecarboxamide
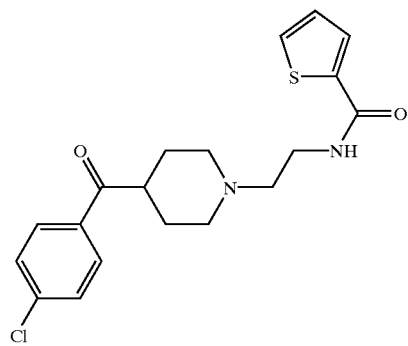
MS: APC1 (+ve) BP 377.
EXAMPLE 119
N-{2-[4-(4-Chlorobenzoyl)-1-piperidinyl]ethyl}-2-quinoxalinecarboxamide
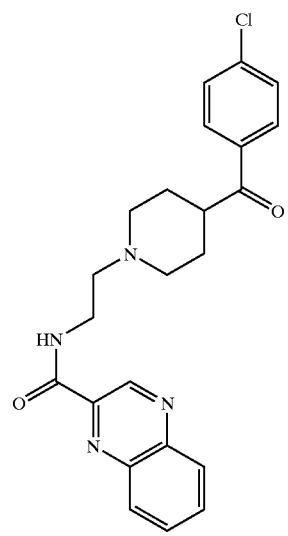
MS: APC1 (+ve) BP 423.
EXAMPLE 120
N-{2-[4-(4-Chlorobenzoyl)-1-piperidinyl]ethyl}bicyclo[2.2.1]hept-5-ene-2-carboxamide
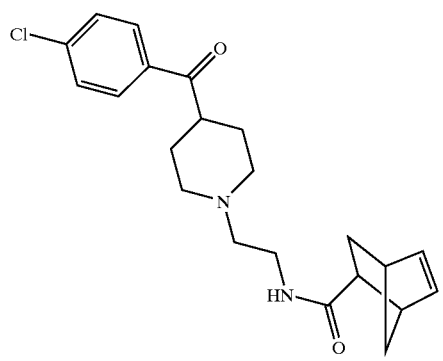
MS: APC1 (+ve) BP 387.
EXAMPLE 121
N-{2-[4-(4-Chlorobenzoyl)-1-piperidinyl]ethyl}cyclohexanecarboxamide
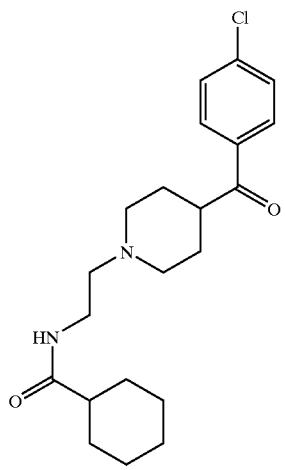
MS: APC1 (+ve) BP 377.

EXAMPLE 122

(E)-N-{2-[4-(4-Chlorobenzoyl)-1-piperidinyl]ethyl}-3-phenyl-2-propenamide

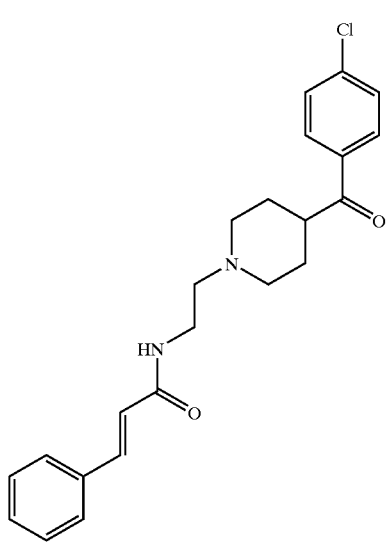

MS: APC1 (+ve) BP 397.

EXAMPLE 123

N-{2-[4-(4-Chlorobenzoyl)-1-piperidinyl]ethyl}-2-phenoxyacetamide

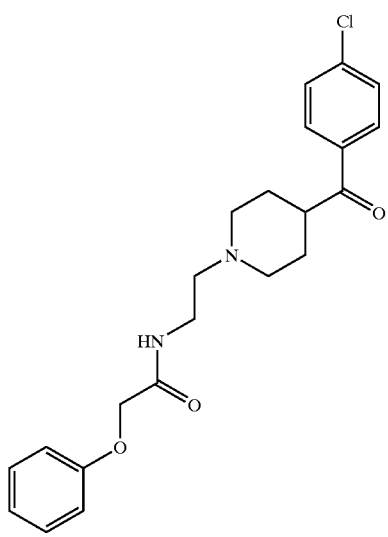

MS: APC1 (+ve) BP 401.

EXAMPLE 124

(E)-N-{2-[4-(4-Chlorobenzoyl)-1-piperidinyl]ethyl}-3-(4-nitrophenyl)-2-propenamide

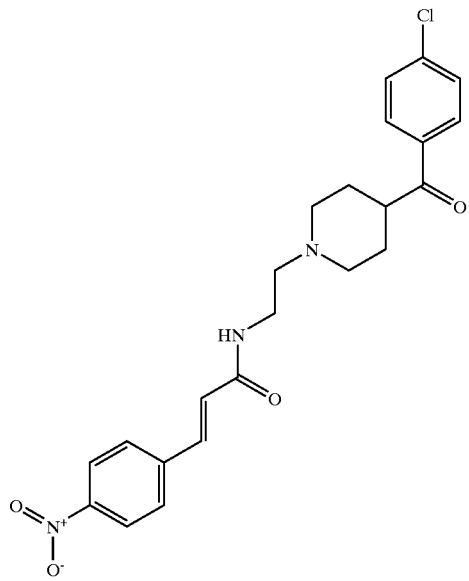

MS: APC1 (+ve) BP 442.

EXAMPLE 125

2-(1-Adamantyl)-N-{2-[4-(4-chlorobenzoyl)-1-piperidinyl]ethyl}acetamide

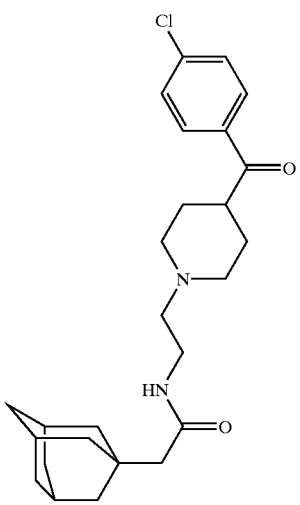

MS: APC1 (+ve) BP 443.

The compounds of following Examples 126 to 168 were prepared by methods analogous to the method of Example 30.

EXAMPLE 126
(4-Chlorophenyl)(1-{2-[(2-fluoro-4,5-dimethoxybenzyl)amino]ethyl}-4-piperidinyl)methanone
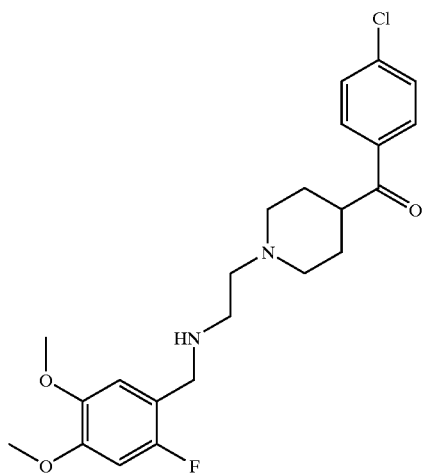
MS: APC1 (+ve) BP 435.
EXAMPLE 127
(4-Chlorophenyl)(1-{2-[(3,4,5-trimethoxybenzyl)amino]ethyl}-4-piperidinyl)methanone
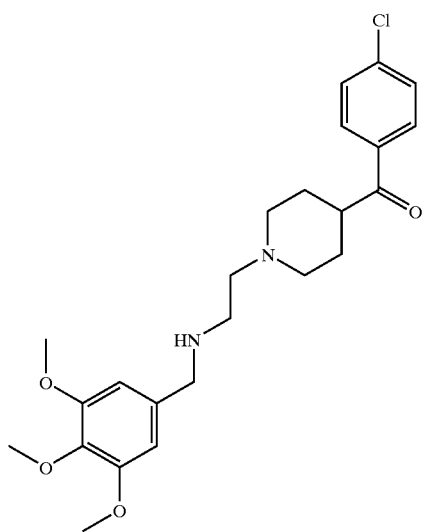
MS: APC1 (+ve) BP 447.
EXAMPLE 128
(4-Chlorophenyl)(1-{2-[(3-nitrobenzyl)amino]ethyl}-4-piperidinyl)methanone
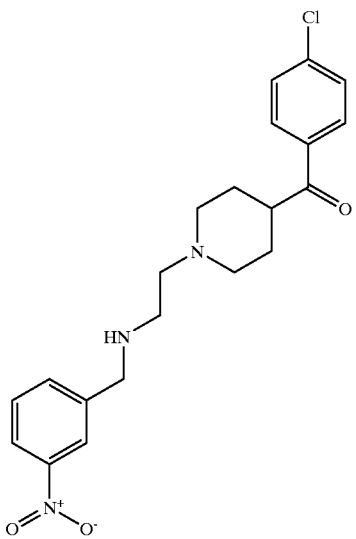
MS: APC1 (+ve) BP 402.
EXAMPLE 129
(4-Chlorophenyl){1-[2-(isobutylamino)ethyl]-4-piperidinyl}methanone
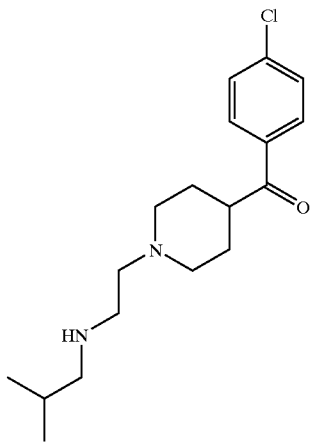
MS: APC1 (+ve) BP 323.

EXAMPLE 130

4-[({2-[4-(4-Chlorobenzoyl)-1-piperidinyl]ethyl}amino)methyl]-4-ethylhexanenitrile

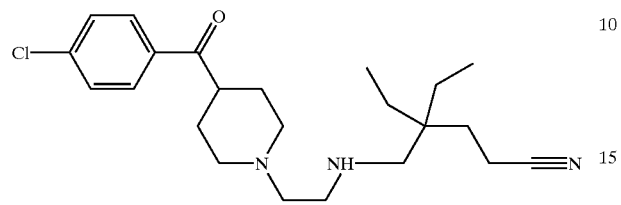

MS: APC1 (+ve) BP 404.

EXAMPLE 131

(4-Chlorophenyl)(1-{2-[(7-hydroxy-3,7-dimethyloctyl)amino]ethyl}-4-piperidinyl)methanone

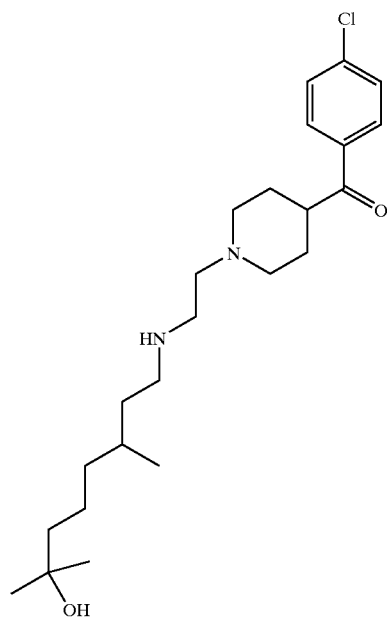

MS: APC1 (+ve) BP 423.

EXAMPLE 132

(4-Chlorophenyl)[1-(2-{[(6-nitro-1,3-benzodioxol-5-yl)methyl]amino}ethyl)-4-piperidinyl]methanone

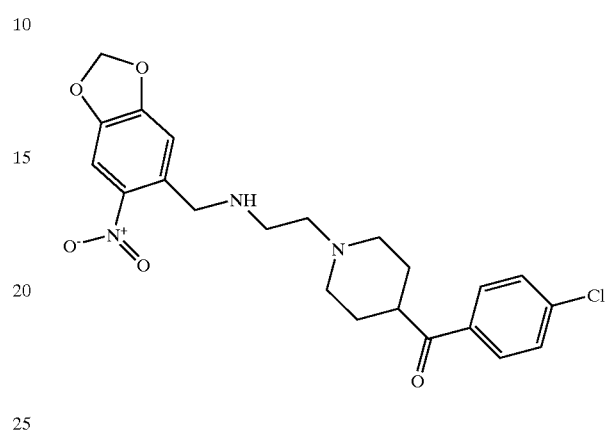

MS: APC1 (+ve) BP 446.

EXAMPLE 133

[1-(2-{[(5-Chloro-1,3-dimethyl-1H-pyrazol-4-yl)methyl]amino}ethyl)-4-piperidinyl](4-chlorophenyl)methanone

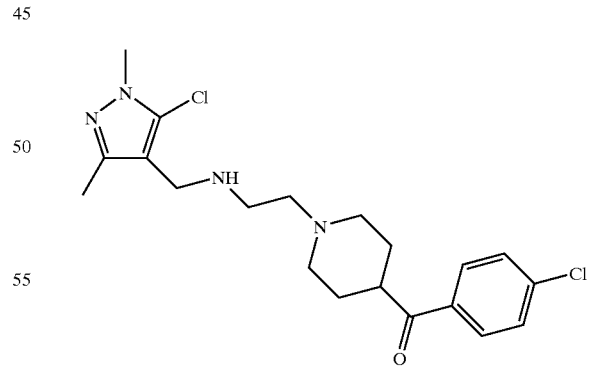

MS: APC1 (+ve) BP 409.

EXAMPLE 134

(4-Chlorophenyl)[1-(2-{[3-nitro-4-(2-pyridinylsulfanyl)benzyl]amino}ethyl)-4-piperidinyl]methanone

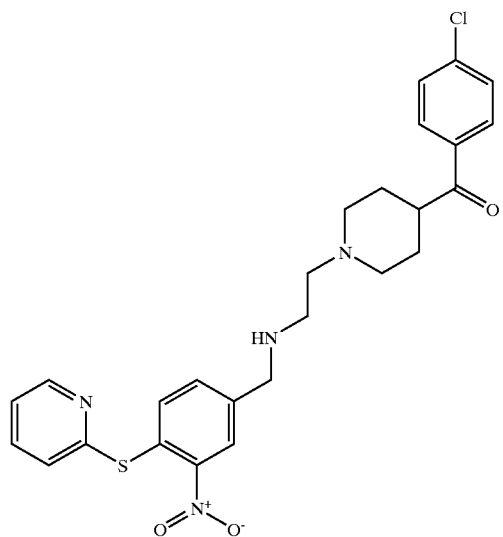

MS: APC1 (+ve) BP 511.

EXAMPLE 135

(4-Chlorophenyl)[1-(2-{[(E)-3-(4-nitrophenyl)-2-propenyl]amino}ethyl)-4-piperidinyl]methanone

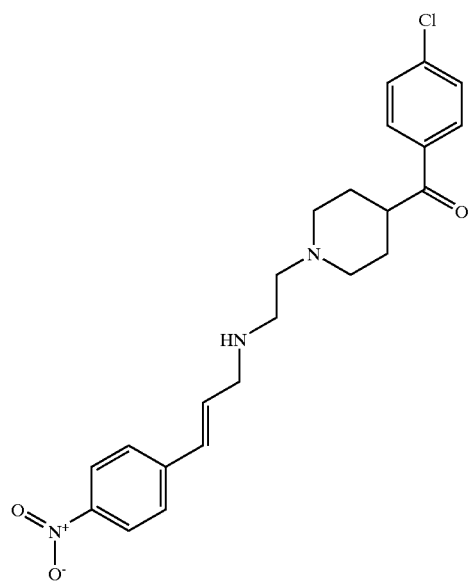

MS: APC1 (+ve) BP 428.

EXAMPLE 136

(4-Chlorophenyl){1-[2-({[5-(3-nitrophenyl)-2-furyl]methyl}amino)ethyl]-4-piperidinyl}methanone

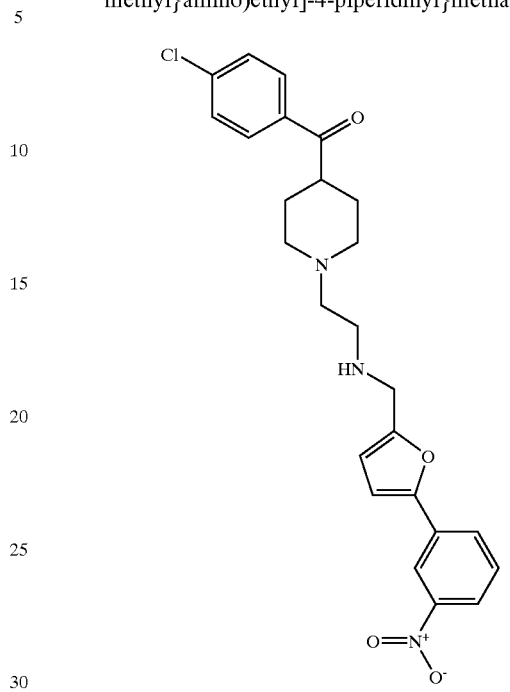

MS: APC1 (+ve) BP 468.

EXAMPLE 137

(4-Chlorophenyl)[1-(2-{[5-nitro-2-(2-pyridinylsulfanyl)benzyl]amino}ethyl)-4-piperidinyl]methanone

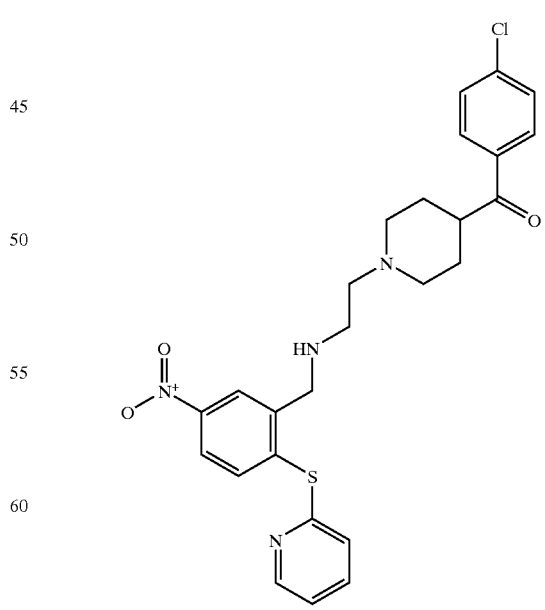

MS: APC1 (+ve) BP 511.

EXAMPLE 138

6-[({2-[4-(4-Chlorobenzoyl)-1-piperidinyl]
ethyl}amino)methyl]-2-(methylsulfanyl)
nicotinonitrile

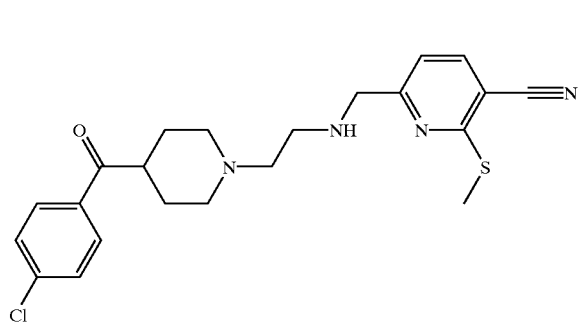

MS: APC1 (+ve) BP 429.

EXAMPLE 139

{1-[2-({[5-Chloro-1-methyl-3-(trifluoromethyl)-1H-
pyrazol-4-yl]methyl}amino)ethyl]-4-piperidinyl}(4-
chlorophenyl)methanone

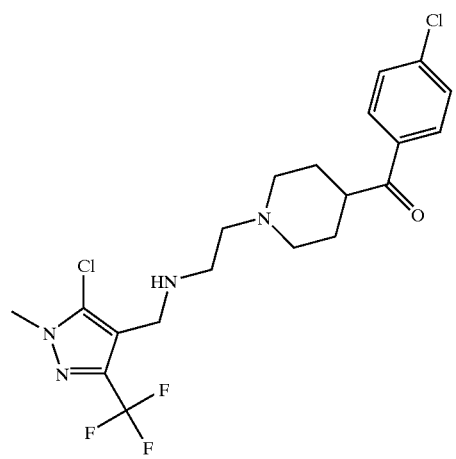

MS: APC1 (+ve) BP 463.

EXAMPLE 140

(4-Chlorophenyl)[1-(2-{[3-(methylsulfanyl)butyl]
amino}ethyl)4-piperidinyl]methanone

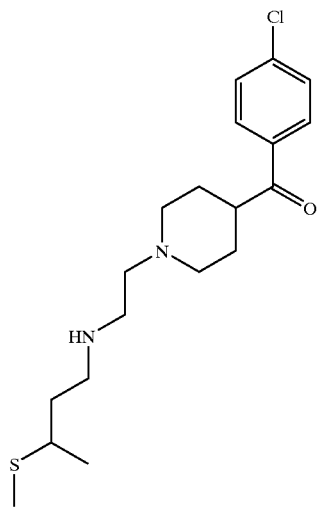

MS: APC1 (+ve) BP 369.

EXAMPLE 141

(4-Chlorophenyl)[1-(2-{[(4-phenyl-4-piperidinyl)
methyl]amino}ethyl)-4-piperidinyl]methanone

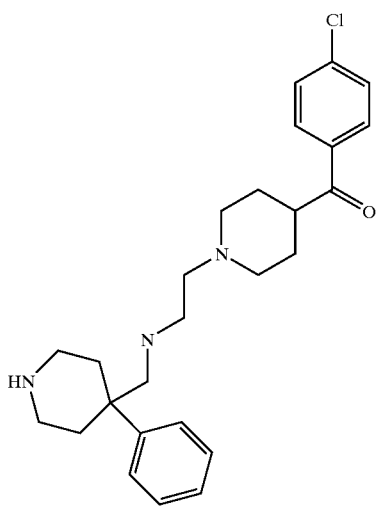

MS: APC1 (+ve) BP 440.

EXAMPLE 142

(4-Chlorophenyl)[1-(2-{[(1-phenyl-1H-pyrazol-5-yl)methyl]amino}ethyl)-4-piperidinyl]methanone

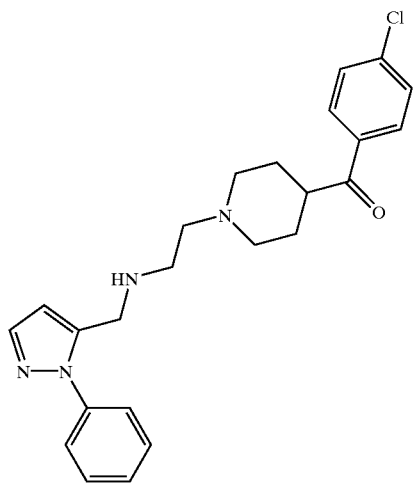

MS: APC1 (+ve) BP 423.

EXAMPLE 143

Ethyl 3-[({2-[4-(4-chlorobenzoyl)-1-piperidinyl]ethyl}-amino)methyl]cyclohexanecarboxylate

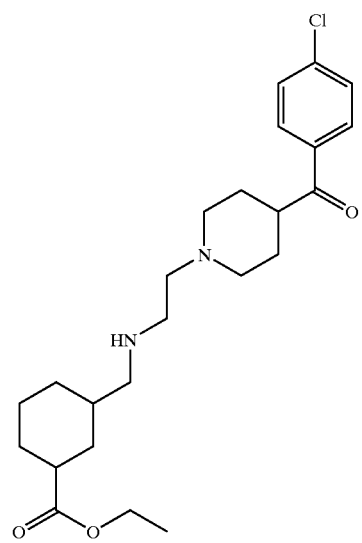

MS: APC1 (+ve) BP 435.

EXAMPLE 144

N-{4-[({2-[4-(4-Chlorobenzoyl)-1-piperidinyl]ethyl}amino)methyl]phenyl}acetamide

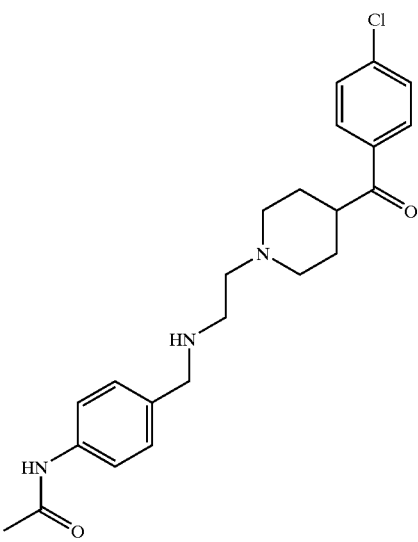

MS: APC1 (+ve) BP 414.

EXAMPLE 145

(4-Chlorophenyl)(1-{2-[(2,5-difluorobenzyl)amino]ethyl}-4-piperidinyl)methanone

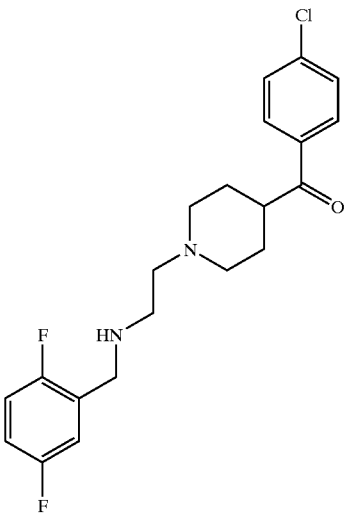

MS: APC1 (+ve) BP 393.

EXAMPLE 146
(4-Chlorophenyl)(1-{2-[(4-nitrobenzyl)amino]
ethyl}-4-piperidinyl)methanone
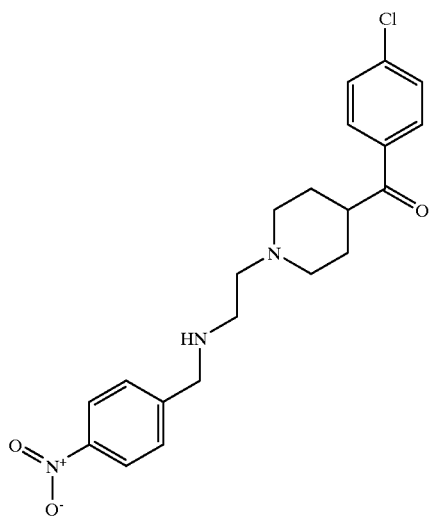
MS: APC1 (+ve) BP 402.
EXAMPLE 147
(4-Chlorophenyl)(1-{2-[(2,6-dichlorobenzyl)amino]
ethyl}-4-piperidinyl)methanone
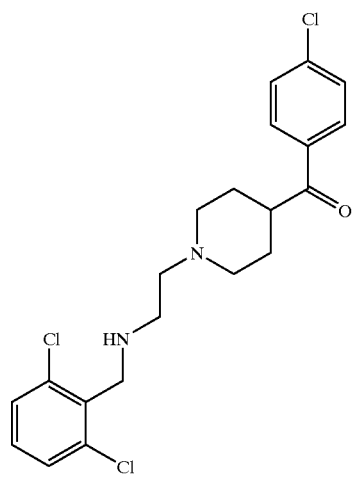
MS: APC1 (+ve) BP 425.
EXAMPLE 148
(4-Chlorophenyl)(1-{2-[(2-pyridinylmethyl)amino]
ethyl}-4-piperidinyl)methanone
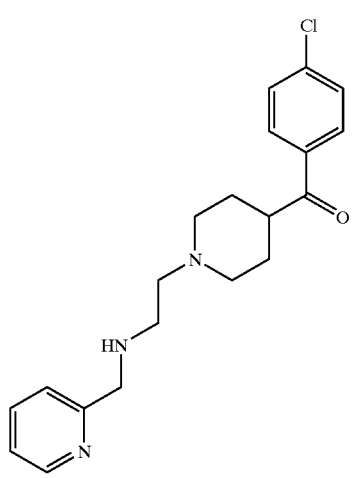
MS: APC1 (+ve) BP 358.
EXAMPLE 149
(4-Chlorophenyl)[1-(2-{[(3-methyl-2-thienyl)
methyl]amino}ethyl)-4-piperidinyl]methanone
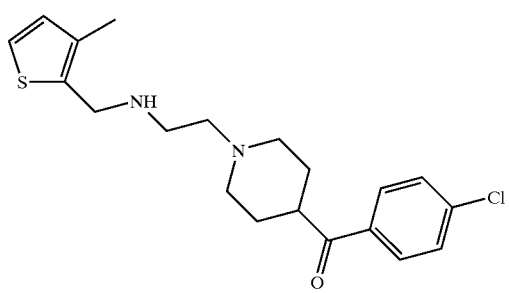
MS: APC1 (+ve) BP 377.

EXAMPLE 150

(4-Chlorophenyl)(1-{2-[(3-hydroxy-4-methoxybenzyl)amino]ethyl}-4-piperidinyl)methanone

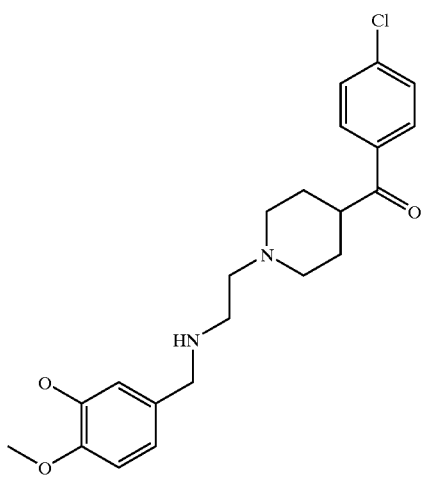

MS: APC1 (+ve) BP 403.

EXAMPLE 151

3-[({2-[4-(4-Chlorobenzoyl)-1-piperidinyl]ethyl}amino)methyl]-4H-chromen-4-one

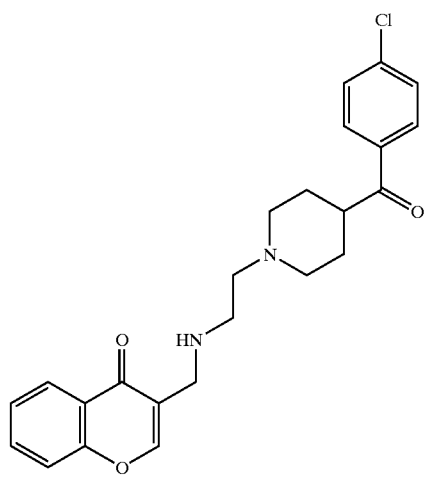

MS: APC1 (+ve) BP 425.

EXAMPLE 152

[1-(2-{[(5-Chloro-1,3-dimethyl-1H-pyrazol-4-yl)methyl]amino}ethyl)-4-piperidinyl](4-chlorophenyl)methanone

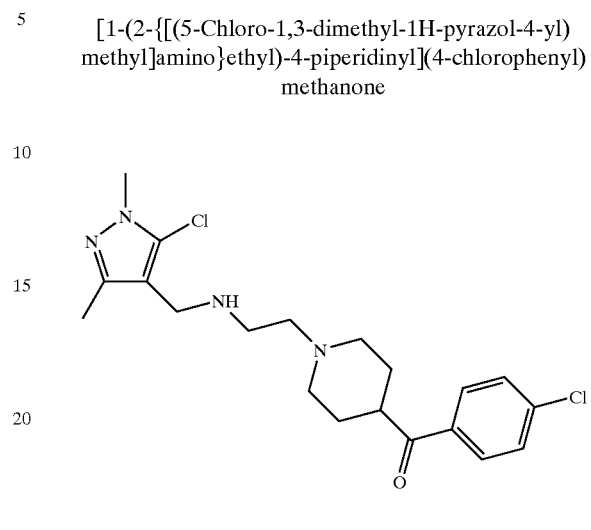

MS: APC1 (+ve) BP 409.

EXAMPLE 153

(4-Chlorophenyl)[1-(2-{[(2,6-dichloro-4-pyridinyl)methyl]amino}ethyl)-4-piperidinyl]methanone

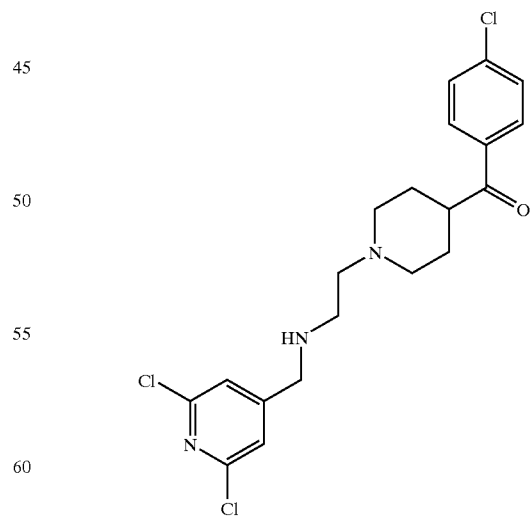

MS: APC1 (+ve) BP 428.

EXAMPLE 154

(4-Chlorophenyl)[1-(2-{[(2-phenyl-1H-imidazol-4-yl)methyl]amino}ethyl)-4-piperidinyl]methanone

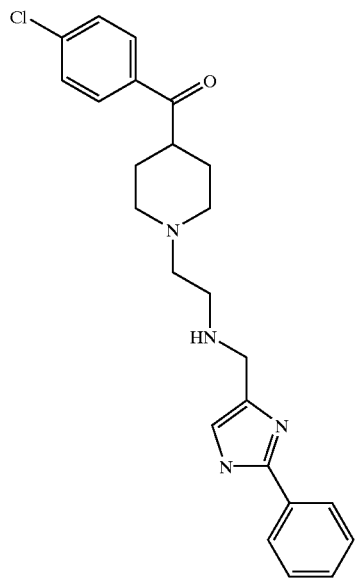

MS: APC1 (+ve) BP 423.

EXAMPLE 155

(4-Chlorophenyl)[1-(2-{[(5-ethyl-2-thienyl)methyl]amino}ethyl)-4-piperidinyl]methanone

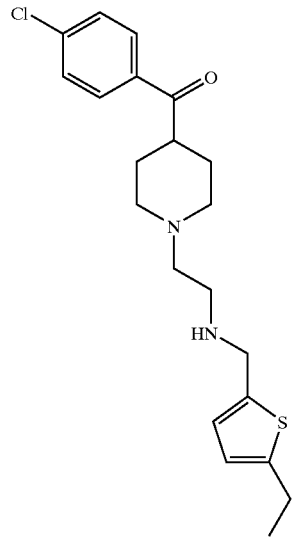

MS: APC1 (+ve) BP 391.

EXAMPLE 156

(4-Chlorophenyl)[1-(2-{[(2-chloro-3-quinolinyl)methyl]amino}ethyl)-4-piperidinyl]methanone

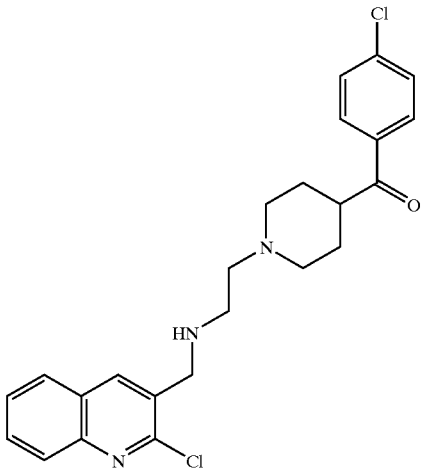

MS: APC1 (+ve) BP 442.

EXAMPLE 157

(4-Chlorophenyl)[1-(2-{[(6-methyl-2-pyridinyl)methyl]amino}ethyl)-4-piperidinyl]methanone

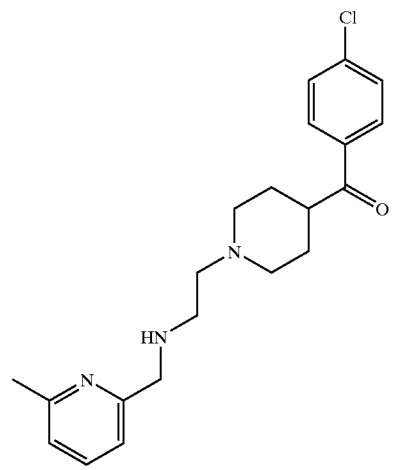

MS: APC1 (+ve) BP 372.

EXAMPLE 158

(4-Chlorophenyl)(1-{2-[(3-quinolinylmethyl)amino]ethyl}-4-piperidinyl)methanone

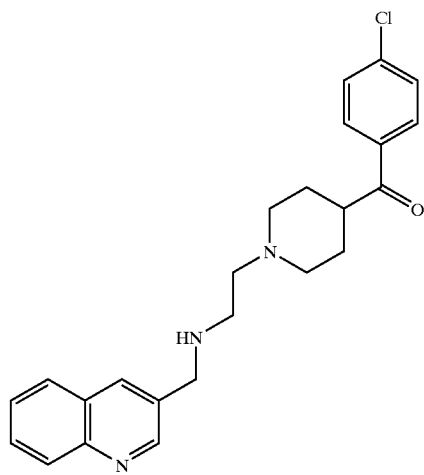

MS: APC1 (+ve) BP 408.

EXAMPLE 159

4-[({2-[4-(4-Chlorobenzoyl)-1-piperidinyl]ethyl}amino)methyl]-1,5-dimethyl-2-phenyl-1,2-dihydro-3H-pyrazol-3-one

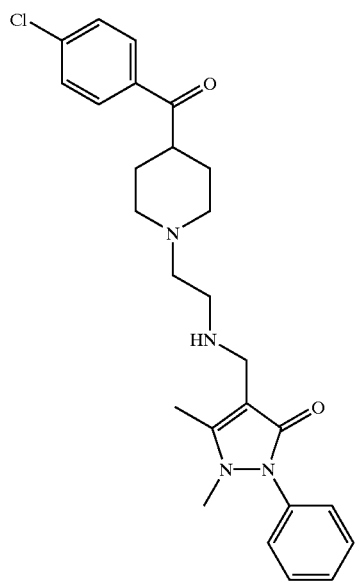

MS: APC1 (+ve) BP 467.

EXAMPLE 160

(4-Chlorophenyl)(1-{2-[(4-pyridinylmethyl)amino]ethyl}-4-piperidinyl)methanone

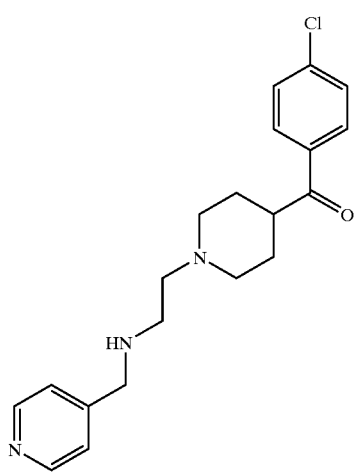

MS: APC1 (+ve) BP 358.

EXAMPLE 161

(4-Chlorophenyl)(1-{2-[(3-hydroxy-4-nitrobenzyl)amino]ethyl}-4-piperidinyl)methanone

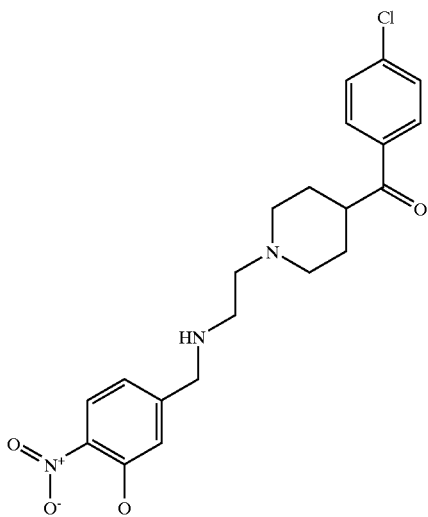

MS: APC1 (+ve) BP 418.

EXAMPLE 162

(4-Chlorophenyl)(1-{2-[(3,5-difluorobenzyl)amino]ethyl}-4-piperidinyl)methanone

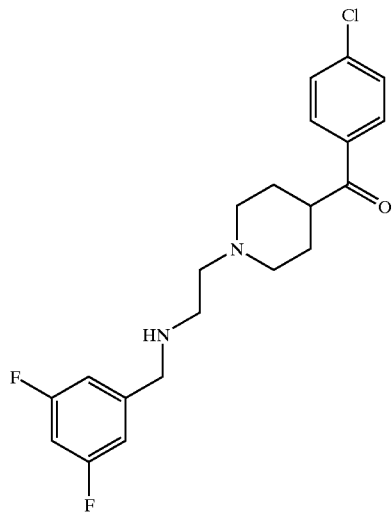

MS: APC1 (+ve) BP 393.

EXAMPLE 163

(1-{2-[(2-Chloro-6-fluorobenzyl)amino]ethyl}-4-piperidinyl)(4-chlorophenyl)methanone

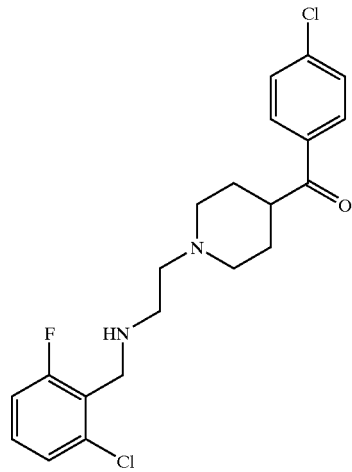

MS: APC1 (+ve) BP 409.

EXAMPLE 164

[1-(2-{[(4-Bromo-1H-pyrazol-3-yl)methyl]amino}ethyl)4-piperidinyl](4-chlorophenyl)methanone

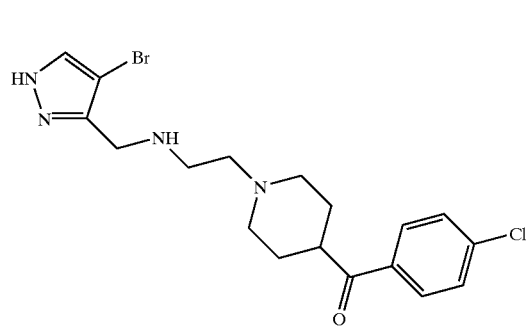

MS: APC1 (+ve) BP 427.

EXAMPLE 165

3-[({2-[4-(4-Chlorobenzoyl)-1-piperidinyl]ethyl}amino)methyl]-6,7-dimethyl-4H-chromen-4-one

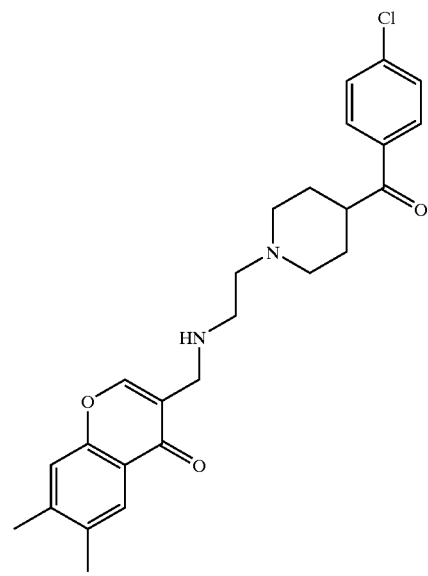

MS: APC1 (+ve) BP 453.

EXAMPLE 166

2-{2-[({2-[4-(4-Chlorobenzoyl)-1-piperidinyl]ethyl}amino)methyl]-4-nitrophenoxy}acetic acid

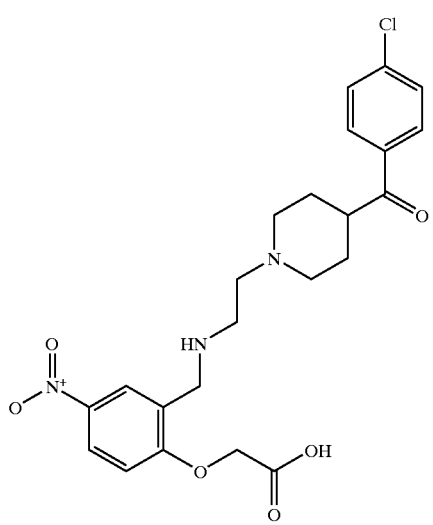

MS: APC1 (+ve) BP 476.

EXAMPLE 167

(4-Chlorophenyl)[1-(2-{[(1-methyl-1H-benzimidazol-2-yl)methyl]amino}ethyl)-4-piperidinyl]methanone

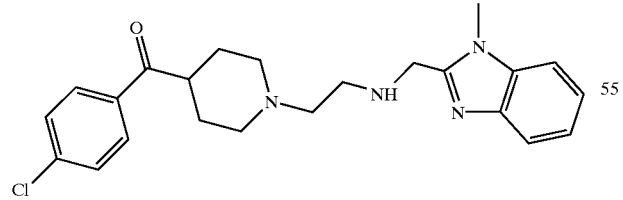

MS: APC1 (+ve) BP 411.

EXAMPLE 168

(4-Chlorophenyl)[1-(2-{[(2,4-dimethoxy-5-pyrimidinyl)methyl]amino}ethyl)-4-piperidinyl]methanone

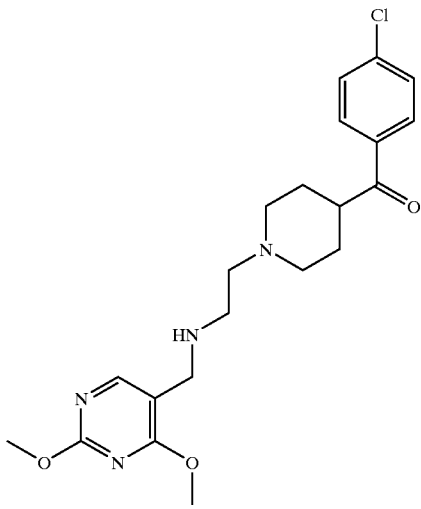

MS: APC1 (+ve) BP 419.

The compounds of following Examples 169 to 209 were prepared by methods analogous to the method of Example 2.

EXAMPLE 169

N-{2-[4-(3,4-Dichlorophenoxy)-1-piperidinyl]ethyl}-4-(methylamino)benzamide

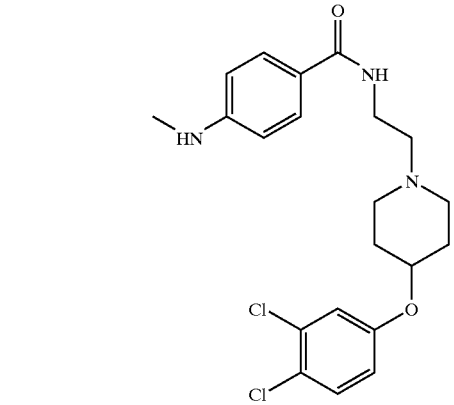

MS: APC1 (+ve) BP 422.

EXAMPLE 170
4-Chloro-N-{2-[4-(3,4-dichlorophenoxy)-1-piperidinyl]ethyl}-3-methoxybenzamide
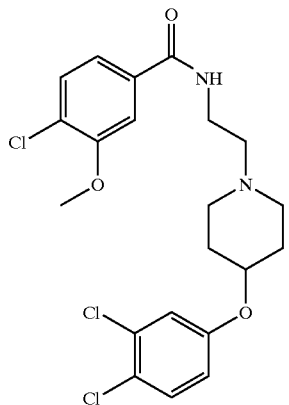
MS: APC1 (+ve) BP 459.
EXAMPLE 171
N-{2-[4-(3,4-Dichlorophenoxy)-1-piperidinyl]ethyl}-3-methoxy-4-methylbenzamide
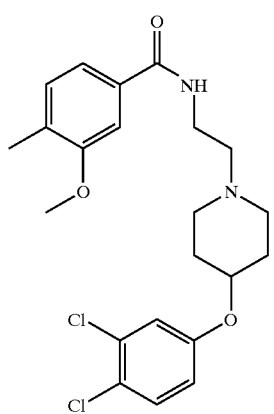
MS: APC1 (+ve) BP 437.
EXAMPLE 172
3-Amino-N-{2-[4-(3,4-dichlorophenoxy)-1-piperidinyl]ethyl}-4-methoxybenzamide
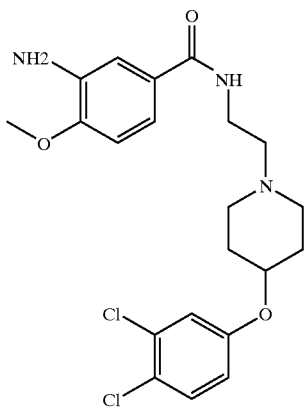
MS: APC1 (+ve) BP 438.
EXAMPLE 173
N-{2-[4-(3,4-Dichlorophenoxy)-1-piperidinyl]ethyl}-1,3-benzodioxole-5-carboxamide
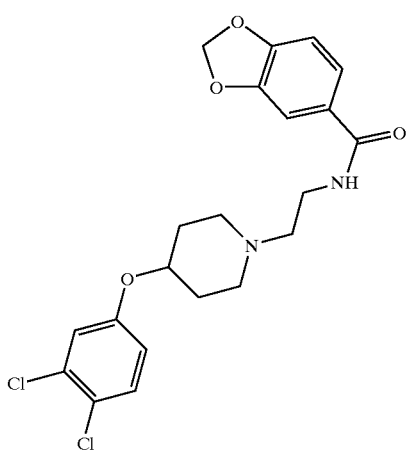
MS: APC1 (+ve) BP 437.

EXAMPLE 174
4-Amino-N-{2-[4-(3,4-dichlorophenoxy)-1-piperidinyl]ethyl}-3-methoxybenzamide
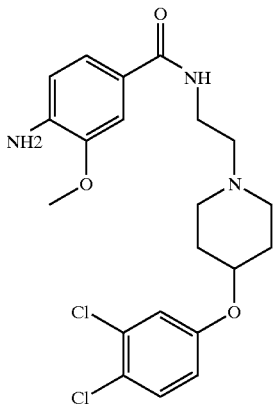
MS: APC1 (+ve) BP 438.
EXAMPLE 175
N-{2-[4-(3,4-Dichlorophenoxy)-1-piperidinyl]ethyl}-3-fluoro-4-methoxybenzamide
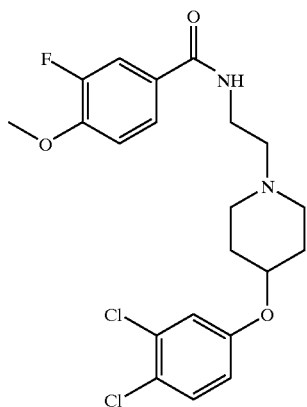
MS: APC1 (+ve) BP 441.
EXAMPLE 176
5-Bromo-N-{2-[4-(3,4-dichlorophenoxy)-1-piperidinyl]ethyl}-2-furamide
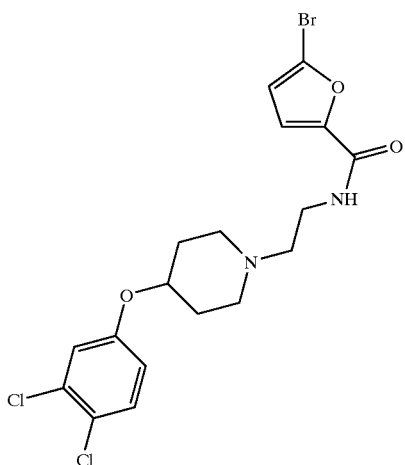
MS: APC1 (+ve) BP 463.
EXAMPLE 177
N-{2-[4-(3,4-Dichlorophenoxy)-1-piperidinyl]ethyl}-3-methyl-2-furamide
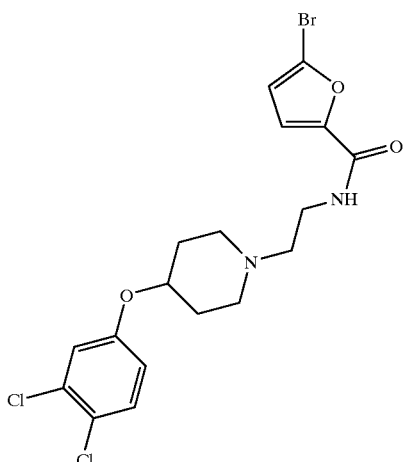
MS: APC1 (+ve) BP 397.

EXAMPLE 178
N-{2-[4-(3,4-Dichlorophenoxy)-1-piperidinyl]ethyl}-4,5-dimethyl-2-furamide
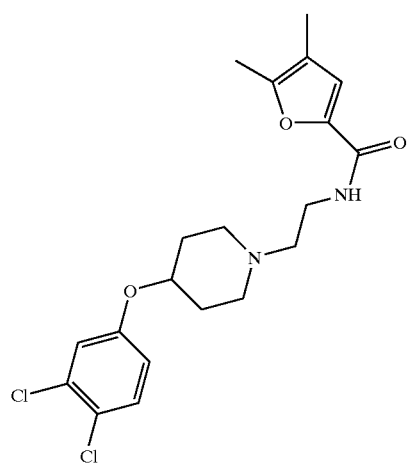
MS: APC1 (+ve) BP 411.
EXAMPLE 179
N-{2-[4-(3,4-Dichlorophenoxy)-1-piperidinyl]ethyl}-7-ethoxy-1-benzofuran-2-carboxamide
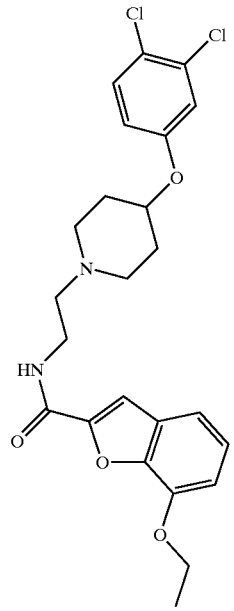
MS: APC1 (+ve) BP 477.
EXAMPLE 180
N-{2-[4-(3,4-Dichlorophenoxy)-1-piperidinyl]ethyl}-5-methoxy-1-benzofuran-2-carboxamide
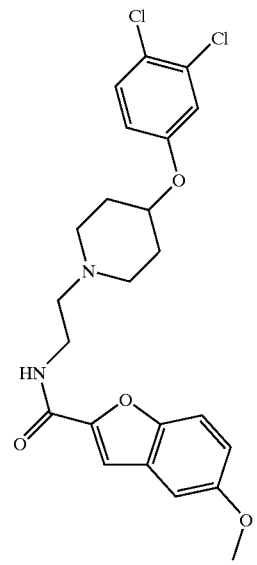
MS: APC1 (+ve) BP 463.
EXAMPLE 181
N-{2-[4-(3,4-Dichlorophenoxy)-1-piperidinyl]ethyl}-7-methoxy-1-benzofuran-2-carboxamide
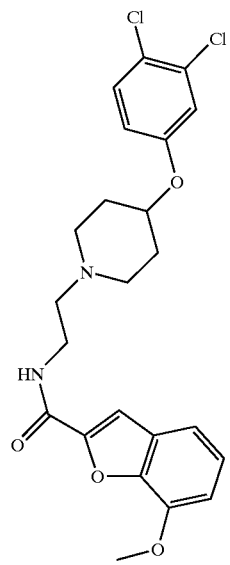
MS: APC1 (+ve) BP463.

EXAMPLE 182
N-{2-[4-(3,4-Dichlorophenoxy)-1-piperidinyl]ethyl}-2-(4-fluorophenyl)acetamide
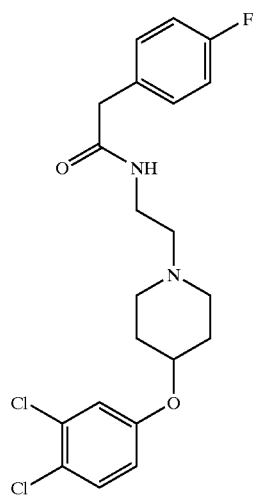
MS: APC1 (+ve) BP 425.
EXAMPLE 183
N-{2-[4-(3,4-Dichlorophenoxy)-1-piperidinyl]ethyl}-2-(2-methoxyphenyl)acetamide
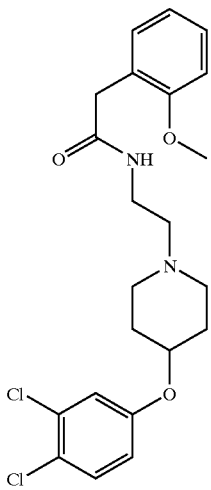
MS: APC1 (+ve) BP 437.
EXAMPLE 184
N-{2-[4-(3,4-Dichlorophenoxy)-1-piperidinyl]ethyl}-2-(3-methylphenyl)acetamide
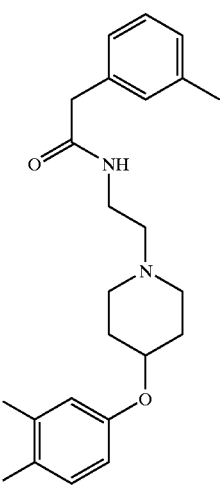
MS: APC1 (+ve) BP421.
EXAMPLE 185
N-{2-[4-(3,4-Dichlorophenoxy)-1-piperidinyl]ethyl}-2-(2-methylphenyl)acetamide
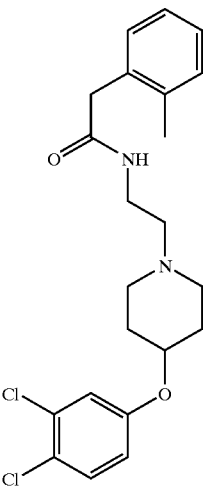
MS: APC1 (+ve) BP 421.

EXAMPLE 186
2-(3-Bromophenyl)-N-{2-[4-(3,4-dichlorophenoxy)-1-piperidinyl]ethyl}acetamide
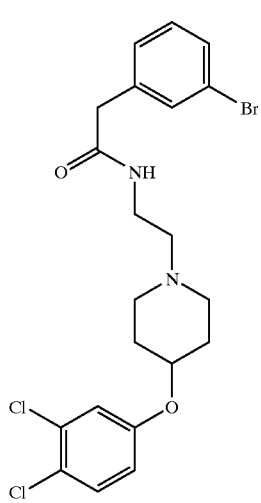
MS: APCl (+ve) BP 487.
EXAMPLE 187
2-(2-Chlorophenyl)-N-{2-[4-(3,4-dichlorophenoxy)-1-piperidinyl]ethyl}acetamide
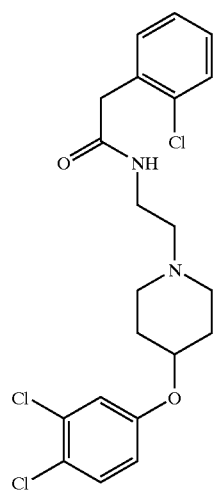
MS: APCl (+ve) BP 441.
EXAMPLE 188
2-(4-Chlorophenyl)-N-{2-[4-(3,4-dichlorophenoxy)-1-piperidinyl]ethyl}acetamide
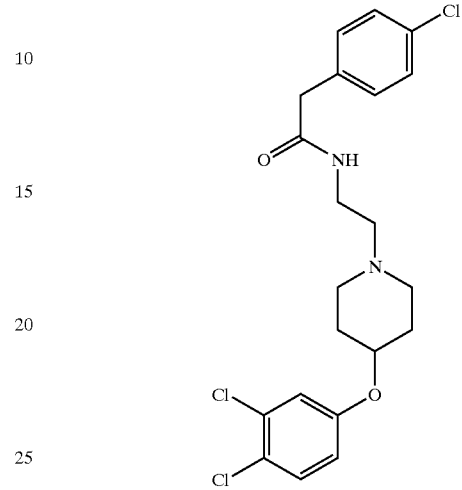
MS: APCl (+ve) BP 443.
EXAMPLE 189
N-{2-[4-(3,4-Dichlorophenoxy)-1-piperidinyl]ethyl}-2-[2-(trifluoromethyl)phenyl]acetamide
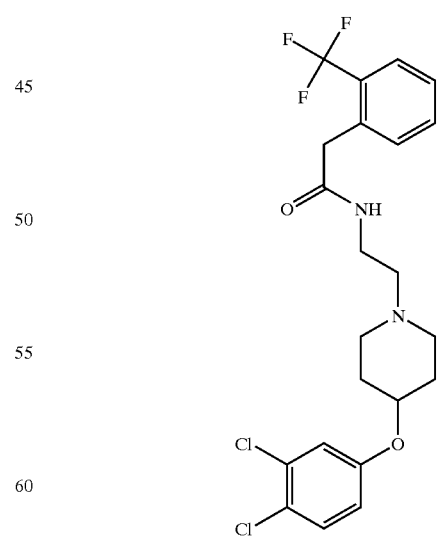
MS: APCl (+ve) BP 475.

EXAMPLE 190
2-(3-Chlorophenyl)-N-{2-[4-(3,4-dichlorophenoxy)-1-piperidinyl]ethyl}acetamide
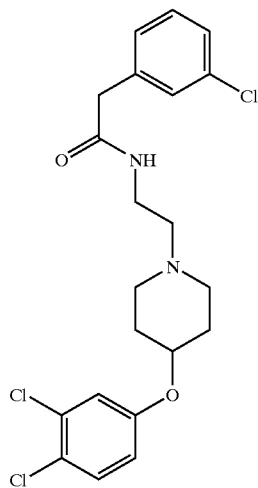
MS: APC1 (+ve) BP441.
EXAMPLE 191
N-{2-[4-(3,4-Dichlorophenoxy)-1-piperidinyl]ethyl}-2-(3,4-dimethoxyphenyl)acetamide
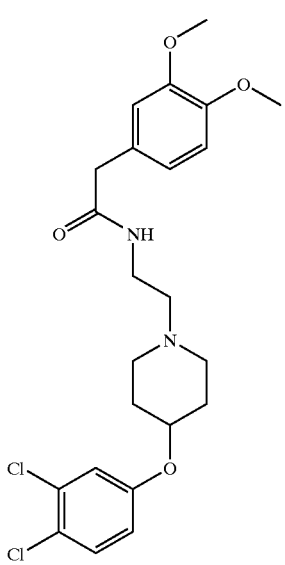
MS: APC1 (+ve) BP467.
EXAMPLE 192
N-{2-[4-(3,4-Dichlorophenoxy)-1-piperidinyl]ethyl}-2-(4-methoxyphenyl)acetamide
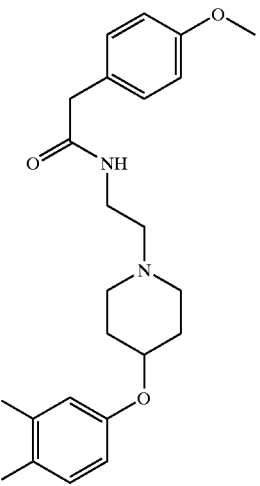
MS: APC1 (+ve) BP 437.
EXAMPLE 193
N-{2-[4-(3,4-Dichlorophenoxy)-1-piperidinyl]ethyl}-2-(3,4-dichlorophenyl)acetamide
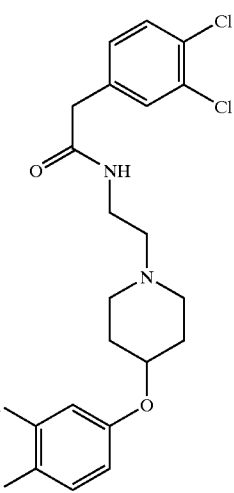
MS: APC1 (+ve) BP 477.

EXAMPLE 194
N-{2-[4-(3,4-Dichlorophenoxy)-1-piperidinyl]ethyl}-2-(3-fluoro-4-methoxyphenyl)acetamide
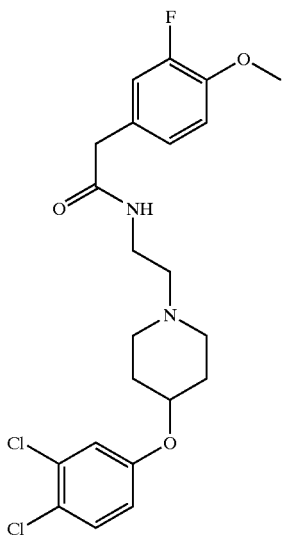
MS: APC1 (+ve) BP 455.
EXAMPLE 195
N-{2-[4-(3,4-Dichlorophenoxy)-1-piperidinyl]ethyl}-2-(4-ethoxyphenyl)acetamide
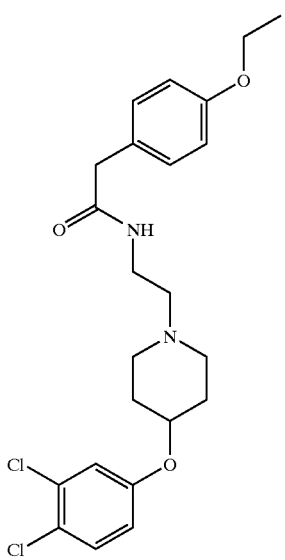
MS: APC1 (+ve) BP 451.
EXAMPLE 196
2-(1,3-Benzodioxol-5-yl)-N-{2-[4-(3,4-dichlorophenoxy)-1-piperidinyl]ethyl}acetamide
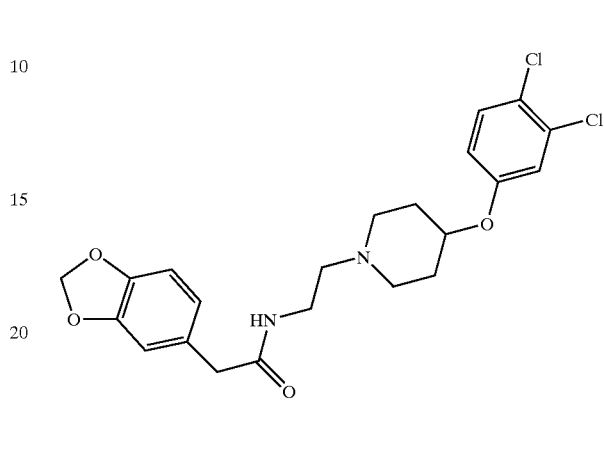
MS: APC1 (+ve) BP451.
EXAMPLE 197
N-{2-[4-(3,4-Dichlorophenoxy)-1-piperidinyl]ethyl}-2-[4-(dimethylamino)phenyl]acetamide
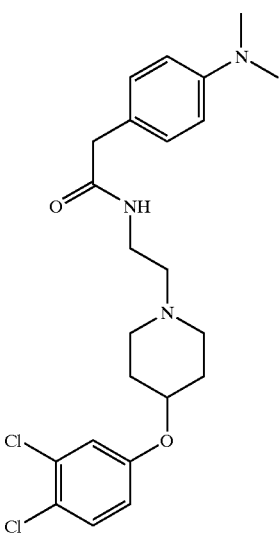
MS: APC1 (+ve) BP 450.

EXAMPLE 198
N-{2-[4-(3,4-Dichlorophenoxy)-1-piperidinyl]ethyl}-2-(4-methylphenyl)acetamide
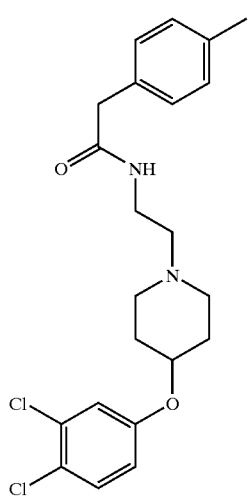
MS: APC1 (+ve) BP 421.
EXAMPLE 199
N-{2-[4-(3,4-Dichlorophenoxy)-1-piperidinyl]ethyl}-2-(3,4-difluorophenyl)acetamide
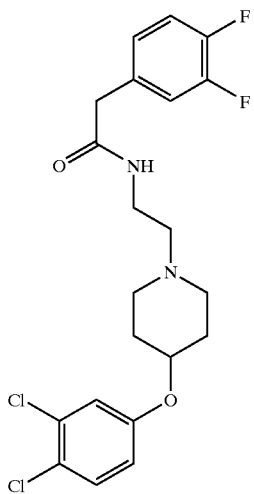
MS: APC1 (+ve) BP 443.
EXAMPLE 200
N-{2-[4-(3,4-Dichlorophenoxy)-1-piperidinyl]ethyl}-2-(3-methoxyphenyl)acetamide
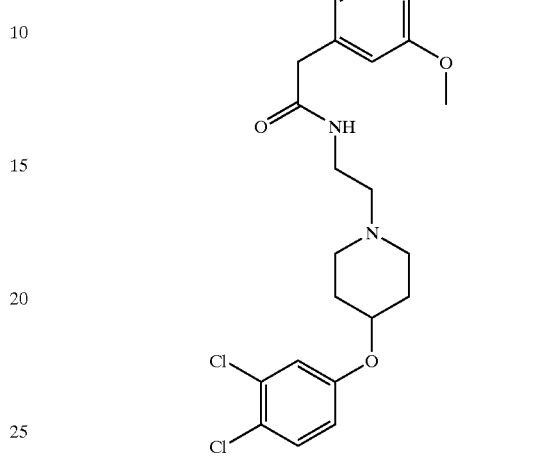
MS: APC1 (+ve) BP 437.
EXAMPLE 201
N-{2-[4-(3,4-Dichlorophenoxy)-1-piperidinyl]ethyl}-4-phenylbutanamide
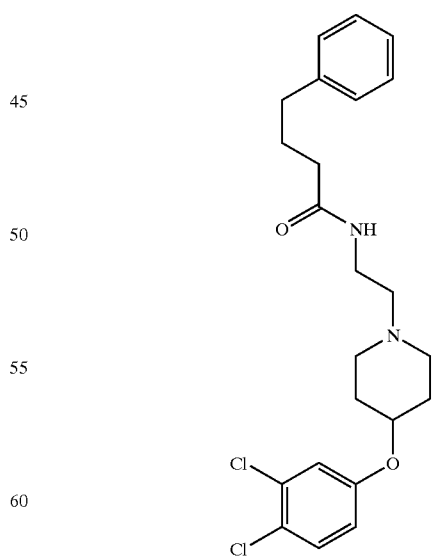
MS: APC1 (+ve) BP 435.

EXAMPLE 202

N-{2-[4-(3,4-Dichlorophenoxy)-1-piperidinyl]ethyl}-3-phenylpropanamide

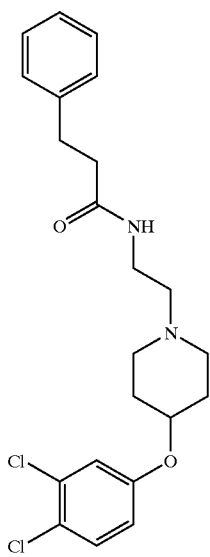

MS: APC1 (+ve) BP 421.

EXAMPLE 203

N-{2-[4-(3,4-Dichlorophenoxy)-1-piperidinyl]ethyl}-3-(3-methoxyphenyl)propanamide

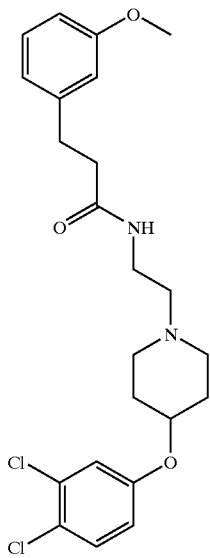

MS: APC1 (+ve) BP 451.

EXAMPLE 204

2-Amino-N-{2-[4-(3,4-dichlorophenoxy)-1-piperidinyl]ethyl}-1,3-thiazole-4-carboxamide

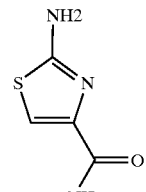

MS: APC1 (+ve) BP 416.

EXAMPLE 205

2-(Acetylamino)-N-{2-[4-(3,4-dichlorophenoxy)-1-piperidinyl]ethyl}-1,3-thiazole-4-carboxamide

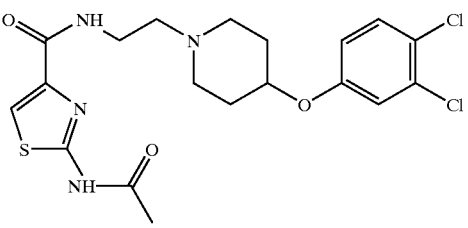

MS: APC1 (+ve) BP 457.

EXAMPLE 206

N-{2-[4-(3,4-Dichlorophenoxy)-1-piperidinyl]ethyl}-2-(4-pyridinyl)-1,3-thiazole-4-carboxamide

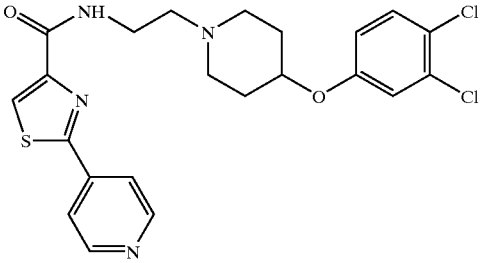

MS: APC1 (+ve) BP 477.

EXAMPLE 207

N-{2-[4-(3,4-Dichlorophenoxy)-1-piperidinyl]ethyl}-2,4-dimethyl-1,3-thiazole-5-carboxamide

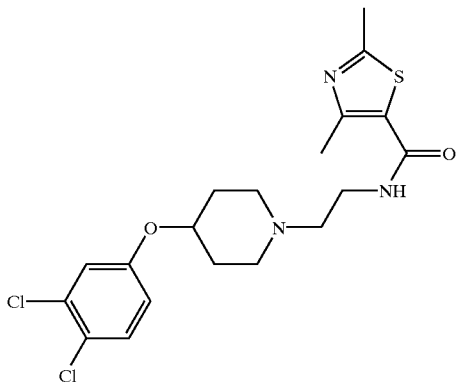

MS: APC1 (+ve) BP 428.

EXAMPLE 208

N-{2-[4-(3,4-Dichlorophenoxy)-1-piperidinyl]ethyl}-2,5-dimethyl-1,3-oxazole-4-carboxamide

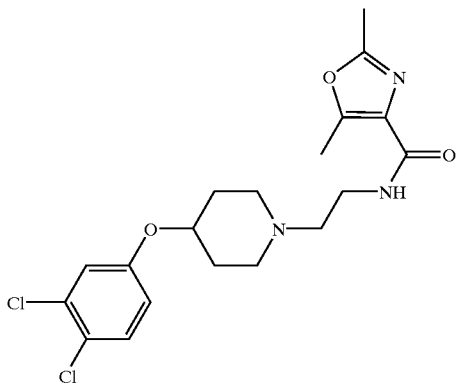

MS: APC1 (+ve) BP 412.

EXAMPLE 209

N-{2-[4-(3,4-Dichlorophenoxy)-1-piperidinyl]ethyl}-1H-imidazole-4-carboxamide

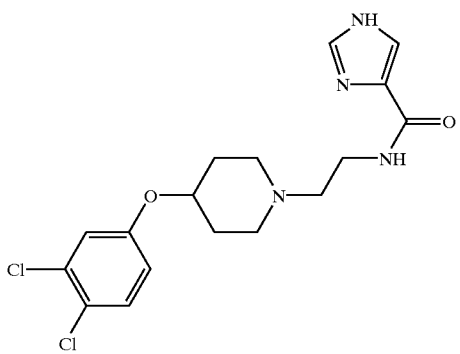

MS: APC1 (+ve) BP 385.

EXAMPLE 210

N-{2-[4-(3,4-Chlorophenoxy)-1-piperidinyl]ethyl}-3-methoxybenzamide hydrochloride

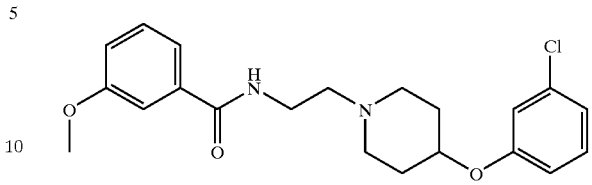

(i) 2-[4-(3,4-Dichlorophenoxy)-1-piperidinyl]ethylamine trifluoroacetate

Prepared by the method of Example 1 steps (i) to (iv) using 3-chlorophenol to give the product as an oil (0.5 g) which was used directly in the next step without further purification.

(ii) N-{2-[4-(3,4-Chlorophenoxy)-1-piperidinyl]ethyl}-3-methoxybenzamide hydrochloride The product of step (i) above (0.3 g) was dissolved in dichloromethane (490 ml), triethylamine (4 equiv) and 3-methoxybenzoyl chloride (1 equiv) were added. After 72 hours at room temperature, water was added, the organic phase separated, dried and concentrated to a gum. The product was dissolved in dichloromethane and treated with 1.0M ethereal hydrogen chloride solution to give the titled product as a solid (0.1 g).

Melting point: 175–176° C.

MS: APCI(+ve): 389 (M+H).

$^1$H NMR: δ(DMSO) 8.87 (t, 1H), 7.5 (m, 2H), 7.42 (m, 1H), 7.32 (m, 1H), 7.13 (m, 2H), 6.98 (m, 2H), 4.82 (m, 1/2H), 4.61 (m, 1/2H), 3.81 (s, 3H), 3.69 (m, 3H), 3.68 (m, 3H), 3.47 (m, 1H), 3.13–3.22 (m, 4H), 2.27 (m, 1H), 2.14 (m, 1H), 2.03 (m, 1H), 1.90 (m, 1H).

EXAMPLE 211

N-{3-[4-(3,4-Dichlorophenoxy)-1-piperidinyl]propyl}-1-methyl-1H-pyrazolo[3,4-d]pyrimidin-4-amine

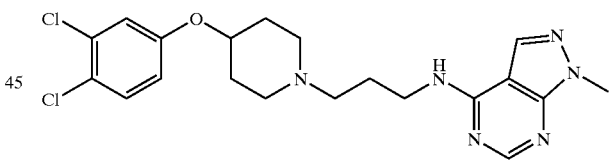

(i) 2-{3-[4-(3,4-Dichlorophenoxy)-1-piperidinyl]propyl}-1H-isoindole-1,3(2H)-dione A solution of the product from Example 1 step (ii) (2.0 g), 2-(3-bromopropyl)-1H-isoindole-1,3(2H)-dione (1.61 g) and triethylamine (2.5 ml) in dichloromethane (40 ml) was heated under reflux for 48 h. The reaction mixture was partitioned between ethyl acetate/water, the organic layer dried and evaporated under reduced pressure. Purification was by chromatography eluting with 4% methanol/dichloromethane. Yield 0.839 g MS: APCI(+ve) 433 (M+1).

(ii) 3-[4-(3,4-Dichlorophenoxy)-1-piperidinyl]propylamine, dihydrochloride salt

The product from step (i) (0.83 g) and hydrazine hydrate (0.1 ml) in ethanol was heated under reflux for 6 h. The precipitate was filtered off and partitioned between 2M hydrochloric acid and dichloromethane, the solid was filtered off and the aqueous layer basified with aqueous potassium hydroxide solution and extracted with dichloromethane. The organic layer was dried, evaporated under reduced pressure and the dihydrochloride salt formed using ethereal hydrogen chloride. Yield 0.28 g $^1$H NMR: δ(DMSO-d$_6$) 11.11 (br s, 1H), 8.13 (br s, 3H), 7.56 (d, 1H), 7.37 (s, 1H), 7.10–7.06 (br m, 1H), 4.84 (br s, 0.5H), 4.65 (br s, 0.5H), 3.60–2.90 (m, 8H), 2.24–2.01 (m, 6H).

(iii) N-{3-[4-(3,4-Dichlorophenoxy)-1-piperidinyl]propyl}-1-methyl-1H-pyrazolo[3,4-d]pyrimidin-4-amine The product from step (ii) (0.08 g), 4-chloro-1-methyl-1H-pyrazolo[3,4-d]pyrimidine (0.054 g) and diisopropylethylamine (0.082 g) in 1-methyl-2-pyrrolidinone (2 ml) was heated at 50° C. for 3 h. The reaction mixture was diluted with ethyl acetate and washed with water. The organic layer was dried and the solvent removed under reduced pressure. Purification was by chromatography eluting with 9% methanol/dichloromethane. Yield 0.052 g MS: APCI(+ve) 435 (M+1).

$^1$H NMR: δ(DMSO-d$_6$) 8.25–8.22 (m, 2H), 8.07 (s, 1H), 7.49 (d, 1H), 7.25 (d, 1H), 6.9 (dd, 1H), 4.46–4.42 (m, 1H), 3.88 (s, 3H), 3.49 (q, 2H), 2.70–2.66 (m, 2H), 2.40–2.36 (m, 2H), 2.27–2.22 (m, 2H), 1.92–1.88 (m, 2H), 1.81–1.74 (m, 2H), 1.62–1.59 (m, 2H).

Melting point: 120–124° C.

EXAMPLES 212–255

The product from Example 211 step (ii) (1.5 mg), the appropriate activated halo aromatic (1.25 equivalents), diisopropylethylamine (10 equivalents) in 1-methyl-2-pyrrolidinone (0.15 ml) were heated at 100° C. for 24 h. The reaction mixture was evaporated to dryness and the residue dissolved in dimethylsulphoxide (0.4 ml).

EXAMPLE 212

N-{3-[4-(3,4-Dichlorophenoxy)-1-piperidinyl]propyl}-2,6-dimethoxy-4-pyrimidinamine

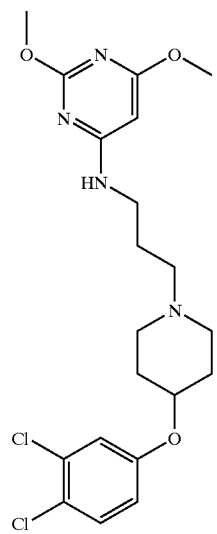

MS: APCI(+ve) 441 (M+1).

EXAMPLE 213

N~4~-{3-[4-(3,4-Dichlorophenoxy)-1-piperidinyl]propyl}-N~2~,N~2~-dimethyl-2,4-pyrimidinediamine

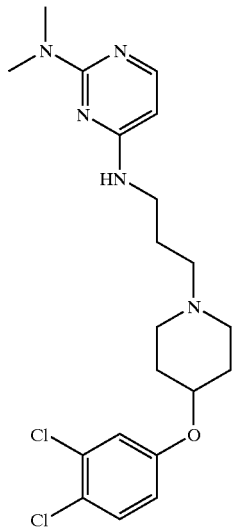

MS: APCI(+ve) 424 (M+1).

EXAMPLE 214

N-{3-[4-(3,4-Dichlorophenoxy)-1-piperidinyl]propyl}-2-[(methylsulfanyl)methyl]-4-pyrimidinamine

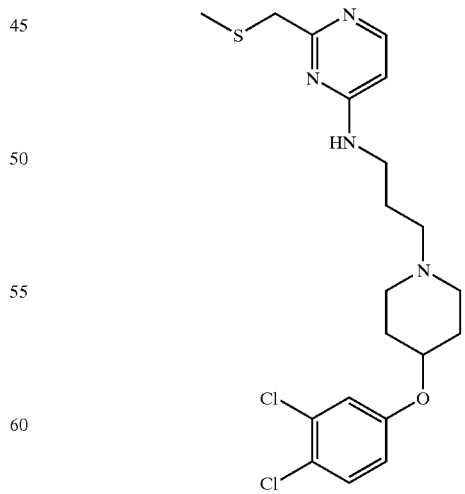

MS: APCI(+ve) 441 (M+1).

EXAMPLE 215

N-{3-[4-(3,4-Dichlorophenoxy)-1-piperidinyl]propyl}-2-(methylsulfanyl)-6-(trifluoromethyl)-4-pyrimidinamine

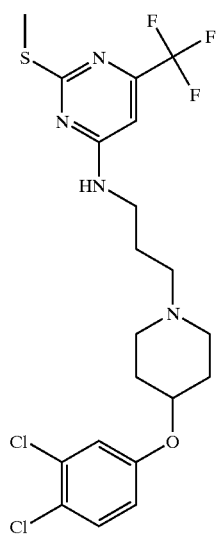

MS: APCI(+ve) 495 (M+1).

EXAMPLE 216

N-{3-[4-(3,4-Dichlorophenoxy)-1-piperidinyl]propyl}-5-methoxy-2-(methylsulfanyl)-4-pyrimidinamine

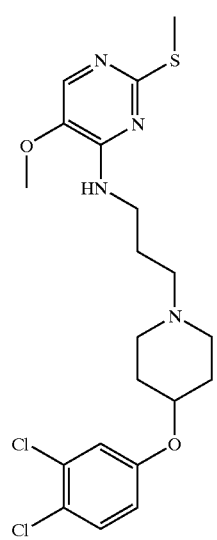

MS: APCI(+ve) 457 (M+1).

EXAMPLE 217

N-{3-[4-(3,4-Dichlorophenoxy)-1-piperidinyl]propyl}-6-methyl-2-(methylsulfanyl)-4-pyrimidinamine

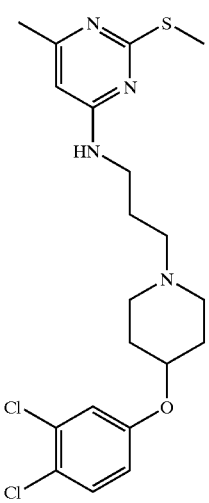

MS: APCI(+ve) 441 (M+1).

EXAMPLE 218

N-{3-[4-(3,4-Dichlorophenoxy)-1-piperidinyl]propyl}-5-methoxy-2-methyl-4-pyrimidinamine

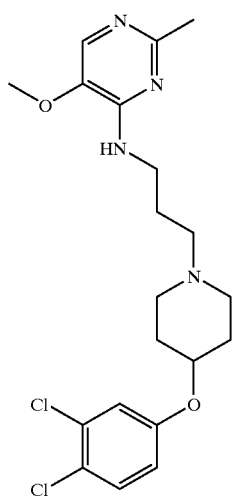

MS: APCI(+ve) 425 (M+1).

EXAMPLE 219

N-{3-[4-(3,4-Dichlorophenoxy)-1-piperidinyl]propyl}-2-(ethylsulfanyl)-6-methyl-4-pyrimidinamine

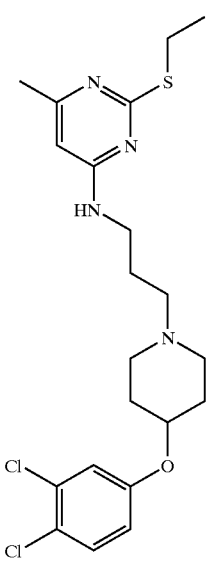

MS: APCI(+ve) 455 (M+1).

EXAMPLE 220

N~2~-Cyclopropyl-N~4~-{3-[4-(3,4-dichlorophenoxy)-1-piperidinyl]propyl}-2,4-pyrimidinediamine

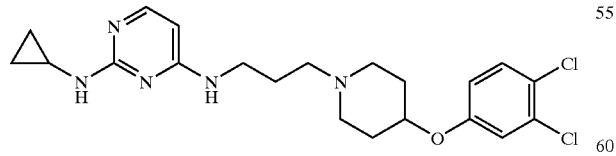

MS: APCI(+ve) 436 (M+1).

EXAMPLE 221

2-{[4-({3-[4-(3,4-Dichlorophenoxy)-1-piperidinyl]propyl}amino)-2-pyrimidinyl]amino}-1-ethanol

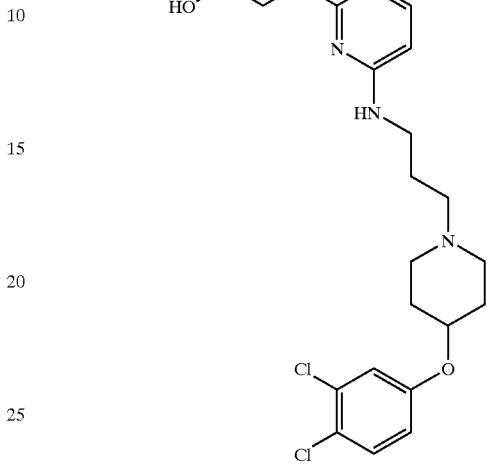

MS: APCI(+ve) 440 (M+1).

EXAMPLE 222

2-[[4-({3-[4-(3,4-Dichlorophenoxy)-1-piperidinyl[propyl}amino)-2-pyrimidinyl](methyl)amino]-1-ethanol

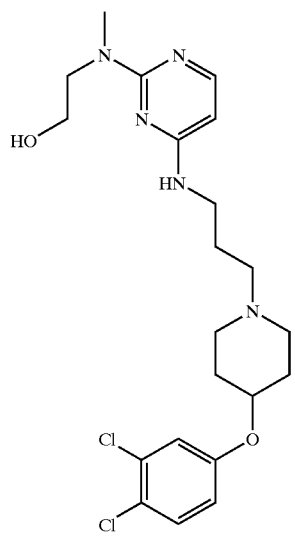

MS: APCI(+ve) 454 (M+1).

EXAMPLE 223

N-{3-[4-(3,4-Dichlorophenoxy)-1-piperidinyl]propyl}-2-(methylsulfanyl)-4-pyrimidinamine

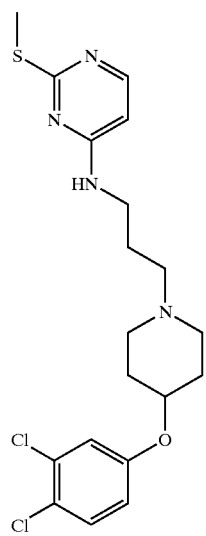

MS: APCI(+ve) 427 (M+1).

EXAMPLE 224

N~4~-{3-[4-(3,4-Dichlorophenoxy)-1-piperidinyl]propyl}-6-methyl-2,4-pyrimidinediamine

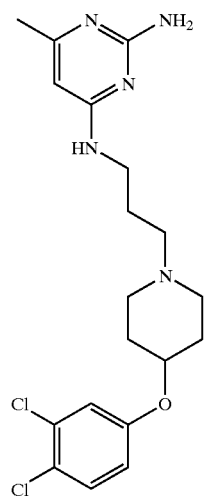

MS: APCI(+ve) 410 (M+1).

EXAMPLE 225

N~4~-{3-[4-(3,4-Dichlorophenoxy)-1-piperidinyl]propyl}-N~2~,6-dimethyl-2,4-pyrimidinediamine

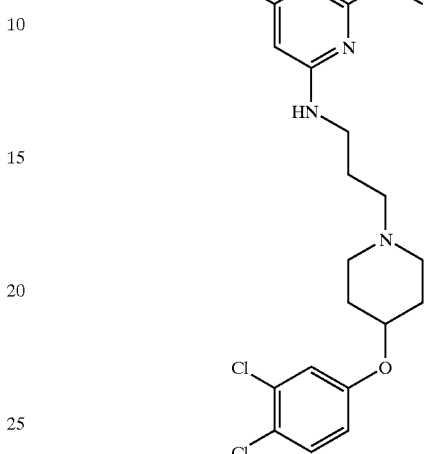

MS: APCI(+ve) 424 (M+1).

EXAMPLE 226

N-{3-[4-(3,4-Dichlorophenoxy)-1-piperidinyl]propyl}-4-phenyl-2-pyrimidinamine

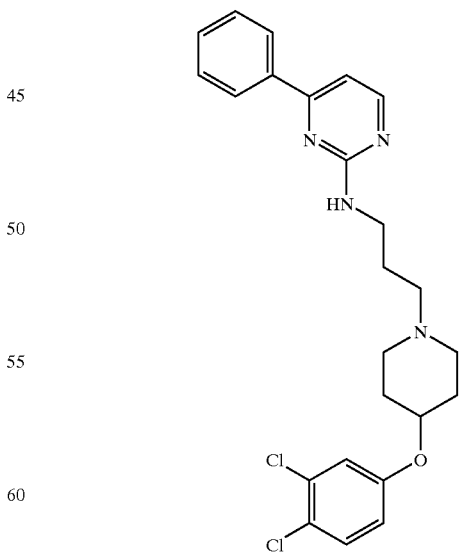

MS: APCI(+ve) 457 (M+1).

EXAMPLE 227

N~2~-{3-[4-(3,4-Dichlorophenoxy)-1-piperidinyl]propyl}-5-fluoro-2,4-pyrimidinediamine

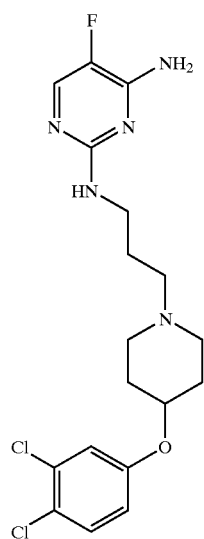

MS: APCI(+ve) 414 (M+1).

EXAMPLE 228

N~2~-{3-[4-(3,4-Dichlorophenoxy)-1-piperidinyl]propyl}-N~4~,N~4~,6-trimethyl-2,4-pyrimidinediamine

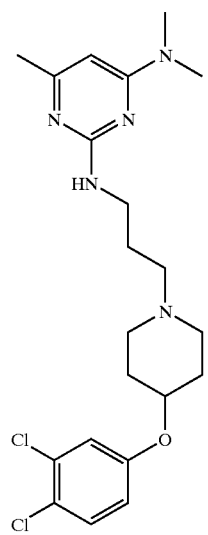

MS: APCI(+ve) 438 (M+1).

EXAMPLE 229

N-{3-[4-(3,4-Dichlorophenoxy)-1-piperidinyl]propyl}-4-(trifluoromethyl)-2-pyrimidinamine

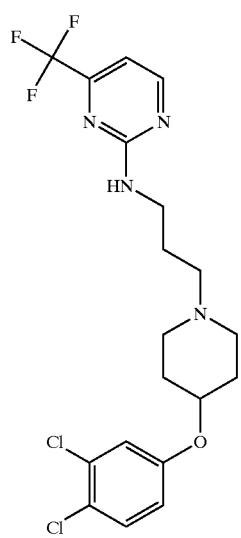

MS: APCI(+ve) 449 (M+1).

EXAMPLE 230

N-{3-[4-(3,4-Dichlorophenoxy)-1-piperidinyl]propyl}-4-(propylsulfanyl)-2-pyrimidinamine

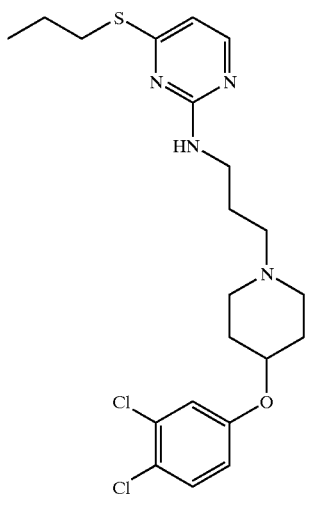

MS: APCI(+ve) 455 (M+1).

EXAMPLE 231

N~2~-{3-[4-(3,4-Dichlorophenoxy)-1-piperidinyl]propyl}-N~4~-phenyl-2,4-pyrimidinediamine

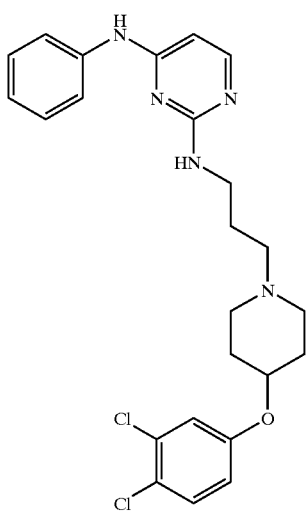

MS: APCI(+ve) 472 (M+1).

EXAMPLE 232

N~2~-{3-[4-(3,4-Dichlorophenoxy)-1-piperidinyl]propyl}-N~4~,6-dimethyl-2,4-pyrimidinediamine

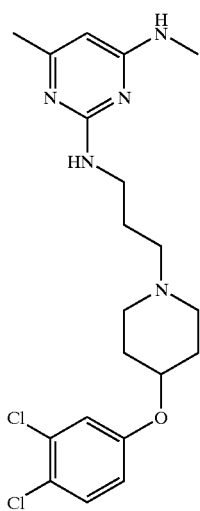

MS: APCI(+ve) 424 (M+1).

EXAMPLE 233

N-{3-[4-(3,4-Dichlorophenoxy)-1-piperidinyl]propyl}[1,8]naphthyridin-2-amine

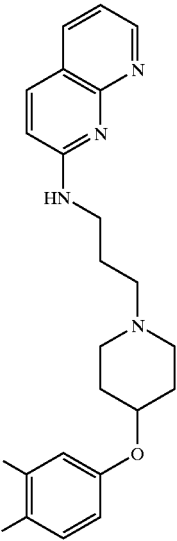

MS: APCI(+ve) 431 (M+1).

EXAMPLE 234

2-{[2-({3-[4-(3,4-Dichlorophenoxy)-1-piperidinyl]propyl}amino)-4-pyrimidinyl]amino}-1-ethanol

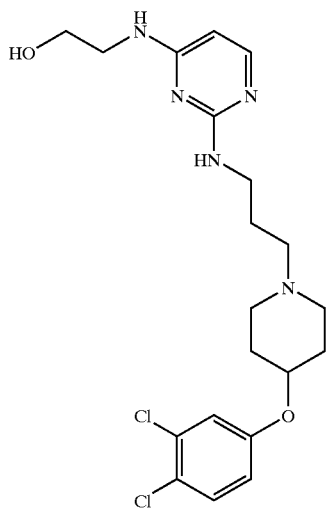

MS: APCI(+ve) 440 (M+1).

EXAMPLE 235
2-[[2-({3-[4-(3,4-Dichlorophenoxy)-1-piperidinyl]propyl}amino)-4-pyrimidinyl](methyl)amino]-1-ethanol
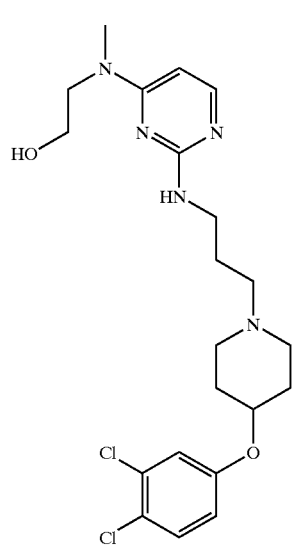
MS: APCI(+ve) 454 (M+1).
EXAMPLE 236
N-{3-[4-(3,4-Dichlorophenoxy)-1-piperidinyl]propyl}-4-(3-pyridinyl)-2-pyrimidinamine
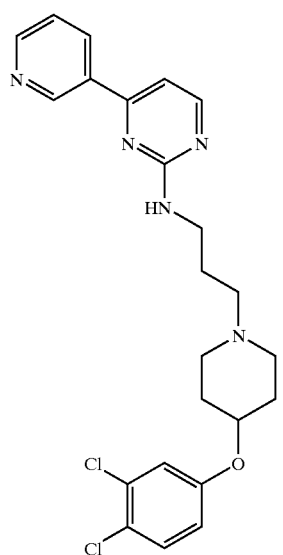
MS: APCI(+ve) 45 (M+1).
EXAMPLE 237
N-{3-[4-(3,4-Dichlorophenoxy)-1-piperidinyl]propyl}-4-(3-thienyl)-2-pyrimidinamine
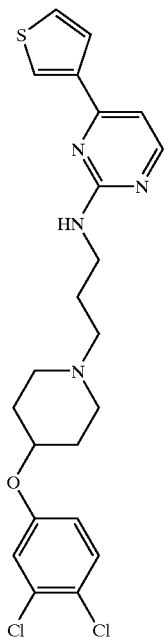
MS: APCI(+ve) 463 (M+1).
EXAMPLE 238
N-{3-[4-(3,4-Dichlorophenoxy)-1-piperidinyl]propyl}-2-pyrimidinamine
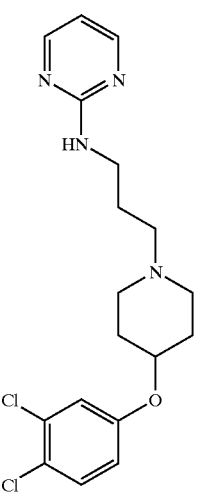
MS: APCI(+ve) 381 (M+1).

EXAMPLE 239
N-{3-[4-3,4-Dichlorophenoxy)-1-piperidinyl]
propyl}-4,6-dimethoxy-2-pyrimidinamine
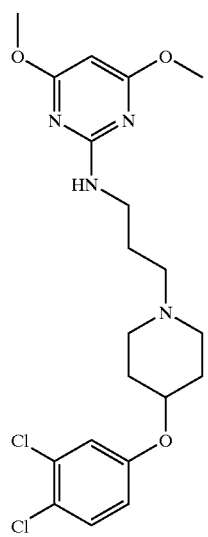
MS: APCI(+ve) 441 (M+1).
EXAMPLE 240
N-{3-[4-(3,4-Dichlorophenoxy)-1-piperidinyl]
propyl}-4-(3-furyl)-2-pyrimidinamine
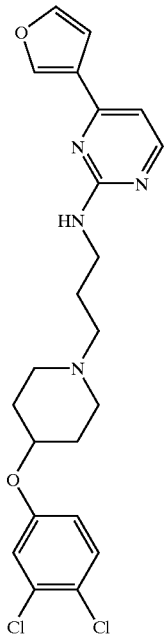
MS: APCI(+ve) 447 (M+1).
EXAMPLE 241
N-{3-[4-(3,4-Dichlorophenoxy)-1-piperidinyl]
propyl}-4-(2-thienyl)-2-pyrimidinamine
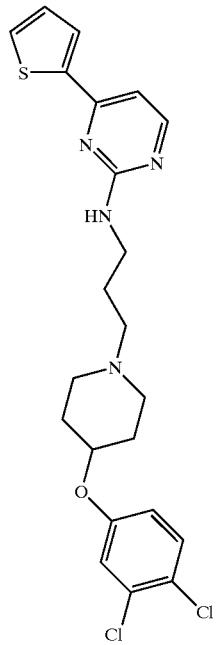
MS: APCI(+ve) 463 (M+1).
EXAMPLE 242
N-{3-[4-(3,4-Dichlorophenoxy)-1-piperidinyl]
propyl}-1H-purin-6-amine
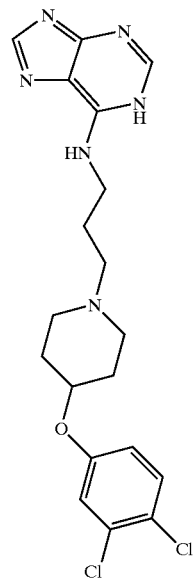
MS: APCI(+ve) 421 (M+1).

EXAMPLE 243

N-{3-[4-(3,4-Dichlorophenoxy)-1-piperidinyl]propyl}-5-methylthieno[2,3-d]pyrimidin-4-amine

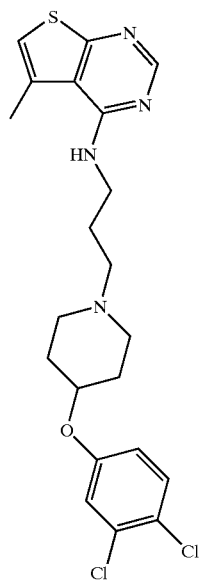

MS: APCI(+ve) 451 (M+1).

EXAMPLE 244

N-{3-[4-(3,4-Dichlorophenoxy)-1-piperidinyl]propyl}-7-methylthieno[3,2-d]pyrimidin-4-amine

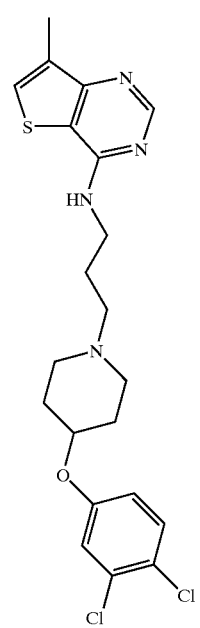

MS: APCI(+ve) 451 (M+1).

EXAMPLE 245

N~7~-{3-[4-(3,4Dichlorophenoxy)-1-piperidinyl]propyl}-5-methyl[1,3]thiazolo[4,5-d]pyrimidine-2,7-diamine

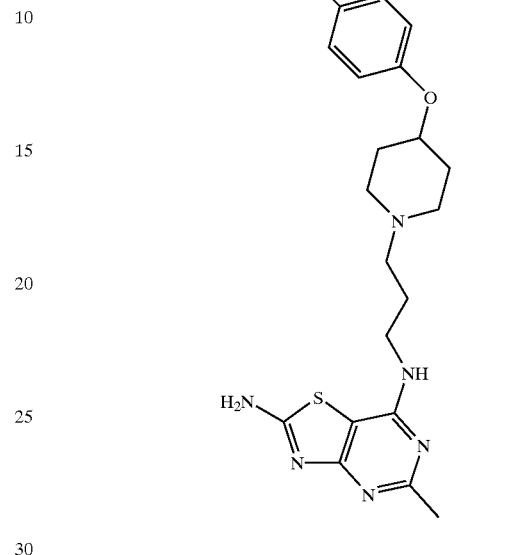

MS: APCI(+ve) 467 (M+1).

EXAMPLE 246

N-{3-[4-(3,4-Dichlorophenoxy)-1-piperidinyl]propyl}-9-methyl-9H-purin-6-amine

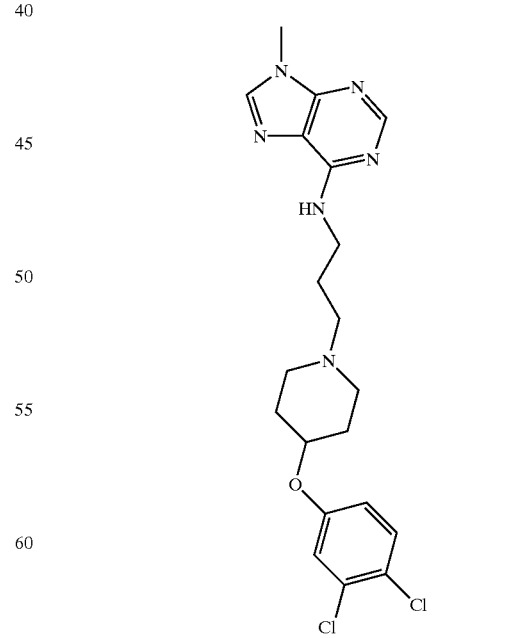

MS: APCI(+ve) 435 (M+1).

EXAMPLE 247
N-{3-[4-(3,4-Dichlorophenoxy)-1-piperidinyl]propyl}-2-pyridinamine
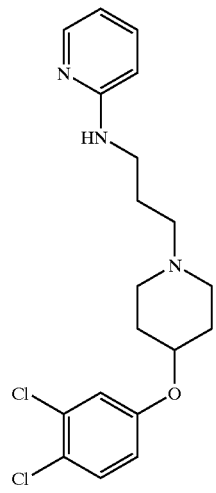
MS: APCI(+ve) 379 (M+1).
EXAMPLE 248
5-Chloro-N-{3-[4-(3,4-dichlorophenoxy)-1-piperidinyl]propyl}-2-pyridinamine
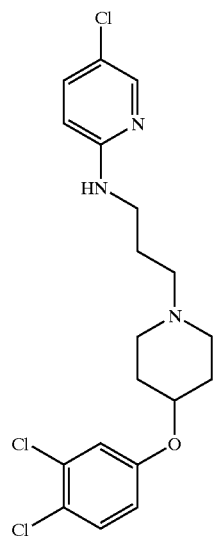
MS: APCI(+ve) 414 (M+1).
EXAMPLE 249
6-Chloro-N-{3-[4-(3,4-dichlorophenoxy)-1-piperidinyl]propyl}-2-pyridinamine
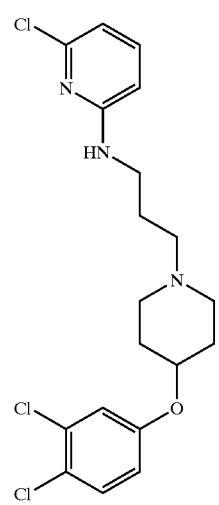
MS: APCI(+ve) 414 (M+1).
EXAMPLE 250
N-{3-[4-(3,4-Dichlorophenoxy)-1-piperidinyl]propyl}-6-methyl-2-pyridinamine
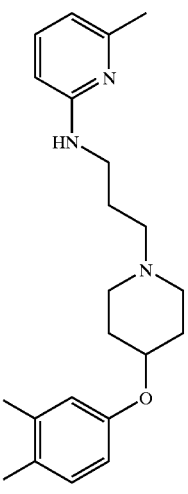
MS: APCI(+ve) 494 (M+1).

EXAMPLE 251

N-{3-[4-(3,4-Dichlorophenoxy)-1-piperidinyl]propyl}-1,3-benzothiazol-2-amine

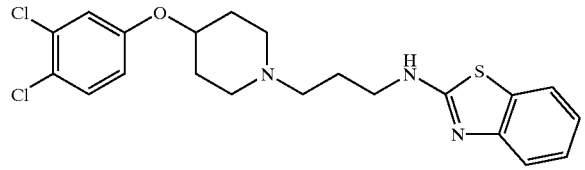

MS: APCI(+ve) 436 (M+1).

EXAMPLE 252

N-{3-[4-(3,4-Dichlorophenoxy)-1-piperidinyl]propyl}-1,3-benzoxazol-2-amine

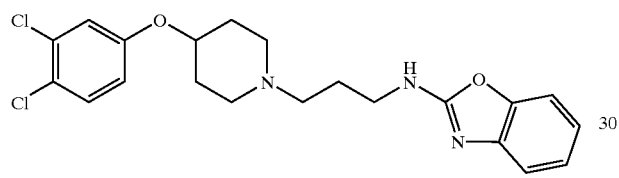

MS: APCI(+ve) 420 (M+1).

EXAMPLE 253

6-Chloro-N-{3-[4-(3,4-dichlorophenoxy)-1-piperidinyl]propyl}-2-pyrazinamine

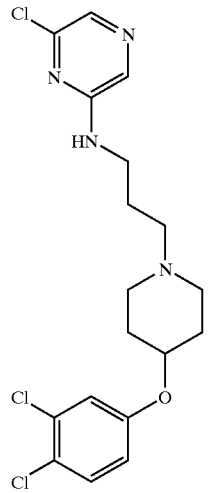

MS: APCI(+ve) 415 (M+1).

EXAMPLE 254

6-Chloro-N-{3-[4-(3,4-dichlorophenoxy)-1-piperidinyl]propyl}-3-pyridazinamine

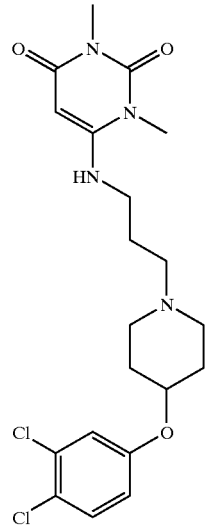

MS: APCI(+ve) 417 (M+1).

EXAMPLE 255

6-({3-[4-(3,4-Dichlorophenoxy)-1-piperidinyl]propyl}amino)-1,3-dimethyl-2,4(1H,3H)-pyrimidinedione MS: APCI(+ve) 441 (M+1).

EXAMPLES 256–292

The product from Example 1 step (iv) (2.07 mg), the appropriate activated halo aromatic (1.25 equivalents), diisopropylethylamine (10 equivalents) in 1-methyl-2-pyrrolidinone (0.15 ml) were heated at 100° C. for 24 h. The reaction mixture was evaporated to dryness and the residue dissolved in dimethylsulphoxide (0.4 ml).

EXAMPLE 256

N-{2-[4-(3,4-Dichlorophenoxy)-1-piperidinyl]ethyl}-2,6-dimethoxy-4-pyrimidinamine

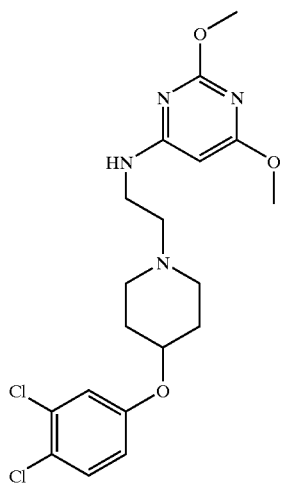

MS: APCI(+ve) 427 (M+1).

EXAMPLE 257

N~4~-{2-[4-(3,4-Dichlorophenoxy)-1-piperidinyl]ethyl}-N~2~,N~2~-dimethyl-2,4-pyrimidinediamine

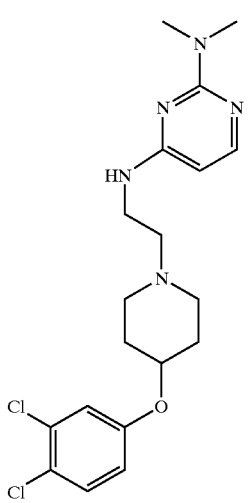

MS: APCI(+ve) 410 (M+1).

EXAMPLE 258

N-{2-[4-(3,4-Dichlorophenoxy)-1-piperidinyl]ethyl}-2-[(methylsulfanyl)methyl]-4-pyrimidinamine

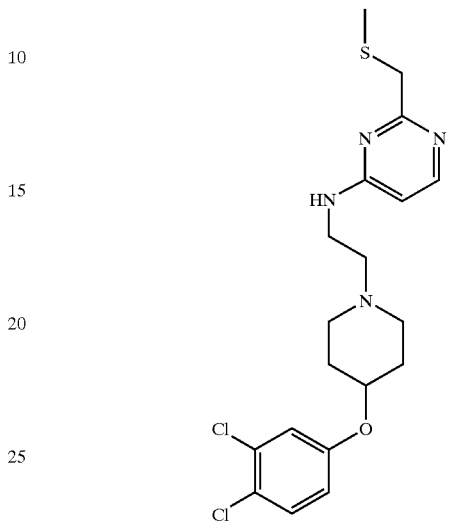

MS: APCI(+ve) 427 (M+1).

EXAMPLE 259

N-{2-[4-(3,4-Dichlorophenoxy)-1-piperidinyl]ethyl}-5-methoxy-2-(methylsulfanyl)-4-pyrimidinamine

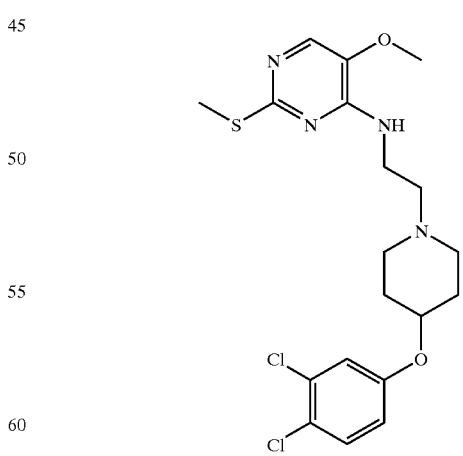

MS: APCI(+ve) 443 (M+1).

EXAMPLE 260

N-{2-[4-(3,4-Dichlorophenoxy)-1-piperidinyl]
ethyl}-6-methyl-2-(methylsulfanyl)-4-
pyrimidinamine

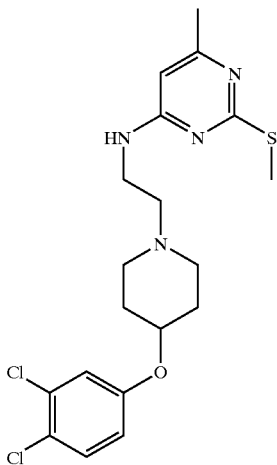

MS: APCI(+ve) 427 (M+1).

EXAMPLE 261

N-{2-[4-(3,4-Dichlorophenoxy)-1-piperidinyl]
ethyl}-5-methoxy-2-methyl-4-pyrimidinamine

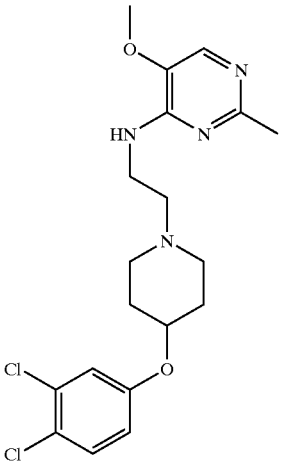

MS: APCI(+ve) 411 (M+1).

EXAMPLE 262

N~4~-{2-[4-(3,4-Dichlorophenoxy)-1-piperidinyl]
ethyl}-6-methyl-N~2~-phenyl-2,4-
pyrimidinediamine

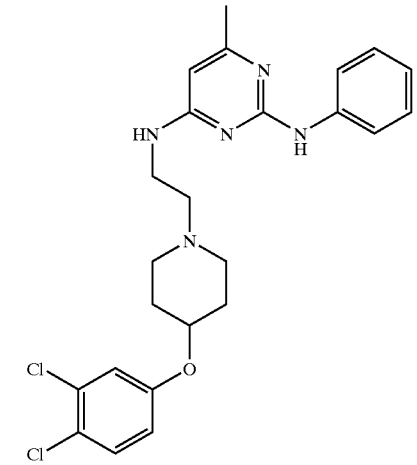

MS: APCI(+ve) 472 (M+1).
Pharmacological Analysis
Calcium flux $[Ca^{2+}]_i$ assay
a) Human Eosinophils Human eosinophils were isolated from EDTA anticoagulated peripheral blood as previously described (Hansel et al., J. Immunol. Methods, 1991, 145, 105–110). The cells were resuspended ($5\times10^6$ ml$^{-1}$) and loaded with 5 μM FLUO-3/AM+Pluronic F127 2.2 μl/ml (Molecular Probes) in low potassium solution (LKS; NaCl 118 mM, MgSO$_4$ 0.8 mM, glucose 5.5 mM, Na$_2$CO$_3$ 8.5 mM, KCl 5 mM, HEPES 20 mM, CaCl$_2$ 1.8 mM, BSA 0.1%, pH 7.4) for one hour at room temperature. After loading, cells were centrifuged at 200 g for 5 min and resuspended in LKS at $2.5\times10^6$ ml$^{-1}$. The cells were then transferred to 96 well FLIPr plates (Poly-D-Lysine plates from Becton Dickinson pre-incubated with 5 μM fibronectin for two hours) at 100 ml/well. The plate was centrifuged at 200 g for 5 min and the cells were washed twice with LKS (200 μl; room temperature).

A compound of the Examples was pre-dissolved in DMSO and added to a final concentration of 0.1% (v/v) DMSO. Assays were initiated by the addition of an A$_{50}$ concentration of eotaxin and the transient increase in fluo-3 fluorescence (I$_{Ex}$=490 nm and I$_{Em}$=520 nm) monitored using a FLIPR (Fluorometric Imaging Plate Reader, Molecular Devices, Sunnyvale, U.S.A.).

b) Human Monocytes

Human monocytes were isolated from EDTA anticoagulated peripheral blood as previously described (Cunoosamy & Holbrook, J. Leukocyte Biology, 1998, S2, 13). Cells were resuspended ($5\times10^6$ ml$^{-1}$) in LKS and loaded with 5 μM FLUO-3/AM+Pluronic F127 2.2 μl/ml (Molecular Probes) for one hour at room temperature. After loading, cells were centrifuged at 200 g for 5 min and resuspended in LKS at $0.5\times10^6$ ml$^{-1}$. The cells were then transferred to 96 well FLIPr plates (Costar). To each well 100 μl of cells were added at a concentration of $0.5\times10^6$ ml$^{-1}$. The plates were centrifuged (200 g; 5 mins; room temperature) to allow the cells to adhere. After centrifugation the cells were washed twice with LKS (200 μl; room temperature).

A compound of the Examples was pre-dissolved in DMSO and added to a final concentration of 0.1% (v/v)

DMSO. Assays were initiated by the addition of an $A_{50}$ concentration of MIP-1α and the transient increase in fluo-3 fluorescence ($I_{Ex}$=490 nm and $I_{Em}$=520 nm) monitored using a FLIPR (Fluorometric Imaging Plate Reader, Molecular Devices, Sunnyvale, U.S.A.).

The compounds of the Examples were found to be antagonists of the eotaxin mediated $[Ca^{2+}]_i$ in human eosinophils and/or antagonists of the MIP-1α mediated $[Ca^{2+}]_i$ in human monocytes.

Human Eosinophil Chemotaxis

Human eosinophils were isolated from EDTA anticoagulated peripheral blood as previously described (Hansel et al., J. Immunol. Methods, 1991, 145, 105–110). The cells were resuspended at $10 \times 10^6$ ml$^{-1}$ in RPMI containing 200 IU/ml penicillin, 200 µg/ml streptomycin sulphate and supplemented with 10% HIFCS, at room temperature.

Eosinophils (700 µl) were pre-incubated for 15 mins at 37° C. with 7 µl of either vehicle or compound (100× required final concentration in 10% DMSO). The chemotaxis plate (ChemoTx, 3 µm pore, Neuroprobe) was loaded by adding 28 µl of a concentration of eotaxin (0.1 to 100 nM) containing a concentration of a compound according to the Examples or solvent to the lower wells of the chemotaxis plate. The filter was then placed over the wells and 25 µl of eosinophil suspension were added to the top of the filter. The plate was incubated for 1 hr at 37° C. in a humidified incubator with a 95% air/5% $CO_2$ atmosphere to allow chemotaxis.

The medium, containing cells that had not migrated, was carefully aspirated from above the filter and discarded. The filter was washed once with phosphate buffered saline (PBS) containing 5 mM EDTA to remove any adherent cells. Cells that had migrated through the filter were pelleted by centrifugation (300×g for 5 mins at room temperature) and the filter removed and the supernatant transferred to each well of a 96-well plate (Costar). The pelleted cells were lysed by the addition of 28 µl of PBS containing 0.5% Triton ×100 followed by two cycles of freeze/thawing. The cell lysate was then added to the supernatant. The number of eosinophils migrating was quantified according to the method of Strath et al., J. Immunol. Methods, 1985, 83, 209 by measuring eosinophil peroxidase activity in the supernatant.

Certain compounds of the Examples were found to be antagonists of the eotaxin mediated human eosinophil chemotaxis.

What is claimed is:

1. A compound of general formula

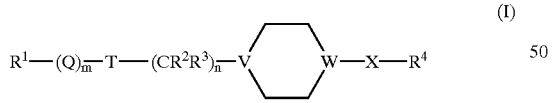

(I)

wherein:
$R^1$ represents a 3- to 10-membered saturated or unsaturated monocyclic ring system containing up to two ring carbon atoms that form carbonyl groups and which comprises 1,2,3 or 4 ring heteroatoms independently selected from nitrogen, oxygen and sulfur, the ring system being optionally substituted by one or more substituents independently selected from halogen atoms, and cyano, nitro, hydroxyl, $C_1$–$C_6$ alkyl, $C_3$–$C_6$ cycloalkyl, $C_1$–$C_6$ alkoxy, $C_1$–$C_6$ alkoxycarbonyl, $C_1$–$C_6$ haloalkyl, $C_1$–$C_6$ haloalkoxy, —NR$^5$R$^6$, $C_3$–$C_6$ cycloalkylamido, $C_1$–$C_6$ alkylthio, $C_1$–$C_6$ alkylthio $C_1$–$C_6$ alkyl, $C_1$–$C_6$ alkylcarbonylamino, —C(O)NR$^7$R$^8$, sulphonamido, (di)$C_1$–$C_6$ alkylsulphonamido, phenyl, phenylamino, nitrophenyl, pyridyl, pyridylthio, benzodioxanyl, thienyl, furanyl, and C(O)R$^9$-substituted $C_1$–$C_6$ alkyl or $C_1$–$C_6$ alkoxy groups;

m is 0 or 1;

Q represents a group $OCH_2$, $C_1$–$C_6$ alkylene or $C_2$–$C_4$ alkenylene;

T represents a group C(O)NH, or when m is 0 and $R^1$ is not optionally substituted pyridinyl then T may additionally be NH, or when m is 1 and Q is $C_1$–$C_4$ alkylene then T may additionally be NH;

n is 1,2,3 or 4;

each $R^2$ independently represents a hydrogen atom or a $C_1$–$C_4$ alkyl group;

each $R^3$ independently represents a hydrogen atom or a $C_1$–$C_4$ alkyl group;

V represents a nitrogen atom;

W represents CH;

X represents an oxygen atom or a group C(O), CH(OH), NH or N($C_1$–$C_6$ alkyl);

$R^4$ represents a phenyl group optionally substituted by one or more substituents independently selected from halogen atoms, and amino, nitro, cyano, sulphonyl, sulphonamido, $C_1$–$C_6$ alkyl, $C_1$–$C_6$ haloalkyl, $C_1$–$C_6$ haloalkoxy and $C_1$–$C_6$ alkylsulphonyl groups;

$R^5$ and $R^6$ each independently represent a hydrogen atom or a $C_2$–$C_6$ alkyl or hydroxy $C_1$–$C_6$ alkyl group, or $R^5$ and $R^6$ together with the nitrogen atom to which they are attached form a 4- to 7-membered saturated heterocyclic ring;

$R^7$ and $R^8$ each independently represent a hydrogen atom or a $C_1$–$C_6$ alkyl group; and $R^9$ represents a hydroxyl or —NR$^7$R$^8$ group;

with the provisions that (a) when m is 0, T is CONH, n is 2, 3 or 4 and each $R^2$ and $R^3$ represents hydrogen, W is CH, X is C(O) or CH(OH) and $R^1$ represents a substituted 3- to 10-membered unsaturated ring system, then the one or more substituents in the ring system do not include hydroxyl, halogen, $C_1$–$C_6$ alkoxy or $C_1$–$C_6$ haloalkoxy, and (b) when X is O, n is 2 or 3 and each $R^2$ and $R^3$ represents hydrogen, m is 0 and T is NH, then $R^1$ does not represent a group

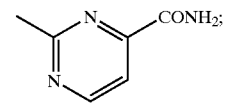

or a pharmaceutically acceptable salt or solvate thereof.

2. A compound according to claim 1, wherein $R^1$ represents a 3- to 10-membered saturated or unsaturated ring system comprising up to two ring carbon atoms that form carbonyl groups and comprising up to 4 ring heteroatoms indpendently selected from nitrogen, oxygen and sulfur, the ring system being optionally substituted by one, two or three substituents independently selected from halogen atoms, and cyano, nitro, hydroxyl, $C_1$–$C_4$ alkyl, $C_3$–$C_6$ cycloalkyl, $C_1$–$C_4$, alkoxy, $C_1$–$C_4$ alkoxycarbonyl, $C_1$–$C_3$ haloalkyl, $C_1$–$C_3$ haloalkoxy, —NR$^5$R$^6$, $C_3$–$C_6$ cycloalkylamino, $C_1$–$C_4$ alkylthio, $C_1$–$C_4$ alkylthio $C_1$–$C_4$ alkyl, $C_1$–$C_4$ alkylcarbonylammno, —C(O)NR$^7$R$^8$, phenyl, phenylamino, notrophenyl, pyridyl, pyridylthio, benzodiaxanyl, thienyl, furanyl and C(O)R$^9$-substituted $C_1$–$C_4$ alkyl or $C_1$–$C_4$ groups.

3. A compound according to claim 1 or claim 2, wherein m is 1 and Q represents a group $OCH_2$, $C_1$–$C_3$ alkylene or $C_2$–$C_3$ alkenylene.

4. A compound according to claim 1 or claim 2, wherein T represents a group C(O)NH.

5. A compound according to claim 1 or claim 2, wherein n is 2 or 3.

6. A compound according to claim 1 or claim 2, wherein X represents an oxygen atom or a group C(O) or NH.

7. A compound according to claim 1 or claim 2, wherein $R^4$ represents a phenyl group optionally substituted by one or two halogen atoms.

8. A process for the preparation of a compound of formula (I) as defined in claim 1 which comprises (i) when T represents a group C(O)NH, reacting a compound of general formula

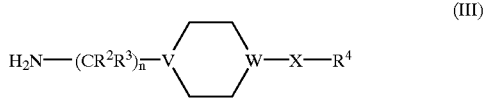

(III)

wherein $L^1$ represents a leaving group and $R^1$, m and Q are as defined in formula (I), with a compound of general formula $$R^1-(Q)_m-COL^1 \quad (II)$$

or an acid addition salt thereof wherein n, $R^2$, $R^3$, V, W, X and $R^4$ are as defined in formula (I); or (ii) when T represents a group NH and m is 0, reacting a compound of general formula $$R^1\text{-}L^3 \quad (VI)$$

Wherein $L^3$ represents a leaving group and $R^1$ is as defined in formula (I), with a compound of formula (III) as defined in (i) above; or (iii) when T represents a group NH, m is I and Q represents $C_1$–$C_4$ alkylene, reacting a compound of general formula $$R^1-(CH_2)_p-CHO \quad (VII)$$

wherin p is 0, 1, 2 or 3 and $R^1$ is as defined informula (I), with a compound of formula (III) as defined in (i) above and optionally after (i), (ii), or (iii) converting the compound of formula (I) to a further compound of formula (I) and/or forming a pharmaceutically acceptable salt or solvate of the compound of formula (I).

9. A compound of formula (I), or a pharmaceutically acceptable salt or solvate thereof, according to claim 1 being selected from:

N-{2-[4-(3,4-Dichlorophenoxy)-1-piperidinyl]ethyl}-2-furamide hydrochloride,

2-[3-}2-[4-(4-Fluorobenzoyl)-1-piperidinyl]ethyl}-2,4-dioxo-3,4-dihydro-1(2H)-quinazolinyl]-N,N-dimethylacetamide hydrochloride, N~7~-{2-[4-(3,4-Dichlorophenoxy)-1-piperidinyl]ethyl}-5-methyl[1,3]thiazolo[4,5-d]pyrimidine-2,7-diamine, 6-Chloro-N-{2-[4-(3,4-dichlorophenoxy)-1-piperidinyl]ethyl}-2-pyrazinamine, 6-Chloro-N-{2-[4-(3,4-dichlorophenoxy)-1-piperidinyl]ethyl}-3-pyridazinamine, 6-({2-[4-(3,4-Dichlorophenoxy)-1-piperidinyl]ethyl}amino)-1,3-dimethyl-2,4(1H,3H)-pyrimidinedione, 3-{2-[4-(3,4-Dichlorophenoxy)-1-piperidinyl]ethyl}-6-methoxy-2,4(1H,3H)-quinazolinedione, N-{2-[4-(3,4-Dichlorophenoxy)-1-pipezidinyl]ethyl}-2-furamide, N-(2-[4-(3,4-Dichlorophenoxy)-1-piperidinyl]ethyl}-2-(methylsulfanyl)nicotinamide, N-{2-[4-(3,4-Dichlorophenoxy)-1-piperidinyl]ethyl}-2-thiophenecarboxamide, N-(2-[4-(3,4-Dichlorophenoxy)-1-piperidinyl]ethyl}-2-quinoxalinecarboxamide, 2-Chloro-N-{2-[4-(3,4-Dichlorophenoxy)-1-piperidinyl]ethyl}nicotinamide, N-{2-[4-(4-Chlorobenzoyl)-1-piperidinyl]ethyl}-2-furamide, N-{2-[4-(4-Chlorobenzoyl)-1-pipendinyl]ethyl}-2-(methylsulfanyl)nicotinamide, N-{2-[4-(4-Chlorobenzoyl)-1-pipendinyl]ethyl}-2-(2,3-dihydro-1,4-benzodioxin-2-yl)-1,3-thiazole-4-carboxamide, N~2~-Cyclopropyl-N~4~-{2-[4-(3,4-dichlorophenoxy)-1-piperidinyl]ethyl}-2,4-pyrimidinediamine, 2-{[4-({2-[4-(3,4-Dichlorophenoxy)-1-piperidinyl]ethyl}amino)-2-pyrimidinyl]amino}-1-ethanol, 2-[[4-({2-[4-(3,4-Dichlorophenoxy)-1-piperidinyl]ethyl}amino)-2-pyrimidinyl](methyl)amino]-1-ethanol, N~4~-{2-[4-(3,4-Dichlorophenoxy)-1-piperidinyl]ethyl}-N~2~-phenyl-2,4-pyrimidinediamine, N-{2-[4-(3,4-Dichlorophenoxy)-1-piperidinyl]ethy}-2-(methylsulfanyl)-4-pyrimidinamine, N~4~-{2-[4-(3,4-Dichlorophenoxy)-1-piperidinyl]ethyl}-N-6-methyl-2,4-pyrimidinediamine, N~4~-{2-[4-(3,4-Dichlorophenoxy)-1-piperidinyl]ethyl}-N~2~,6-dimethyl-2,4-pyrimidinediamine, 2-Chloro-N~4~-cyclopropyl-N~6~-{2-[4-(3,4-dichlorophenoxy)-1-piperidinyl]ethyl}-4,6-pyrimidinediamine, N-{2-[4-(3,4-Dichlorophenoxy)-1-piperidinyl]ethyl}-[4-phenyl-2-pyrimidinamine, N~2~-{2-[4-(3,4-Dichlorophenoxy)-1-piperidinyl]ethyl}-N~4~,N~4~,6-trimethyl-2,4-pyrimidinediamine, N-{2-[4-(3,4-Dichlorophenoxy)-1-pipendinyl]ethyl}-4-(trifluoromethyl)-2-pyrimidinamine, N-{2-[4-(3,4-Dichlorophenoxy)-1-pipendinyl]ethyl}-4-(propylsulfanyl)-2-pyrimidinamine, N~2~-[4-(3,4-Dichlorophenoxy)-1-pipendinyl]ethyl}-N~4~-phenyl-2,4-pyrimidinedamine, N~4~-Cyclopropyl-N~2~-{2-[4-(3,4-dichloraphenoxy)-1-piperidinyl]ethyl}-2,4-pyrimidinamine, N-{2-[4-(3,4-Dichlorophenoxy)-1-pipendinyl]ethyl}-4-(3-pyridinyl)-2-pyrimidinamine, N-{2-[4-(3,4-Dichlorophenoxy)-1-pipendinyl]ethyl}-2-pyrimidinamine, N-{2-[4-(3,4-Dichlorophenoxy)-1-pipendinyl]ethyl}-4,6-dimethoxy-2-pyrimidinamine, N-{2-[4-(3,4-Dichlorophenoxy)-1-piperidinyl]ethyl}-4-(3-furyl)-2-pyrimidinamine, N-{2-[4-(4-Chlorobenzoyl)-1-piperidinyl]ethyl}-2-thiophenecarboxamide, N-{2-[4-(4-Chlorobenzoyl)-1-piperidinyl]ethyl}-2-quinoxalinecarboxamide,

[1-(2-{[(5-Chloro-1,3-dimethyl-1H-pyrazol-4-yl)methyl]
amino}ethyl)-4-piperidinyl](4-chlorophenyl)
methanone,
(4-Chlorophenyl)[1-(2-{[3-nitro-4-(2-pyridinylsulfanyl)
benzyl[amino}ethyl)-4-piperidinyl]methanone,
(4-Chlorophenyl){1-[2-({[5-(3-nitrophenyl)-2-furyl]
methyl}amino)ethyl]-4-piperidinyl]methanone,
(4-Chlorophenyl)[1-(2-{[5-nitro-2-(2-pyridinylsulfanyl)
benzyl]amino}ethyl)-4-piperidinyl]methanone,
6-[({2-4-(4-Chlorobenzoyl)-1-pipendinyl]ethyl}amino)
methyl]-2-(methylsulfanyl)nicotinonitrile,
{1-[2-({[5-Chloro-1-methyl-3-(trifluoromethyl)-1H-
pyrazol-4-yl)methyl}amino)ethyl]-4-piperidinyl}(4-
chlorophenyl)methanone,
(4-Chlorophenyl)[1-(2-{[(4-phenyl-4-piperidinyl)methy]
amino}ethyl)-4-piperidinyl]methanone,
(4-Chlorophenyl)[1-(2-{[(1-phenyl-1H-pyrazol-5-yl)
methyl]amino}ethyl)-4-piperidinyl]methanone,
(4-Chlorophenyl)(1-{2-[(2-pyridinylmethyl)amino]
ethyl}-4-piperidinyl)methanone,
(4-Chlorophenyl)[1-(2-{[(3-methyl-2-thienyl)methyl]
amino}ethyl)-4-piperidinyl]methanone,
[1-(2-{[5-Chloro-1,3-dimethyl-1H-pyrazol-[4-yl)methyl]
amino}ethyl)-4-piperidinyl](4-chlorophenyl]
methanone,
(4-Chlorophenyl)[1-(2-{[(2,6-dichloro-4-pyridinyl)
methyl]amino}ethyl)-4-piperidinyl]methanone,
(4-Chlorophenyl)[1-(2-{[(2-phenyl-1H-imidazol-4-yl)
methyl]amino}ethyl)-4-piperidinyl]methanone,
(4-Chlorophenyl)[1-(2-{[(5-ethyl-2-thienyl)methyl]
amino}ethyl)-4-piperidinyl]methanone,
(4-Chlorophenyl)[1-(2-{[(2-chloro-3-quinolinyl)methyl]
ammo}ethyl)-4-piperidinyl]methanone,
(4-Chlorophenyl)[1-(2-{[(6-methyl-2-pyridinyl)methyl]
amino}ethyl)-4-piperidinyl]methanone,
(4-Chlorophonyl)(1-{2-[(3-quinolinylmethyl)amino
[ethyl}-4-piperidinyl)methanone,
4-[({2-[4-(4-Chlorobenzoyl)-1-piperidinyl]ethyl}amino)
methyl]-1,5-dimethyl-2-phenyl-1,2-dihydro-3H-
pyrazol-3-one,
(4-Chlorophenyl)(1-{2-[(4-pyridinylmethyl)amino]
ethyl}-4-piperidinyl)methanone,
[1-(2-{[(4-Bromo-1H-pyrazol-3-yl)methyl]
amino}ethyl)-4-piperidinyl](4-chlorophenyl)
methanone,
(4-Chlorophenyl)[1-(2-{[(2,4-dimethoxy-5-pyrimidinyl)
methyl]amino}ethyl)-4-piperidinyl]methanone,
5-Bromo-N-{2-[4-(3,4-dichlorophenoxy)-1-piperidinyl]
ethyl}-2-furamide,
N-{2-[4-(3,4-Dichlorophenoxy)-1-pipendinyl]ethyl}-3-
methyl-2-furamide,
N-{2-[4-(3,4-Dichlorophenoxy)-1-pipendinyl]ethyl}-4,5-
dimetyl-2-furamide,
2-Amino-N-{2-[4-(3,4-dichlorophenoxy)-1-piperidinyl]
ethyl}-1,3-thiazole-4-carboxamide,
2-Acetylamino)-N-{2-[4-(3,4-dichlorophenoxy)-1-
piperidinyl]ethyl}-1,3-thiazole-4-carboxamide,
N-{2-[4-(3,4-Dichlorophenoxy)-1-pipendinyl]ethyl}-2-
(4-pyridinyl)-1,3-thiazole-4-carboxamide,
N-{2-[4-(3,4-Dichlorophenoxy)-1-pipendinyl]ethyl}-2,4-
dimethyl-1,3-thiazole-5-carbaxamide,
N-{2-[4-(3,4-Dichlorophenoxy)-1-pipendinyl]ethyl}-2,5-
dimethyl-1,3-oxazole-4-carboxamide,
N-{2-[4-(3,4-Dichlorophenoxy)-1-pipendinyl]ethyl}-1H-
imidazole-4-carboxamide,
N-{3-[4-(3,4-Dichlorophenoxy)-1-piperidinyl]propyl}-2,
6-dimethoxy-4-pyrimidinamine,
N~4~-{3-[4-(3,4-Dichlorophenoxy)-1-piperidinyl]
propyl}-N~2~,N~-2~dimethyl-2,4-pyrimidinediamine,
N-(3-[4-(3,4-Dichlorophenoxy)-1-piperidinyl]propyl}-2-
[(methylsulfanyl)methyl]-4-pyrimidinamine,
N-{3-[4-(3,4-Dichlorophenoxy)-1-piperidinyl]propyl}-2-
(methylsulfanyl)-6-(trifluoromethyl)-4-
pyrimidinamine,
N-{3-[4-(3,4-Dichlorophenoxy)-1-piperidinyl]propyl}-5-
methoxy-2-(methylsulfanyl)-4-pyrimidinamine,
N-{3-[4-(3,4-Diohlorophenoxy)-1-piperidinyl]ropyl}-6-
methyl-2-(methylsulfanyl)-4-pyrimidinamine,
N-{3-[4-(3,4-Dichlorophenoxy)-1-piperidinyl]propyl}-5-
methoxy-2-methyl-4-pyrimidinamine,
N-{3-[4-(3,4-Dichlorophenoxy)-1-piperidinyl]propyl}-2-
(ethylsulfanyl)-6-methyl-4-pyrimidinamine,
N~2~-Cyclopropyl-N~4~-}3-[4-(3,4-dichlorophenoxy)-
1-piperidinyl]propyl}-2,4-pyrimidinediamine,
2-{[4-({3-[4-(3,4-Dichlorophenoxy)-1-piperidinyl]
propyl}amino)-2-pyrimidinyl]amino}-1-ethanol,
2-[[4-({3-[4-(3,4-Dichlorophenoxy)-1-piperidinyl]
propyl}amino)-2-pyrimidinyl](methyl)amino]-1-
ethanol,
N-{3-[4-(3,4-Dichlorophenoxy)-1-piperidinyl]propyl}-2-
(methylsulfanyl)-4-pyrimidinamine,
N~4~-{3-[4-(3,4-Dichlorophenoxy)-1-piperidinyl]
propyl}-6-methyl-2,4-pyrimidinamine,
N~4~-{3-[4-(3,4-Dichlorophenoxy)-1-piperidinyl]
propyl}-N~2~,6-dimethyl-2,4-pyrimidinediamine,
N-{3-[4-(3,4-Dichlorophenoxy)-1-piperidinyl]propyl}-4-
phenyl-2-pyrimidinamine,
N~2~-{3-[4-(3,4-Dichlorophenoxy)-1-piperidinyl]
propyl}-5-fluoro-2,4-pyrimidinediamine,
N~2~-{3-[4-(3,4-Dichlorophenoxy)-1-piperidinyl]
propyl}-N~4~,N~4~,6-trimethyl-2,4-
pyrimidinediamine,
N-}3-[4-(3,4-Dichlorophenoxy)-1-piperidinyl]propyl}-
[4-(trifluoromethyl)-2-pyrimidinediamine,
N-}3-[4-(3,4-Dichorophenoxy)-1-piperidinyl]propyl}-4-
(propylsulfanyl)-2-pyrimidinediamine,
N~2~-{3-[4-(3,4-Dichlorophenoxy)-1-piperidinyl]
propyl}-N~4~-phenyl-2,4-pyrimidinediamine,
N~2~-{3-[4-(3,4-Dichlorophenoxy)-1-piperidinyl]
propyl}-N~4~,6-dimethyl-2,4-pyrimidinediamine,
2-{[2-({3-[4-(3,4-Dichlorophenoxy)-1-piperidinyl]
propyl}amino)-4-pyrimidinyl]amino}-1-ethanol,
2-[[2-({3-[4-(3,4-Dichlorophenoxy)-1-pipendinyl]
propyl}amino)-4-pyrimidinyl](methyl)amino]-1-
ethanol,
N-}3-[4-(3,4-Dichlorophenoxy)-1-piperidinyl]propyl}-4-
(3-pyridinyl)-2-pyrimidinamine,
N-}3-[4-(3,4-Dichlorophenoxy)-1-piperidinyl]propyl}-4-
(3-thienyl)-2-pyrimidinamine,
N-}3-[4-(3,4-Dichlorophenoxy)-1-piperidinyl]propyl}-2-
pyrimidinamine,
N-{3-[4-(3,4-Dichlorophenoxy)-1-piperidinyl]propyl}-4,
6-dimethoxy-2-pyrimidinamine,
N-}3-[4-(3,4-Dichlorophenoxy)-1-piperidinyl]piopyl}-4-
(3-furyl)-2-pyrimidinamine, N-{3-[4-(3,4-Dichlorophenoxy)-1-piperidinyl]propyl}-4-(2-thienyl)-2-pyrimidinamine, N-{3-[4-(3,4-Dichlorophenoxy)-1-piperidinyl]propyl}-2-pyridinamine, 5-Chloro-N-{3-[4-(3,4-dichlorophenaxy)-1-piperidinyl]propyl}-2-pyridinamine, 6-Chloro-N-{3-[4-(3,4-dichlorophenoxy)-1-piperidinyl]propyl}-2-pyridinamine, N-{3-[4-(3,4-Dichlorophenoxy)-1-piperidinyl]propyl}-6-methyl-2-pyridinamine, 6-Chloro-N-}3-[4-(3,4-dichlorophenoxy)-1-piperidinyl]propyl}-2-pyrazinamine, 6-Chloro-N-{3-[4-(3,4-dichlorophenoxy)-1-piperidinyl]propyl}-3-pyrdazinamine, 6-({3-(4-(3,4-Dichlorophenoxy)-1-piperidinyl]propyl}amino)-1,3-dimethyl-2,4(1H,3H)-pyrimidinedione, N-{2-4-(3,4-Dichlorophenoxy)-1-piperidinyl]ethyl}-2,6-dimethoxy-4-pyrimidinamine, N~4~-}2-[4-(3,4-Dichlorophenoxy)-1-piperidinyl]ethyl}-N~2~,N~2~-dimethyl-2,4-pyrimidinediamine, N-{2-[4-(3,4-Dichlorophenoxy)-1-piperidinyl]ethyl}-2-[(methylsulfanyl)methyl]-4-pyrimidinamine, N-(2-[4-(3,4-Dichlorophenoxy)-1-piperidinyl]ethyl}-5-methoxy-2-(methylsulfanyl)-4-pyrimidinamine, N-{2-[4-(3,4-Dichlorophenoxy)-1-piperidinyl]ethyl}-6-methyl-2-(methylsulfanyl)-4-pyrimidinamine, N-{2-[4-(3,4-Dichlorophenoxy)-1-piperidinyl]ethyl}-5-methoxy-2-methyl-4-pyrimidinamine, and N~4~-{2-[4-(3,4-Dichlorophenoxy)-1-piperidinyl]ethyl}-6-methyl-N~2~-phenyl-2,4-pyrimidinediamine.

10. A pharmaceutical composition comprising a compound of formula (I), or a pharmaceutically acceptable salt or solvate thereof; as claimed in claim 1 or claim 9 in association with a pharmaceutically acceptable adjuvant, diluent or carrier.

11. A process for the preparation of a pharmaceutical composition as claimed in claim 10 which comprises mixing a compound of formula (I), or a pharmaceutically acceptable salt or solvate thereof, as claimed in claim 1 or claim 9 with a pharmaceutically acceptable adjuvant, diluent or carrier.

12. The process of claim 8 wherein $L_1$ is a hydroxyl group.

13. The process of claim 8 whercin $L_1$ is halide group.

14. The process of claim 8 wherein said addition salt of formula (III) is trifluoroacetate.

15. The process of claim 8 wherein $L_3$ is halogen atom.

* * * * *

UNITED STATES PATENT AND TRADEMARK OFFICE
CERTIFICATE OF CORRECTION

PATENT NO. : 6,946,478 B2
APPLICATION NO. : 10/339261
DATED : September 20, 2005
INVENTOR(S) : Andrew Baxter et al.

It is certified that error appears in the above-identified patent and that said Letters Patent is hereby corrected as shown below:

Title page, please insert:

-- Foreign Application Priority Data
Mar. 26, 1999 (SE) .................................. 9901117
Jun. 10, 1999 (SE) .................................. 9902194 --

Column 148, line 5, "$C_1-C_6$" should be -- $C_1-C_4$ --.

Column 148, line 27, "$C_2-C_6$" should be -- $C_1-C_6$ --.

Column 148, line 64, "alkylcarbonylammno" should be -- alkylcarbonylamino --.

Column 149, line 38, "m is I" should be -- m is 1 --.

Column 149, line 43, "informula" should be -- in formula --.

Column 149, line 54, "2-[3-}2" should be -- 2-[3-{2 --.

Column 150, line 3, "pipezidinyl" should be -- piperidinyl --.

Column 150, lines 5 and 9, "(2" should be -- {2 --.

Column 150, line 16, "pipendinyl" should be -- piperidinyl --.

Column 150, line 22, "~4~{2" should be -- ~4~-{2 --.

Column 150, line 35, after "ethyl}", delete "-N".

Column 150, line 41, "-[4-" should be -- -4- --.

Column 150, lines 46, 48, 50, 55, 57, and 59, "pipendinyl" should be -- piperidinyl --.

Column 150, line 50, "N~2~-[4" should be -- N~2~-{2-[4 --.

Column 150, line 53, "dichloraphenoxy" should be -- dichlorophenoxy --.

Column 151, line 2, after "piperidinyl", ")" should be -- ] --.

Column 151, line 5, after "benzyl", "[" should be -- ] --.

UNITED STATES PATENT AND TRADEMARK OFFICE
CERTIFICATE OF CORRECTION

PATENT NO.        : 6,946,478 B2
APPLICATION NO. : 10/339261
DATED              : September 20, 2005
INVENTOR(S)      : Andrew Baxter et al.

It is certified that error appears in the above-identified patent and that said Letters Patent is hereby corrected as shown below:

Column 151, line 7, after "ethyl", ")" should be -- ] -- and after "piperidinyl", "]" should be -- } --.

Column 151, line 10, "6-[({2-4-" should be -- 6-[({2-[4- -- and "pipendinyl" should be -- piperidinyl --.

Column 151, line 15, "methy" should be -- methyl --.

Column 151, line 24, "{[5" should be -- {[(5 -- and "-[4-yl" should be -- -4-yl --.

Column 151, line 35, "ammo" should be -- amino --.

Column 151, line 38, "Chlorophonyl" should be -- Chlorophenyl --.

Column 151, line 39, "[ethyl}" should be -- ]ethyl} --.

Column 151, lines 53, 55, 62, 64, and 66, "pipendinyl" should be -- piperidinyl --.

Column 151, line 56, "dimetyl" should be -- dimethyl --.

Column 152, line 6, "N~-2~dimethyl-2" should be -- N~2~dimethyl-2 --.

Column 152, line 7, "-(3-" should be -- -{3- --.

Column 152, line 15, "ropyl" should be -- propyl --.

Column 152, line 21, "}3" should be -- {3 --.

Column 152, line 43, "}3" should be -- {3 --.

Column 152, line 44, "[4" should be -- 4 --.

Column 152, line 45, "}3" should be -- {3 --.

Column 152, lines 57, 59, 61, and 66, "}3" should be -- {3 --.

Column 153, line 5, "dichlorophenaxy" should be -- dichlorophenoxy --.

UNITED STATES PATENT AND TRADEMARK OFFICE
CERTIFICATE OF CORRECTION

PATENT NO. : 6,946,478 B2
APPLICATION NO. : 10/339261
DATED : September 20, 2005
INVENTOR(S) : Andrew Baxter et al.

It is certified that error appears in the above-identified patent and that said Letters Patent is hereby corrected as shown below:

Column 153, line 12, "}3" should be -- {3 --.

Column 153, line 15, "pyrdazinamine" should be -- pyridazinamine --.

Column 153, line 16, "(4" should be -- [4 --.

Column 153, line 19, "N-{2-4-" should be -- N-{2-[4- --.

Column 153, line 21, "}2" should be -- {2 --.

Column 153, line 26, "N-(2-[4-" should be -- N-{2-[4- --.

Signed and Sealed this

Sixth Day of May, 2008

JON W. DUDAS
*Director of the United States Patent and Trademark Office*